United States Patent [19]

Luo et al.

[11] Patent Number: 5,453,533
[45] Date of Patent: Sep. 26, 1995

[54] INHIBITORS OF INFLUENZA VIRUS NEURAMINIDASE AND METHODS OF MAKING AND USING THE SAME

[75] Inventors: Ming Luo; Wayne J. Brouillette; Gillian Air, all of Birmingham, Ala.

[73] Assignee: The University of Alabama at Birmingham, Birmingham, Ala.

[21] Appl. No.: 227,549

[22] Filed: Apr. 14, 1994

[51] Int. Cl.⁶ ............................ C07C 69/00; C07C 69/62; A01N 37/28; A01N 41/02
[52] U.S. Cl. ............... 560/142; 560/145; 560/147; 560/155; 560/156; 560/179; 560/184; 560/205
[58] Field of Search ........................ 560/142, 145, 560/147, 155, 156, 179, 184, 205; 514/888, 507, 517, 518, 519, 520

[56] References Cited

U.S. PATENT DOCUMENTS

| | | | |
|---|---|---|---|
| 4,478,823 | 10/1984 | Sanderson | 424/194.1 |
| 4,537,769 | 8/1985 | Cerini | 424/210.1 |
| 5,360,817 | 11/1994 | Von Izstein et al. | 514/459 |

OTHER PUBLICATIONS

G. M. Air and W. G. Laver, "The Neuraminidase of Influenza Virus", *Proteins: Structure, Function, and Genetics*, 6, 341–356 (1989).

P. Bossart-Whitaker, et al., "Three-Dimensional Structure of Influenza A N9 Neuraminidase and its Complex with the Inhibitor 2-Deoxy-2,3-dehydro-N-acetyl Neuraminic Acid", *J. Mol. Biol.*, 232, 1069–1089 (1993).

K. W. Brammer, et al., Antiviral Properties of 1-Phenoxymethyl-3,4-dihydro- and 1,2,3, 4-Tetrahydroisoquinolines, *Nature*, 219, 515–517 (1968).

R. Brossmer, et al., "Inhibition Studies on Vibrio cholerae Neuraminidase", *Hoppe–Seyler's Z. Physiol. Chem.*, 358, 391–396 (1977).

(List continued on next page.)

Primary Examiner—Arthur C. Prescott

Attorney, Agent, or Firm—Needle & Rosenberg

[57] ABSTRACT

An influenza virus neuraminidase inhibitor, its analogs, its pharmaceutically acceptable salts, derivatives, and mixtures thereof having the following formula:

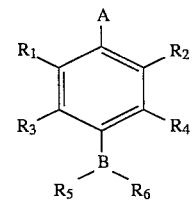

where A is $CO_2H$, $CO_2H_3$, $NO_2$, $SO_3H$ or $PO_3H_2$, B is CH, N, O or S, $R_1$ and $R_2$ are H, $NO_2$ or $(CH_m)_n X_1$ where m=1 or 2, n is an integer from 0 to 4 and $X_1$ is guanidino, OH, $NH_2$, SH, $NO_2$, F, Cl, Br, I, CN, $CF_3$, $CO_2H$, $SO_3H$ or $PO_3H_2$, $R_3$ and $R_4$ are H, $(CH_o)_p X_2$, $(CH_o)_p CHX_2CH_2X_2$, $NH(CH_o)_p CHX_2$, $CH_2X_2$, $NHCO(CH_o)_p CH_2X_2$ or $NHCO(CH_o)_p CHX_2CH_2X_2$ where o=1 or 2, p is an integer from 0 to 4 and $X_2$ is H, guanidino, OH, $NH_2$, SH, $NO_2$, $CF_3$, $CO_2H$, $SO_3H$ or $PO_3H_2$, $R_5$=H, OH, $NH_2$, $(CH_k)_1 X_3$, $CO(CH_k)_1 X_3$, $SO(CH_k)_1 X_3$ or $SO_2(CH_k)_1 X_3$ where k=1 or 2, 1 is an integer from 0 to 4 and $X_3$ is guanidino, OH, $NH_2$, SH, $NO_2$, $CF_3$, $CO_2H$, $SO_3H$ or $PO_3H_2$, $R_6$ is H, $CH(OH)X_4$, $CH(NH_2)X_4$, $COX_4$, $SOX_4$, or $SO_2X_4$, where $X_4$ is H, $CH_3$, $CH_3CH_2$, $CH_3CHCH_3$, $CH_3CH_2 CH_2$ or halogen substituted analogs of $X_4$. The inhibitor in a composition with a pharmaceutically acceptable carrier. A method of inhibiting influenza virus neuraminidase where the inhibitor is administered to a subject in a pharmaceutically acceptable amount along with effective amounts of a pharmaceutically acceptable carrier. Methods of marking a pharmaceutical composition of an acceptable carrier and the inhibitor. Methods of treating and preventing a subject infected with influenza virus (type A or B) using the inhibitor.

53 Claims, 9 Drawing Sheets

OTHER PUBLICATIONS

G. Bruno and L. Randaccio, "A Refinement of the Benzoic Acid Structure at Room Temperature", *Acta Cryst.,* B36, 1711–1712 (1980).

R. F. Bryan, et al., "3–(p–Bromobenzoyl)–1, 3–thiazolidine–2–thione", *Acta Cryst.,* B36, 1709–1710 (1980).

W. P. Burmeister, et al., "The 2.2 Å Resolution Crystal Structure of Influenza B Neuraminidase and its Complex with Sialic Acid", *EMBO J.,* 11, 49–56 (1992).

P. A. Carpy and J. L. Goursolle, "Acide [Dichloro–2, 3(Thenoyl–2)–4 Phenoxy] Acetique (Acide Tienilique)", *Acta Cryst.,* B36, 1706–1708 (1980).

G. P. Ellis and R. T. Jones, "One–Step Synthesis and Spectral Study of Some 1–Methylbenzimidazoles, Including Use of a Lanthanide Shift Reagent", *J. Chem. Soc. Perk. Trans. I,* 8, 903–909 (1974).

P. H. Gozlan and C. Riche, "Analogues de la Noraderenaline. Structure Cristalline de la (Methylene Dioxy–3', 4')–phenyl–2 Hydroxy–2 Acetamideoxime", *Acta Cryst.,* B32, 1662–1665 (1976).

T. H. Haskell, et al., "Neuraminidase Inhibition and Chemotherapy", *J. Med. Chem.,* 13, 697–704 (1970).

M. N. Janakiraman, et al., "Structural Evidence for Hydrolysis Catalyzed by Influenza Virus Neuraminidase Driven by Stabilization of the Oxocarbonium Ion Intermediate", *Biochemistry,* 33, 8172–8179 (1994).

Y. Kageyama, et al., "Structure of the Phosphate Form of p–Nitrocinnamic acid", *Acta Cryst.,* C49, 833–834 (1993).

F. Kasuya, et al., "Metabolism of Benoxinate in Humans", *J. Pharm. Sci.,* 76, 303–305 (1987).

T. Kudo, et al., "Synthesis of the Potent Inhibitors of Neuramindase. N–(1,2–Dihydroxypropyl) Derivatives of Siastatin B and its 4–Deoxy Analogs", *J. Antibiot.,* 46, 300–309 (1993).

V. Kumar, et al., "Methyl 5–Acetamido–2,6–anhydro–3, 5–dideoxy–D–manno–non–2–en–4–ulosonate", *Carbohyd. Res.,* 103, 281–285 (1982).

P. Meindl, et al., "Inhibition of Neuraminidase Activity by Derivatives of 2–Deoxy–2,3–dehydro–N–acetylneuraminic Acid", *Virology,* 58, 457–463 (1974).

R. M. Metzger, et al., "Crystal Structure of DMAP–C–HMTCAQ, $C_{30}$ $H_{20}N_6O_2N_1N$, N–dimethylaminophenylcarbamate–2'–hydroxymethyl–11, 11,12,12–tetracyano–anthraquinodimethan", *J. Cryst. Spect. Research.,* 19(3), 475–482 (1989).

R. M. Metzger, et al., "Structure of MAP:MNA, the 1:1 Adduct Between (R)Methyl2–(2, 4–Dinitroanilino)propanoate (MAP) and 2–Methyl–4–nitroaniline (MNA), a New Nonlinear Optical Crystal", *Acta Cryst.,* C49, 738–741 (1993).

T. Nagai, et al., "In Viro Anti–Influenza Virus Activity of Plant Flavonoids Possessing Inhibitory Activity for Influenza Virus Sialidase", *Antiviral Res.,* 19, 207–217 (1992).

G. O'Neill, "Have Aussies Found a Cure for the Flu?", *J. NIH Res., 5, 40–42 (1993).*

B. B. Nielsen and I. K. Larsen, "3,4, 5–Trihydroxybenzohydroxamic Acid Monohydrate, A Ribonucleotide Reductase Inhibitor", *Acta Cryst.,* C49, 810–813 (1993).

P. Palese and R. W. Compans, "Inhibition of Influenza Virus Replication in Tissue Culture by 2–Deoxy–2, 3–dehydro–N–trifluoroacetylneuraminic acid (FANA): Mechanism of Action", *J. Gen. Virology,* 33, 159–164 (1976).

E. Schreiner, et al., "Synthesis of Some 2,3–Didehydro–2–deoxysialic Acids Structurally Varied at C–4 and their Behavior Towards Sialidase from *Vibrio cholerae*", *Liebigs Ann. Chem.,* 129–134 (1991).

S. Soundarajan, et al., "Structure 4–Carboxy–2–nitrobenzeneboronic Acid", *Acta Cryst.,* C49, 690–693 (1993).

N. R. Taylor, et al., "Molecular Modeling Studies on Ligand Binding to Sialiase from Influenza Virus and the Mechanism of Catalysis", *J. Med. Chem.,* 37, 616–624 (1994).

W. R. Tulip, et al., "Refined Atomic Structures of N9 Subtype Influenza Virus Neuraminidase and Escape Mutants", J. Mol. Biol., 221, 487–497 (1991).

W. R. Tulip, et al., "Refined Crystal Structure of the Influenza Virus N9 Neuraminidase–NC41 Fab Complex", *J. Mol. Biol.,* 227, 122–148 (1992).

J. N. Varghese, et al., "The Structure of the Complex Between Influenza Virus Neuraminidase and Sialic Acid, the Viral Receptor", *Proteins: Structure, Function and Genetics,* 14, 327–332 (1992).

A. Vasella and R. Wyler, "Sythesis of a Phosphonic Acid Analogue of N–Acetyl–2,3–didehydro–2–deoxyneuraminic Acid, and Inhibitor of *Vibrio cholerae* Sialidase", *Helv. Chim. Acta,* 74, 451–463 (1991).

R. Varma and I. Kahn, "Synthesis of Indophenazines and 6–Piperidino/morpholinomethyl–indophenazines As Possible Excystment and Cysticidal Agents", *J. Ind. Chem. Soc.,* 55, 1043–1045 (1978).

L. M. Von Itzstein, et al., "Derivatives and Analogues of 2–Deoxy–2,3–didehydro–N–acetylneuraminic Acid and their Use as Antiviral Agents", *Intern. Patent WO 91/16320* (Oct. 31, 1994).

A. Okuyama, et al., "Preparation of quanidinobenzoic acid amides as antiviral agents (182869p)", *25–Benzenes,* 115, 879 (1991).

Polar Contacts (<4.0 Å) Between N9 NA and DANA.
(Bossart-Whitaker et al., 1993)

| NA | DANA | Distance (Å) |
|---|---|---|
| 119 ARG NH1 | O1B | 3.41 |
| 119 ARG NH2 | O1B | 2.88 |
| 120 GLU OE1 | O4 | 3.46 |
| 152 ASP OD1 | O4 | 3.81 |
| 152 ASP OD1 | O10 | 3.55 |
| 152 ASP OD1 | O7 | 3.73 |
| 153 ARG NE | O10 | 2.71 |
| 153 ARG NH1 | O10 | 3.24 |
| 278 GLU OE1 | O8 | 3.85 |
| 278 GLU OE1 | O9 | 3.05 |
| 278 GLU OE2 | O8 | 2.79 |
| 278 GLU OE2 | O9 | 3.39 |
| 279 GLU OE1 | O6 | 3.53 |
| 279 GLU OE1 | O6 | 3.59 |
| 294 ARG NH1 | O1A | 3.50 |
| 294 ARG NH1 | O8 | 3.89 |
| 294 ARG NH2 | O1A | 3.67 |
| 294 ARG NH2 | O6 | 3.64 |
| 294 ARG NH2 | O8 | 3.69 |
| 372 ARG NH1 | O1A | 2.76 |
| 372 ARG NH1 | O1B | 3.36 |
| 372 ARG NH2 | O1A | 3.86 |
| 372 ARG NH2 | O1B | 2.99 |
| 406 TYR OH | O1A | 3.43 |
| 406 TYR OH | O1B | 3.39 |
| 406 TYR OH | O6 | 2.89 |

GENERAL STRUCTURE I $q_O = -0.35$ e $q_O = -0.56$ e

INHIBITORS OF INFLUENZA VIRUS NEURAMINIDASE AND METHODS OF MAKING AND USING THE SAME

GOVERNMENT INTEREST

This application has been supported by two grants from the National Institutes of Health: R01 AI26718 to Dr. Gillian Air and U01 AI31888 to Dr. Ming Luo.

BACKGROUND

1. Field of the Invention

This invention relates to inhibitors of influenza virus neuraminidase. In particular, this invention provides novel inhibitors to human influenza virus types A and B neuraminidase, methods of making the inhibitors, methods of treatment using the inhibitors and methods of prophylaxis from influenza infection.

2. Background of the Invention

Influenza virus epidemics occur every winter, causing significant morbidity and mortality in the U.S. population. Vaccines must be reformulated each year in response to antigenic variation and are frequently ineffective against new influenza variants. The only licensed anti-influenza drug, amantadine, and the related compound rimantadine, are effective only against influenza subtype A, and the virus can rapidly acquire resistance.

Influenza viruses are enveloped RNA viruses that are classified into three serological types: A, B, and C. Two major surface glycoproteins, hemagglutinin (HA) and neuraminidase (NA), are responsible for the antigenic properties of the viruses. For influenza A, there are at least 9 subtypes of NA and 13 subtypes of HA, in contrast to only one subtype of influenza B NA and HA. Influenza C contains both HA and NA activities in a single surface glycoprotein, and only one subtype is known (Hay et. al., 1991 ).

Influenza C is not considered a serious disease and most adults have protective antibodies. Immunity from influenza A and B, however, does not last long since the virus is constantly undergoing antigenic variation. Influenza A undergoes a progressive antigenic drift and, in addition, undergoes an antigenic shift every 10–20 years in which a "new" HA and sometimes NA appears. In some cases, antigenic shift has resulted from the reassorting of gene segments from animal and bird viruses into a human strain. Influenza B has not undergone antigenic shift, perhaps because it is not found in birds or animals. Since 1977, there have been 3 influenza viruses circulating in humans: influenza A subtypes H3N2 and H1N1, and influenza B. Epidemics occur every winter, and usually one virus predominates. The current virus (c. 1993) has significantly different antigenic properties compared to the previously circulating variant or vaccine strain. The disease has a high infection rate and costs to the U.S. in a bad year are estimated to be 3–5 billion dollars (Murphy and Webster, 1990). The elderly are at high risk for serious complications from influenza, and excess mortality in the U.S. is estimated to be 10,000–20,000 each winter. Currently available vaccines and drugs have clearly failed to control influenza in humans.

The trivalent influenza vaccine currently licensed in the U.S. contains formalin-inactivated whole virus or partially-purified HA and NA (split vaccine) from H3N2, H1N1, and B strains. The whole virus preparation is more antigenic than the split form, but its toxicity precludes administration to young children. Neither vaccine confers long term protection, and even in the absence of antigenic variation, the vaccine would have to be given every year. Clinical trials of the promising cold-adapted live attenuated vaccine have not yet shown increased efficacy (Wright, 1992), although toxicity in young children is reduced compared to the split vaccine (Edwards et. al., 1991). The elderly, who are at greatest risk for severe complications and death from influenza, react poorly to the killed vaccine and have shown no better response in clinical trials with the live, attenuated vaccine (Powers et. al., 1991).

Only two anti-influenza drugs, amantadine and rimantadine, are currently licensed in the United States. They act by blocking the viral-coded ion channel (M2 protein) in influenza A but have no effect on influenza B, which uses a different ion channel. Resistance to amantadine or rimantadine develops quickly; typically the primary patient benefits from amantadine therapy, but contracts a resistant virus (Hayden and Hay, 1992). Therefore, a need exists for new, broad-spectrum anti-influenza drugs that act by different mechanisms.

The two major surface glycoproteins of influenza viruses A and B are essential for infectivity and offer potential targets for antiviral drug development. Hemagglutinin (HA) is responsible for viral attachment to host cells by binding to terminal sialic acid residues on host cell surface glycoconjugates, and HA is also involved in mediating membrane fusion. Neuraminidase (NA) (also called sialidase or acyineuraminyl hydrolase, EC 3.2.1.18) destroys the host cell viral receptor by catalyzing the hydrolysis of $\alpha$-2,3- or $\alpha$-2,6-glycosidic bonds to terminal sialic acid residues of surface glycoconjugates (Paulson, 1985; Daniels et. al., 1987; Suzuki et. al., 1986). This facilitates release and prevents aggregation of progeny virus (Palese et. al., 1974). Therefore, the inhibition of either coat glycoprotein is desirable and should provide antiviral effects. In particular, the structure-based design of inhibitors for NA is highly desirable.

Effective inhibitors of NA thus should provide anti-influenza agents. For instance, monoclonal antibodies against NA were shown to terminate viral infection, and the anti-NA response was protective (Webster et. al, 1988). A neuraminidase-minus mutant of influenza A (Liu and Air, 1993) was produced, and the mutant was unable to replicate more than one cycle without added exogenous neuraminidase. Additionally, mutant influenza A viruses lacking the NA stalk do not replicate in eggs and are much less virulent in mice (Castrucci and Kawaoka, 1993).

Influenza NA, which accounts for 5–10% of the virus protein, has an approximate molecular weight (MW) of 250,000 and lies mostly outside of the viral membrane. It is a tetramer with C4 symmetry and consists of an N-terminal membrane-anchored domain, a stalk, and a globular head. Each subunit of the head contains a catalytic site and is a glycosylated polypepfide with MW 50,000 containing 6 β-sheets arranged in a propeller formation. Protcolytic cleavage of the stalk has produced biologically and antigenically active heads (Air and Laver, 1989). Heads from several viruses have been crystallized, and x-ray structures of NA heads from influenza A N2 (Varghese et. al, 1992), N9 (Bossart-Whitaker et. al., 1993; Tulip et. al., 1991), N9 complexed with monoclonal antibody NC41 (Tulip et. al., 1992), and two B virus NA's (Janakiraman et. al, 1994; Burmeister et. al, 1992) have been solved. These studies reveal that, while sequence homology among neuraminidases is often low (influenza A N9 NA and B/Lee NA have only 28% sequence homology), the tertiary structures are well-conserved. In particular, a group of 18 conserved amino acid residues constitute a strain-invariant sialic acid binding site among all influenza NA's thus far studied.

Thus, effective inhibitors of NA will provide highly desirable anti-influenza agents against type A and B variants. Site-specific mutations of conserved residues provided correctly folded mutants that, in most cases, were enzymatically inactive (Lentz et. al, 1987). The apparent importance of this conserved site to viral replication suggests that the virus may not be able to evade anti-influenza NA inhibitors through mutation. Additionally, since NA acts at the end of the viral replication cycle, a potential advantage of anti-influenza NA inhibitors is that sufficient viral protein may be provided to stimulate the immune system.

The prior art lacked available atomic coordinates for earlier NA structures. Thus, the x-ray crystal structures for NA first had to be solved. In this fashion, original structures for an N9 influenza A NA (Bossart-Whitaker et. al, 1993) and an influenza B NA (Janakiraman et. al, 1993) were obtained. These have been refined as both the native enzyme and as complexes with several ligands, including sialic acid and DANA (discussed infra). Also, crystals have been obtained and the x-ray structure refined-for a published N2 influenza A NA.

Influenza NA exhibits a broad pH range with the optimum between 5.8 and 6.6, and using a small trisaccharide substrate (N-acetyl neuraminyl lactose), the $K_m$ is about 0.4 mM (Drzeniek, 1972; Mountford et. al., 1982). The product of catalysis, sialic acid (N-acetylneuraminic acid or NANA) is a modest inhibitor with a $K_i$ of about 1 mM. A number of other compounds have been evaluated as in vitro inhibitors of influenza neuraminidase, and among the most potent thus far described is 2-deoxy-2,3-dehydro-N-acetylneuraminic acid (DANA), which inhibits with a $K_i$ of 10 μM (Meindl et. al., 1974). A DANA analog, 2-deoxy-2,3-dehydro-N-(trifiuoroacetyl)neuraminic acid (FANA), exhibited greater in vitro activity (Palese and Compans, 1976). While no reports have described in vivo anti-influenza effects for either DANA or FANA, several new DANA analogs have recently been described that possess in vivo antiviral effects, confirming that inhibitors of NA provide useful anti-influenza agents (Von Itzstein et. al., 1991; O'Neill, 1993).

The 20 year old observation that DANA was an effective in vitro inhibitor of NA has resulted in the preparation of a large number of synthetic derivatives varied mainly at the 2-, 4-, 5-, and 6-positions (for example, Meindl et. al, 1974; Schreiner et. al., 1991; Kumar et al., 1982; Vasella et. al., 1991). Unfortunately, except for an early study (Meindl et. al., 1974), these have not been assayed with influenza NA, but instead with NA from *Vibrio cholerae* or *Arthrobacter sialophilus*. Numerous synthetic sialic acid (NANA) analogs (for example, Glanzer et al., 1991; Yamamoto et al., 1992; Mack et al., 1992) have also been reported, although these are typically much less effective inhibitors of NA than DANA or FANA. It has been suggested that DANA, which unlike NANA contains a double bond at the C2–C3 position, is a planar "transition state analog" inhibitor (Flasher et al., 1983), since it may mimic a planar oxonium cation intermediate suggested to be involved during hydrolysis. Recent studies of influenza virus NA using NMR, molecular dynamics, and kinetic isotope effects support a sialosyl cation transition-state complex in the reaction (Chong et. al., 1992). Finally, only a few novel NA inhibitors that are not pyrans or furans have been described, including isoquinolines (Brammer et al., 1968), α-mercaptocinnamic acids and imidazoles (Haskell et. al., 1970), oxamic acids (Brossmer et. al., 1977), the piperidine, siastatin B, and derivatives (Kudo et. al., 1993), and plant flavonoids (Nagai et. al., 1992). Due to limited investigations with influenza virus NA, and the possibility that NA's from such diverse sources as viruses and bacteria have different binding sites (even *Vibrio cholerae* and *Arthrobacter sialophilus* show different inhibitor specificity) (Wang et. al., 1978; Miller et. al., 1978), these previous structure-activity relationship (SAR) studies provide little reliable assistance for designing new anti-influenza drugs. It is clear that a novel approach to the design of new NA inhibitors is needed.

One attempt at rational design of inhibitors has resulted in a class of compounds based on 2-deoxy-2,3-didehydro-D-N-acetylneuraminic acid (Neu5Ac2en). These inhibitors have $K_i$ binding constants as high as $10^{-10}$M, but they are excreted from-the infected person's body very rapidly and thus are not efficient. Oral activity has not been reported. (Brammer, *Nature,* 1968).

It should be noted that, for therapeutic utility as anti-influenza agents, inhibitors of influenza NA should not inhibit mammalian sialidases. The latter have been implicated in a number of important metabolic processes including the regulation of cell proliferation (Usuki et. al., 1988a), the clearance of plasma proteins (Ashwell and Morell, 1974), and the catabolism of gangliosides and glycoproteins (Usuki et. al., 1988b). The optimization of binding to influenza NA described in the structure-based approach proposed herein will provide selective inhibitors and concomitant methods for making and using them.

SUMMARY OF THE INVENTION

The current invention relates to the structure-based design, synthesis and in vitro evaluation of non-carbohydrate inhibitors for the neuraminidase (NA) of influenza viruses A and B. Using structure-based drug design, a broad class of novel, potent, and selective inhibitors of influenza NA has been developed.

The present invention provides an influenza virus neuraminidase inhibitor, its analogs, its pharmaceutically acceptable salts, derivatives, and mixtures thereof having the following formula:

GENERAL STRUCTURE I

[benzene ring with substituents $R_1$, $R_2$ at top positions, A at top, $R_3$, $R_4$ at bottom positions, B at bottom connected to $R_5$ and $R_6$]

wherein A=$CO_2H$, $CO_2CH_3$, $NO_2$, $SO_3H$ or $PO_3H_2$; wherein B=CH, N, O or S; wherein $R_1$ and $R_2$=H, $NO_2$ or $(CH_m)_nX_1$ where m=1 or 2, n is an integer from 0 to 4 and $X_1$=guanidino, OH, $NH_2$, SH, $NO_2$, F, Cl, Br, I, CN, $CF_3$, $CO_2H$, $SO_3H$ or $PO_3H_2$; wherein $R_3$ and $R_4$=H, $(CH_o)_pX_2$, $(CH_o)_pCHX_2CH_2X_2$, $NH(CH_o)_pCHX_2CH_2X_2$, $NHCO(CH_o)_pCH_2X_2$ or $NHCO(CH_o)_pCHX_2CH_2X_2$ where o=1 or 2, p is an integer from 0 to 4 and $X_2$= H, guanidino, OH, $NH_2$, SH, $NO_2$, $CF_3$, $CO_2H$, $SO_3H$ or $PO_3H_2$; wherein $R_5$=H, OH, $NH_2$, $(CH_k)_1X_3$, $CO(CH_k)_1X_3$, $SO(CH_k)_1X_3$ or $SO_2(CH_k)_1X_3$ where k=1 or 2, l is an integer from 0 to 4 and $X_3$=guanidino, OH, $NH_2$, SH, $NO_2$, $CF_3$, $CO_2H$, $SO_3H$ or $PO_3H_2$; wherein $R_6$=H, $CH(OH)X_4$, $CH(NH_2)X_4$, $COX_4$, $SOX_4$, or $SO_2X_4$, where $X_4$=H, $CH_3$, $CH_3CH_2$, $CH_3CHCH_3$, $CH_3CH_2CH_2$ or halogen substituted analogs of $X_4$; and wherein, when A is $CO_2H$ and B is N, $R_3$ is not H when $R_4$ is H or OH and wherein $R_3$ is not $NO_2$ or $NH_2$ when $R_4$ is H.

Also provided is an influenza virus neuraminidase inhibitor, its analogs, its pharmaceutically acceptable salts, derivatives, and mixtures thereof having the following formula:

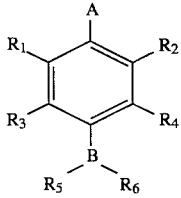

GENERAL STRUCTURE I wherein A=$CO_2H$ or $CO_2CH_3$; wherein B=CH or N; wherein $R_1$ and $R_2$ =H or $NO_2$; wherein $R_3$=H, OH, $NH_2$, guanidino, $NO_2$, F, Cl or Br; wherein $R_4$ =$QR_7$ where Q=O, NH or $CH_2$ and $R_7$=H, $(CH_2)_oX_1$, $(CH_2)_oCHX_1CH_2$ $X_1$, $CO(CH_2)_oCH_2X_1$ or $CO(CH_2)_o$ $CHX_1CH_2X_1$ where o is an integer from 0 to 4 and $X_1$ =H, guanidino, OH or $NH_2$; wherein $R_5$=$COCH_3$; wherein $R_6$=$(CH_2)_pX_2$ where p is an integer from 0 to 4 and $X_2$=OH, $NH_2$ or guanidino; and wherein, when A is $CO_2H$ and B is N, $R_3$ is not H when $R_4$ is H or OH and wherein $R_3$ is not $NO_2$ or $NH_2$ when $R_4$ is H.

A further embodiment provides an influenza virus neuraminidase inhibitor, its analogs, its pharmaceutically acceptable salts, derivatives, and mixtures thereof having the following formula:

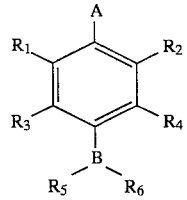

GENERAL STRUCTURE I wherein A=$CO_2H$ or $CO_2CH_3$; wherein B=N; wherein $R_1$=H or $NO_2$; wherein $R_2$=H or $NO_2$; wherein $R_3$=H, OH, $NO_2$, $NH_2$ or guanidino; wherein $R_4$=H, OH, OAc, $NH_2$, guanidino, $NHCOCH_2OH$, $NHCOCH(OH)CH_2OH$, $NHCOCH_2NH_2$, $NHCOCH_2CH_2CH_2NH_2$, CHO, $CH_2OH$, $CH_2OAc$, $CH_2CH_2OH$, $CH_2CH_2CH_2OH$, $CH_2CH(OH)CH_2OH$, $CH_2CH_2CH_2CH_2OH$, $CH_2CH_2CH(OH)CH_2OH$, $CH_2I$, $CH=CH_2$, $CH_2CH=CH_2$ or $CH_2CH_2CH=CH_2$; wherein $R_5$=H; wherein $R_6$=$COCH_3$; and wherein $R_4$ is not H when $R_3$ is H or OH and wherein $R_4$ is not $NO_2$ or $NH_2$ when $R_3$ is H.

Also provided is a composition for inhibiting influenza virus neuraminidase, comprising an effective amount of a pharmaceutically acceptable earlier and a compound, its analogs, its pharmaceutically acceptable salts, derivatives, or mixtures thereof, having the following formula:

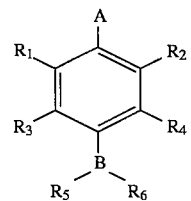

GENERAL STRUCTURE I wherein A=$CO_2H$, $CO_2CH_3$, $NO_2$, $SO_3H$ or $PO_3H_2$; wherein B=CH, N, O or S; wherein $R_1$ and $R_2$=H, $NO_2$ or $(CH_m)_nX_1$ where m=1 or 2, n is an integer from 0 to 4 and $X_1$=guanidino, OH, $NH_2$, SH, $NO_2$, F, Cl, Br, I, CN, $CF_3$, $CO_2H$, $SO_3H$ or $PO_3H_2$; wherein $R_3$ and $R_4$=H, $(CH_o)_pX_2$, $(CH_o)_pCHX_2CH_2X_2$, $NH(CH_o)_pCHX_2CH_2X_2$, $NHCO(CH_o)_pCH_2X_2$ or $NHCO(CH_o)_pCHX_2CH_2X_2$ where o=1 or 2, p is an integer from 0 to 4 and $X_2$= H, guanidino, OH, $NH_2$, SH, $NO_2$, $CF_3$, $CO_2H$, $SO_3H$ or $PO_3H_2$; wherein $R_5$=H, OH, $NH_2$, $(CH_k)_1X_3$, $CO(CH_k)_1X_3$, $SO(CH_k)_1X_3$ or $SO_2$ $(CH_k)_1X_3$ where k=1 or 2, 1 is an integer from 0 to 4 and $X_3$=guanidino, OH, $NH_2$, SH, $NO_2$, $CF_3$, $CO_2H$, $SO_3H$ or $PO_3H_2$; wherein $R_6$=H, $CH(OH)X_4$, $CH(NH_2)X_4$, $COX_4$, $SOX_4$, or $SO_2X_4$, where $X_4$=H, $CH_3$, $CH_3CH_2$, $CH_3CHCH_3$, $CH_3CH_2CH_2$ or halogen substituted analogs of $X_4$; and wherein, when A is $CO_2H$ and B is N, $R_3$ is not H when $R_4$ is H or OH and wherein $R_3$ is not $NO_2$ or $NH_2$ when $R_4$ is H.

The present invention also provides a composition for inhibiting influenza virus neuraminidase, comprising an effective amount of a pharmaceutically acceptable carrier and a compound, its analogs, its pharmaceutically acceptable salts, derivatives, or mixtures thereof, having the following formula:

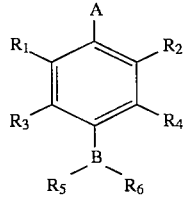

GENERAL STRUCTURE I wherein A=$CO_2H$ or $CO_2CH_3$; wherein B=CH or N; wherein $R_1$ and $R_2$ =H or $NO_2$; wherein $R_3$=H, OH, $NH_2$, guanidino, $NO_2$, F, Cl or Br; wherein $R_4$ =$QR_7$ where Q=O, NH or $CH_2$ and $R_7$=H, $(CH_2)_oX_1$, $(CH_2)_oCHX_1CH_2$ $X_1$, $CO(CH_2)_oCH_2X_1$ or $CO(CH_2)_oCHX_1$ $CH_2X_1$ where o is an integer from 0 to 4 and $X_1$ =H, guanidino, OH or $NH_2$; wherein $R_5$=$COCH_3$; wherein $R_6$=$(CH_2)_pX_2$ where p is an integer from 0 to 4 and $X_2$=OH, $NH_2$ or guanidino; and wherein, when A is $CO_2H$ and B is N, $R_3$ is not H when $R_4$ is H or OH and wherein $R_3$ is not $NO_2$ or $NH_2$ when $R_4$ is H.

Also provided is a composition for inhibiting influenza virus neuraminidase, comprising an effective amount of a pharmaceutically acceptable carder and a compound, its analogs, its pharmaceutically acceptable salts, derivatives, or mixtures thereof, having the following formula:

GENERAL STRUCTURE I

[Structure: benzene ring with A at top, $R_1$ and $R_2$ at positions adjacent to A, $R_3$ and $R_4$ at next positions, B at bottom connected to $R_5$ and $R_6$]

wherein A=$CO_2H$ or $CO_2CH_3$; wherein B=N; wherein $R_1$=H or $NO_2$; wherein $R_2$=H or $NO_2$; wherein $R_3$=H, OH, $NO_2$, $NH_2$ or guanidino; wherein $R_4$=H, OH, OAc, $NH_2$, guanidino, $NHCOCH_2OH$, $NHCOCH(OH)CH_2OH$, $NHCOCH_2NH_2$, $NHCOCH_2CH_2CH_2NH_2$, CHO, $CH_2OH$, $CH_2OAc$, $CH_2CH_2OH$, $CH_2CH_2CH_2OH$, $CH_2CH(OH)CH_2OH$, $CH_2CH_2CH_2CH_2OH$, $CH_2CH_2CH(OH)CH_2OH$, $CH_2I$, CH=$CH_2$, $CH_2CH$=$CH_2$ or $CH_2CH_2CH$=$CH_2$; wherein $R_5$=H; wherein $R_6$=$COCH_3$; and wherein $R_4$ is not H when $R_3$ is H or OH and wherein $R_4$ is not $NO_2$ or $NH_2$ when $R_3$ is H.

In yet another embodiment, the present invention provides a method of inhibiting influenza virus neuraminidase comprising the step of: administering to a subject a pharmaceutically acceptable amount of a composition comprising effective amounts of a pharmaceutically acceptable carder and a compound, its analogs, its pharmaceutically acceptable salts, derivatives, or mixtures thereof having the following formula:

GENERAL STRUCTURE I

[Structure: benzene ring with A, $R_1$, $R_2$, $R_3$, $R_4$, B, $R_5$, $R_6$]

wherein A=$CO_2H$, $CO_2CH_3$, $NO_2$, $SO_3H$ or $PO_3H_2$; wherein B=CH, N, O or S; wherein $R_1$ and $R_2$=H, $NO_2$ or $(CH_m)_nX_1$ where m=1 or 2, n is an integer from 0 to 4 and $X_1$=guanidino, OH, $NH_2$, SH, $NO_2$, F, Cl, Br, I, CN, $CF_3$, $CO_2H$, $SO_3H$ or $PO_3H_2$; wherein $R_3$ and $R_4$=H, $(CH_o)_pX_2$, $(CH_o)_pCHX_2CH_2X_2$, $NH(CH_o)_pCHX_2CH_2X_2$, $NHCO(CH_p)_pCH_2X_2$ or $NHCO(CH_o)_pCHX_2CH_2X_2$ where o=1 or 2, p is an integer from 0 to 4 and $X_2$= H, guanidino, OH, $NH_2$, SH, $NO_2$, $CF_3$, $CO_2H$, $SO_3H$ or $PO_3H_2$; wherein $R_5$=H, OH, $NH_2$, $(CH_k)_1X_3$, $CO(CH_k)_1X_3$, $SO(CH_k)_1X_3$ or $SO_2(CH_k)_1X_3$ where k=1 or 2, 1 is an integer from 0 to 4 and $X_3$=guanidino, OH, $NH_2$, SH, $NO_2$, $CF_3$, $CO_2H$, $SO_3H$ or $PO_3H_2$; and wherein $R_6$=H, $CH(OH)X_4$, $CH(NH_2)X_4$, $COX_4$, $SOX_4$, or $SO_2X_4$, where $X_4$=H, $CH_3$, $CH_3CH_2$, $CH_3CHCH_3$, $CH_3CH_2CH_2$ or halogen substituted analogs of $X_4$.

Also provided is a method of inhibiting influenza virus neuraminidase comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

GENERAL STRUCTURE I

[Structure: benzene ring with A, $R_1$, $R_2$, $R_3$, $R_4$, B, $R_5$, $R_6$]

wherein A=$CO_2H$ or $CO_2CH_3$; wherein B=CH or N; wherein $R_1$ and $R_2$ =H or $NO_2$; wherein $R_3$=H, OH, $NH_2$, guanidino, $NO_2$, F, Cl or Br; wherein $R_4$ =$QR_7$ where Q=O, NH or $CH_2$ and $R_7$=H, $(CH_2)_oX_1$, $(CH_2)_oCHX_1CH_2X_1$, $CO(CH_2)_oCH_2X_1$ or $CO(CH_2)_oCHX_1CHX_1$ wherein o is an integer from 0 to 4 and $X_1$ =H, guanidino, OH or $NH_2$; wherein $R_5$=$COCH_3$; and wherein $R_6$=$(CH_2)_pX_2$ where p is an integer from 0 to 4 and $X_2$=OH, $NH_2$ or guanidino.

The present invention provides a method of inhibiting influenza virus neuraminidase comprising the step of: administering to a subject a pharmaceutically acceptable amount of a composition comprising effective amounts of a pharmaceutically acceptable carder and a compound, its analogs, its pharmaceutically acceptable salts, derivatives, or mixtures thereof having the following formula:

GENERAL STRUCTURE I

[Structure: benzene ring with A, $R_1$, $R_2$, $R_3$, $R_4$, B, $R_5$, $R_6$]

wherein A=$CO_2H$ or $CO_2CH_3$; wherein B=N; wherein $R_1$=H or $NO_2$; wherein $R_2$=H or $NO_2$; wherein $R_3$=H, OH, $NO_2$, $NH_2$ or guanidino; wherein $R_4$=H, OH, OAc, $NH_2$, guanidino, $NHCOCH_2OH$, $NHCOCH(OH)CH_2OH$, $NHCOCH_2NH_2$, $NHCOCH_2CH_2CH_2NH_2$, CHO, $CH_2OH$, $CH_2OAc$, $CH_2CH_2OH$, $CH_2CH_2CH_2OH$, $CH_2CH(OH)CH_2OH$, $CH_2CH_2CH_2CH_2OH$, $CH_2CH_2CH(OH)CH_2OH$, $CH_2I$, CH=$CH_2$, $CH_2CH$=$CH_2$ or $CH_2CH_2CH$=$CH_2$; wherein $R_5$=H; and wherein $R_6$=$COCH_3$.

In yet another embodiment, the present invention provides a method of making a composition for inhibiting influenza virus neuraminidase, comprising the steps of admixing effective amounts of a pharmaceutically acceptable carrier with a compound, it analogs, its pharmaceutically acceptable salts, derivatives, or mixtures thereof, having the following formula:

GENERAL STRUCTURE I

[Structure: benzene ring with A, $R_1$, $R_2$, $R_3$, $R_4$, B, $R_5$, $R_6$]

wherein A=$CO_2H$, $CO_2CH_3$, $NO_2$, $SO_3H$ or $PO_3H_2$; wherein B=CH, N, O or S; wherein $R_1$ and $R_2$=H, $NO_2$ or $(CH_m)_nX_1$ where m=1 or 2, n is an integer from 0 to 4 and $X_1$=guanidino, OH, $NH_2$, SH, $NO_2$, F, Cl, Br, I, CN, $CF_3$, $CO_2H$, $SO_3H$ or $PO_3H_2$; wherein $R_3$ and $R_4$=H, $(CH_o)_pX_2$, $(CH_o)_pCHX_2CH_2X_2$, $NH(CH_o)_pCHX_2CH_2X_2$, $NHCO(CH_o)_pCH_2X_2$ or $NHCO(CH_o)_pCHX_2CH_2X_2$ where o=1 or 2, p is an integer from 0 to 4 and $X_2=$ H, guanidino, OH, $NH_2$, SH, $NO_2$, $CF_3$, $CO_2H$, $SO_3H$ or $PO_3H_2$; wherein $R_5=$H, OH, $NH_2$, $(CH_k)_lX_3$, $CO(CH_k)_lX_3$, $SO(CH_k)_lX_3$ or $SO_2(CH_k)_lX_3$ where k=1 or 2, l is an integer from 0 to 4 and $X_3=$guanidino, OH, $NH_2$, SH, $NO_2$, $CF_3$, $CO_2H$, $SO_3H$ or $PO_3H_2$; and wherein $R_6=$H, $CH(OH)X_4$, $CH(NH_2)X_4$, $COX_4$, $SOX_4$, or $SO_2X_4$, where $X_4=$H, $CH_3$, $CH_3CH_2$, $CH_3CHCH_3$, $CH_3CH_2CH_2$ or halogen substituted analogs of $X_4$.

A method of making a composition for inhibiting influenza virus neuraminidase, comprising the steps of admixing effective mounts of a pharmaceutically acceptable carder with a compound, it analogs, its pharmaceutically

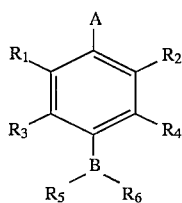

GENERAL STRUCTURE I wherein A=CO$_2$H or CO$_2$CH$_3$; wherein B=N; wherein R$_1$=H or NO$_2$; wherein R$_2$=H or NO$_2$; wherein R$_3$=H, OH, NO$_2$, NH$_2$ or guanidino; wherein R$_4$=H, OH, OAc, NH$_2$, guanidino, NHCOCH$_2$OH, NHCOCH(OH)CH$_2$OH, NHCOCH$_2$NH$_2$, NHCOCH$_2$CH$_2$NH$_2$, CHO, CH$_2$OH, CH$_2$OAc, CH$_2$CH$_2$OH, CH$_2$CH$_2$CH$_2$OH, CH$_2$CH(OH)CH$_2$OH, CH$_2$CH$_2$CH$_2$CH$_2$OH, CH$_2$CH$_2$CH(OH)CH$_2$OH, CH$_2$I, CH=CH$_2$, CH$_2$CH=CH$_2$ or CH$_2$CH$_2$CH=CH$_2$; wherein R$_5$=H; and wherein R$_6$=COCH$_3$. For this method, in preferable embodiments, the influenza virus infection is influenza virus type A infection. In addition, the influenza virus infection is influenza virus type B infection.

Further provided is a method of treating influenza virus infection comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

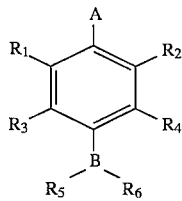

GENERAL STRUCTURE I wherein A=CO$_2$H, CO$_2$CH$_3$, NO$_2$, SO$_3$H or PO$_3$H$_2$; wherein B=CH, N, O or S; wherein R$_1$ and R$_2$=H, NO$_2$ or (CH$_m$)$_n$X$_1$ where m=1 or 2, n is an integer from 0 to 4 and X$_1$=guanidino, OH, NH$_2$, SH, NO$_2$, F, Cl, Br, I, CN, CF$_3$, CO$_2$H, SO$_3$H or PO$_3$H$_2$; wherein R$_3$ and R$_4$=H, (CH$_o$)$_p$X$_2$, (CH$_o$)$_p$CHX$_2$CH$_2$X$_2$, NH(CH$_o$)$_p$CHX$_2$CH$_2$X$_2$, NHCO(CH$_o$)$_p$CH$_2$X$_2$ or NHCO(CH$_o$)$_p$CHX$_2$CH$_2$X$_2$ where o=1 or 2, p is an integer from 0 to 4 and X$_2$= H, guanidino, OH, NH$_2$, SH, NO$_2$, CF$_3$, CO$_2$H, SO$_3$H or PO$_3$H$_2$; wherein R$_5$=H, OH, NH$_2$, (CH$_k$)$_1$X$_3$, CO(CH$_k$)$_1$X$_3$, SO(CH$_k$)$_1$X$_3$ or SO$_2$(CH$_k$)$_1$X$_3$ where k=1 or 2, 1 is an integer from 0 to 4 and X$_3$=guanidino, OH, NH$_2$, SH, NO$_2$, CF$_3$, CO$_2$H, SO$_3$H or PO$_3$H$_2$; and wherein R$_6$=H, CH(OH)X$_4$, CH(NH$_2$)X$_4$, COX$_4$, SOX$_4$, or SO$_2$X$_4$, where X$_4$=H, CH$_3$, CH$_3$CH$_2$, CH$_3$CHCH$_3$, CH$_3$CH$_2$CH$_2$ or halogen substituted analogs of X$_4$. In preferable embodiments, the influenza virus infection is influenza virus type A infection or influenza virus type B infection.

In yet another embodiment, the present invention provides a method of treating influenza virus infection comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

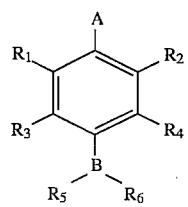

GENERAL STRUCTURE I wherein A=CO$_2$H or CO$_2$CH$_3$; wherein B=CH or N; wherein R$_1$ and R$_2$ =H or NO$_2$; wherein R$_3$=H, OH, NH$_2$, guanidino, NO$_2$, F, Cl or Br; wherein R$_4$ =QR$_7$ where Q=O, NH or CH$_2$ and R$_7$=H, (CH$_2$)$_o$X$_1$, (CH$_2$)$_o$CHX$_1$CH$_2$X$_1$, CO(CH$_2$)$_o$CH$_2$X$_1$ or CO(CH$_2$)$_o$CHX$_1$CH$_2$X$_1$ where o is an integer from 0 to 4 and X$_1$ =H, guanidino, OH or NH$_2$; wherein R$_5$=COCH$_3$; and wherein R$_6$=(CH$_2$)$_p$X$_2$ where p is an integer from 0 to 4 and X$_2$=OH, NH$_2$ or guanidino. In preferable embodiments, the influenza virus infection is influenza virus type A infection or influenza virus type B infection.

In yet another embodiment, the present invention provides a method of treating influenza virus infection comprising the step of: administering to a subject a pharmaceutically acceptable mount of a composition comprising effective mounts of a pharmaceutically acceptable carrier and a compound, its analogs, its pharmaceutically acceptable salts, derivatives, or mixtures thereof having the following formula:

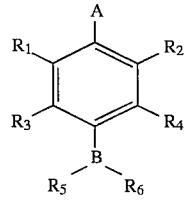

GENERAL STRUCTURE I wherein A=CO$_2$H or CO$_2$CH$_3$; wherein B=N; wherein R$_1$=H or NO$_2$; wherein R$_2$=H or NO$_2$; wherein R$_3$=H, OH, NO$_2$, NH$_2$ or guanidino; wherein R$_4$=H, OH, OAc, NH$_2$, guanidino, NHCOCH$_2$OH, NHCOCH(OH)CH$_2$OH, NHCOCH$_2$NH$_2$, NHCOCH$_2$CH$_2$NH$_2$, CHO, CH$_2$OH, CH$_2$OAc, CH$_2$CH$_2$OH, CH$_2$CH$_2$CH$_2$OH, CH$_2$CH(OH)CH$_2$OH, CH$_2$CH$_2$CH$_2$CH$_2$OH, CH$_2$CH$_2$CH(OH)CH$_2$OH, CH$_2$I, CH=CH$_2$, CH$_2$CH=CH$_2$ or CH$_2$CH$_2$CH=CH$_2$; wherein R$_5$=H; and wherein R$_6$=COCH$_3$. In preferable embodiments, the influenza virus infection is influenza virus type A infection or influenza virus type B infection.

Also provided is an influenza virus neuraminidase inhibitor, its analogs, its pharmaceutically acceptable salts, derivatives, and mixtures thereof having the following formula:

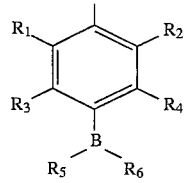

GENERAL STRUCTURE I wherein A=CO$_2$H; wherein B=N; wherein R$_1$=H; wherein R$_2$=H; wherein R$_3$=H; wherein R$_4$=OAc; wherein R$_5$=H; and wherein R$_6$=COCH$_3$.

An influenza virus neuraminidase inhibitor, its analogs, its pharmaceutically acceptable salts, derivatives, and mixtures thereof having the following formula:

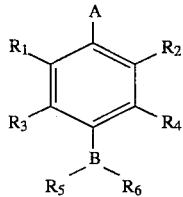

GENERAL STRUCTURE I wherein $A=CO_2H$; wherein $B=N$; wherein $R_1=NO_2$; wherein $R_2=NO_2$; wherein $R_3=H$; wherein $R_4=OH$; wherein $R_5=H$; and wherein $R_6=COCH_3$ is also provided.

In yet another embodiment, the present invention provides an influenza virus neuraminidase inhibitor, its analogs, its pharmaceutically acceptable salts, derivatives, and mixtures thereof having the following formula:

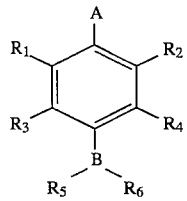

GENERAL STRUCTURE I wherein $A=CO_2H$; wherein $B=N$; wherein $R_1=H$; wherein $R_2=H$; wherein $R_3=NO_2$; wherein $R_4=OAc$; wherein $R_5=H$; and wherein $R_6=COCH_3$.

An influenza virus neuraminidase inhibitor, its analogs, its pharmaceutically acceptable salts, derivatives, and mixtures thereof having the following formula:

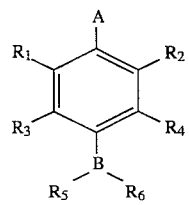

GENERAL STRUCTURE I wherein $A=CO_2H$; wherein $B=N$; wherein $R_1=H$; wherein $R_2=H$; wherein $R_3=NO_2$; wherein $R_4=OH$; wherein $R_5=H$; and wherein $R_6=COCH_3$ is provided.

Further provided is an influenza virus neuraminidase inhibitor, its analogs, its pharmaceutically acceptable salts, derivatives, and mixtures thereof having the following formula:

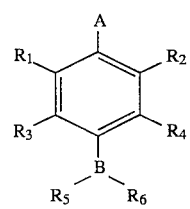

GENERAL STRUCTURE I wherein $A=CO_2H$; wherein $B=N$; wherein $R_1=H$; wherein $R_2=H$; wherein $R_3=NH_2$; wherein $R_4=OH$; wherein $R_5=H$; and wherein $R_6=COCH_3$.

Also provided is an influenza virus neuraminidase inhibitor, its analogs, its pharmaceutically acceptable salts, derivatives, and mixtures thereof having the following formula:

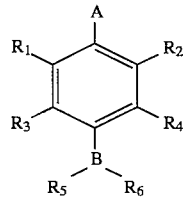

GENERAL STRUCTURE I wherein $A=CO_2H$; wherein $B=N$; wherein $R_1=H$; wherein $R_2=H$; wherein $R_3=H$; wherein $R_4=NHCOCH_2OH$, wherein $R_5=H$; and wherein $R_6=COCH_3$.

In yet another embodiment, the present invention provides an influenza virus neuraminidase inhibitor, its analogs, its pharmaceutically acceptable salts, derivatives, and mixtures thereof having the following formula:

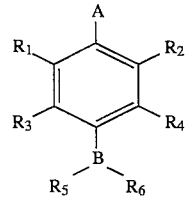

GENERAL STRUCTURE I wherein $A=CO_2H$; wherein $B=N$; wherein $R_1=H$; wherein $R_2=H$; wherein $R_3=H$; wherein $R_4=NHCOCH(OH)CH_2OH$; wherein $R_5=H$; and wherein $R_6=COCH_3$.

Further embodiments provide an influenza virus neuraminidase inhibitor, its analogs, its pharmaceutically acceptable salts, derivatives, and mixtures thereof having the following formula:

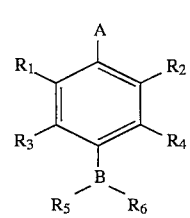

GENERAL STRUCTURE I wherein $A=CO_2H$; wherein $B=N$; wherein $R_1=H$; wherein $R_2=H$; wherein $R_3=H$; wherein $R_4=NHCOCH_2NH_2$; wherein $R_5=H$; and wherein $R_6=COCH_3$.

An influenza virus neuraminidase inhibitor, its analogs, its pharmaceutically acceptable salts, derivatives, and mixtures thereof having the following formula:

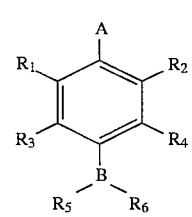

GENERAL STRUCTURE I wherein $A=CO_2H$; wherein $B=N$; wherein $R_1=H$; wherein $R_2=H$; wherein $R_3=H$; wherein $R_4=NHCO(CH_2)_3NH_2$; wherein $R_5=H$; and wherein $R_6=COCH_3$ is provided.

Further provided is an influenza virus neuraminidase inhibitor, its analogs, its pharmaceutically acceptable salts, derivatives, and mixtures thereof having the following formula:

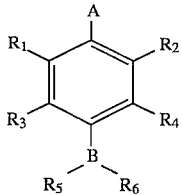

GENERAL STRUCTURE I wherein $A=CO_2H$; wherein $B=N$; wherein $R_1=H$; wherein $R_2=H$; wherein $R_3=H$; wherein $R_4=NHC(NH)NH_2$; wherein $R_5=H$; and wherein $R_6=COCH_3$.

Also provided is a method of inhibiting influenza virus neuraminidase comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

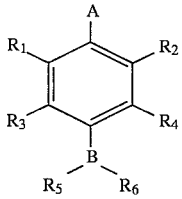

GENERAL STRUCTURE I wherein $A=CO_2H$; wherein $B=N$; wherein $R_1=H$; wherein $R_2=H$; wherein $R_3=H$; wherein $R_4=OH$; wherein $R_5=H$; and wherein $R_6=COCH_3$.

A method of inhibiting influenza virus neuraminidase comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

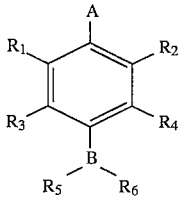

GENERAL STRUCTURE I wherein $A=CO_2H$; wherein $B=N$; wherein $R_1=H$; wherein $R_2=H$; wherein $R_3=H$; wherein $R_4=OAc$; wherein $R_5=H$; and wherein $R_6=COCH_3$ is also provided.

In yet another embodiment, the present invention provides a method of inhibiting influenza virus neuraminidase comprising the step of: administering to a subject a pharmaceutically acceptable amount of a composition comprising effective mounts of a pharmaceutically acceptable carrier and a compound, its analogs, its pharmaceutically acceptable salts, derivatives, or mixtures thereof having the following formula:

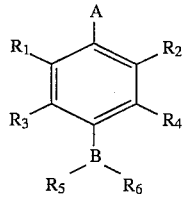

GENERAL STRUCTURE I wherein $A=CO_2H$; wherein $B=N$; wherein $R_1=NO_2$; wherein $R_2=NO_2$; wherein $R_3=H$; wherein $R_4=OH$; wherein $R_5=H$; and wherein $R_6=COCH_3$.

Further provided is a method of inhibiting influenza virus neuraminidase comprising the step of; administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

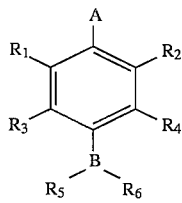

GENERAL STRUCTURE I wherein $A=CO_2H$; wherein $B=N$; wherein $R_1=H$; wherein $R_2=H$; wherein $R_3=NO_2$; wherein $R_4=OAc$; wherein $R_5=H$; and wherein $R_6=COCH_3$.

Also provided is a method of inhibiting influenza virus neuraminidase comprising the step of: administering to a subject a pharmaceutically acceptable amount of a composition comprising effective amounts of a pharmaceutically acceptable carder and a compound, its analogs, its pharmaceutically acceptable salts, derivatives, or mixtures thereof having the following formula:

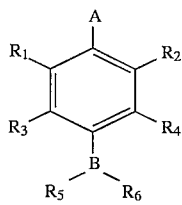

GENERAL STRUCTURE I wherein $A=CO_2H$; wherein $B=N$; wherein $R_1=H$; wherein $R_2=H$; wherein $R_3=NO_2$; wherein $R_4=OH$; wherein $R_5=H$; and wherein $R_6=COCH_3$.

The present invention provides a method of inhibiting influenza virus neuraminidase comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

GENERAL STRUCTURE I

[Structure: benzene ring with A at top, $R_1$ and $R_2$ on upper sides, $R_3$ and $R_4$ on lower sides, B attached at bottom with $R_5$ and $R_6$]

wherein A=$CO_2H$; wherein B=N; wherein $R_1$=H; wherein $R_2$=H; wherein $R_3$=$NH_2$; wherein $R_4$=OH; wherein $R_5$=H; and wherein $R_6$= $COCH_3$.

A method of inhibiting influenza virus neuraminidase comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

GENERAL STRUCTURE I

[Structure: benzene ring with A at top, $R_1$ and $R_2$ on upper sides, $R_3$ and $R_4$ on lower sides, B attached at bottom with $R_5$ and $R_6$]

wherein A=$CO_2H$; wherein B=N; wherein $R_1$=H; wherein $R_2$=H; wherein $R_3$=H; wherein $R_4$=$NO_2$; wherein $R_5$=H; and wherein $R_6$=$COCH_3$ is provided.

Also provided is a method of inhibiting influenza virus neuraminidase comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

GENERAL STRUCTURE I

[Structure: benzene ring with A at top, $R_1$ and $R_2$ on upper sides, $R_3$ and $R_4$ on lower sides, B attached at bottom with $R_5$ and $R_6$]

wherein A=$CO_2H$; wherein B=N; wherein $R_1$=H; wherein $R_2$=H; wherein $R_3$=H; wherein $R_4$=$NH_2$; wherein $R_5$=H; and wherein $R_6$=$COCH_3$.

A method of inhibiting influenza virus neuraminidase comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

GENERAL STRUCTURE I

[Structure: benzene ring with A at top, $R_1$ and $R_2$ on upper sides, $R_3$ and $R_4$ on lower sides, B attached at bottom with $R_5$ and $R_6$]

wherein A=$CO_2H$; wherein B=N; wherein $R_1$=H; wherein $R_2$=H; wherein $R_3$=H; wherein $R_4$=$NHCOCH_2OH$; wherein $R_5$=H; and wherein $R_6$ =$COCH_3$ is provided.

The instant invention provides a further method of inhibiting influenza virus neuraminidase comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

GENERAL STRUCTURE I

[Structure: benzene ring with A at top, $R_1$ and $R_2$ on upper sides, $R_3$ and $R_4$ on lower sides, B attached at bottom with $R_5$ and $R_6$]

wherein A=$CO_2H$; wherein B=N; wherein $R_1$=H; wherein $R_2$=H; wherein $R_3$=H; wherein $R_4$=$NHCOCH(OH)CH_2OH$; wherein $R_5$=H; and wherein $R_6$=$COCH_3$.

Also provided is a method of inhibiting influenza virus neuraminidase comprising the step of: administering to a subject a pharmaceutically acceptable amount of a composition comprising effective amounts of a pharmaceutically acceptable earlier and a compound, its analogs, its pharmaceutically acceptable salts, derivatives, or mixtures thereof having the following formula:

GENERAL STRUCTURE I

[Structure: benzene ring with A at top, $R_1$ and $R_2$ on upper sides, $R_3$ and $R_4$ on lower sides, B attached at bottom with $R_5$ and $R_6$]

wherein A=$CO_2H$; wherein B=N; wherein $R_1$=H; wherein $R_2$=H; wherein $R_3$=H; wherein $R_4$=$NHCOCH_2NH_2$; wherein $R_5$=H; and wherein $R_6$ =$COCH_3$.

The present invention provides a method of inhibiting influenza virus neuraminidase comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

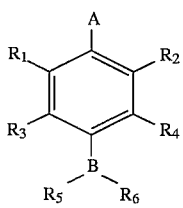

GENERAL STRUCTURE I wherein A=$CO_2$H; wherein B=N; wherein $R_1$=H; wherein $R_2$=H; wherein $R_3$=H; wherein $R_4$=NHCO$(CH_2)_3NH_2$; wherein $R_5$=H; and wherein $R_6$=COCH$_3$.

Finally, a method of inhibiting influenza virus neuraminidase comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

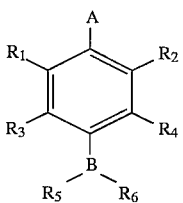

GENERAL STRUCTURE I wherein A=$CO_2$H; wherein B=N; wherein $R_1$=H; wherein $R_2$=H; wherein $R_3$=H; wherein $R_4$=NHC(NH)$NH_2$; wherein $R_5$=H; and wherein $R_6$ =COCH$_3$ is provided.

DETAILED DESCRIPTION OF THE INVENTION

Figure 1:
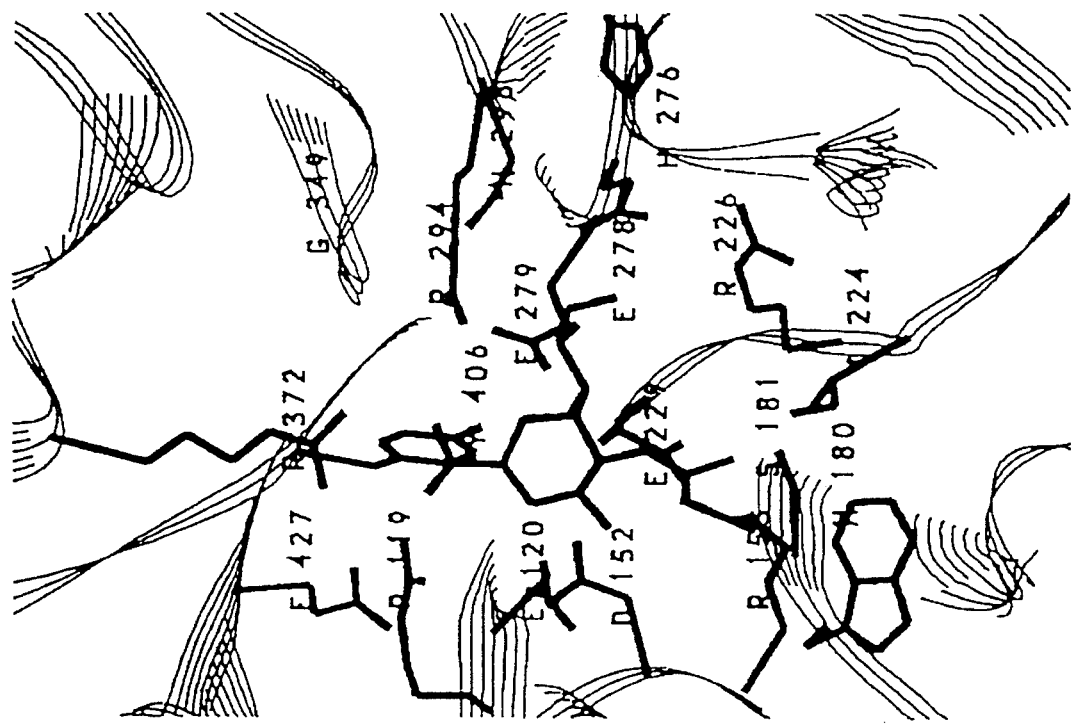
FIG. 1 shows a stereoview of the sialic acid binding site of the N9 NA-DANA complex.
Figure 1:
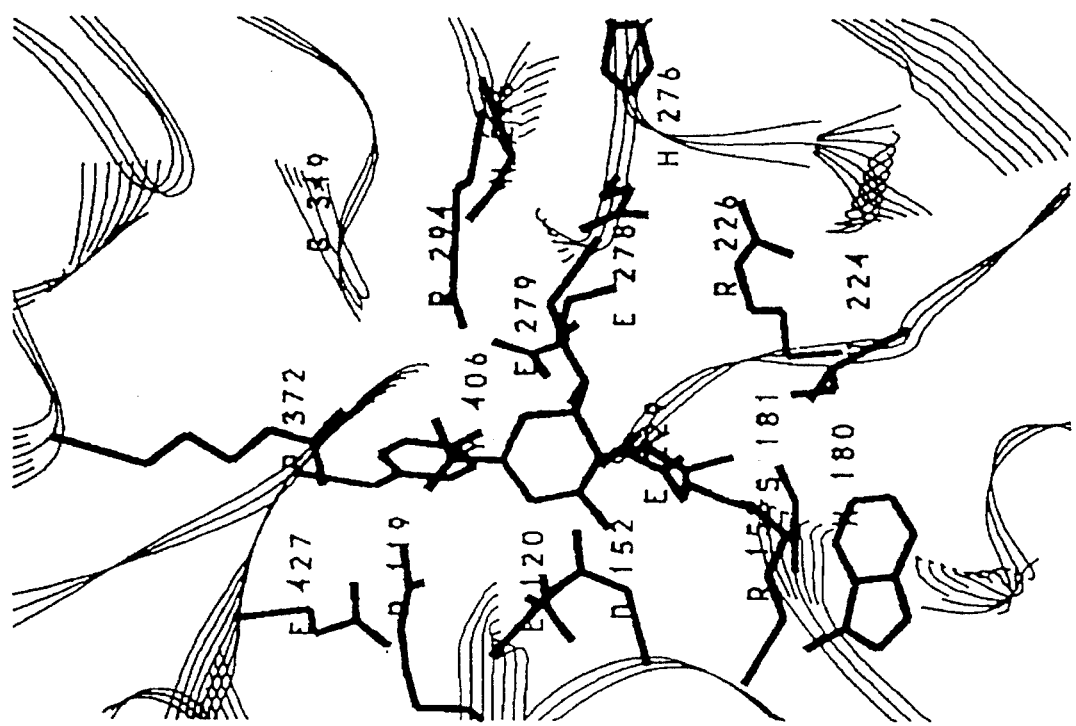
Figure 2:
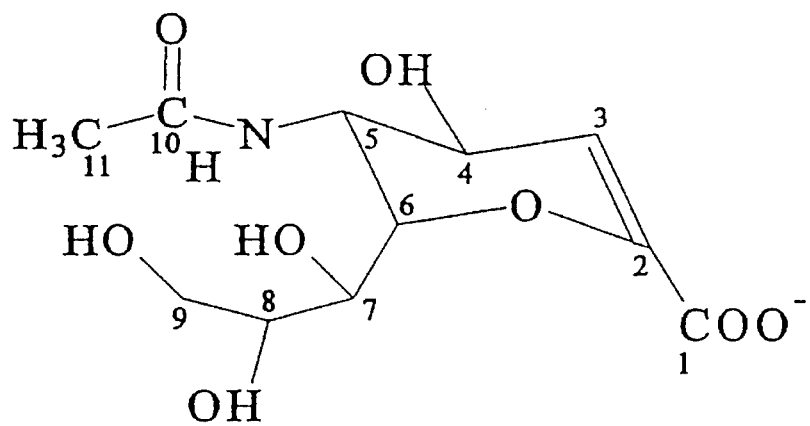
FIG. 2 is a listing of the amino acid contact between N9 NA and DANA.
Figure 3:
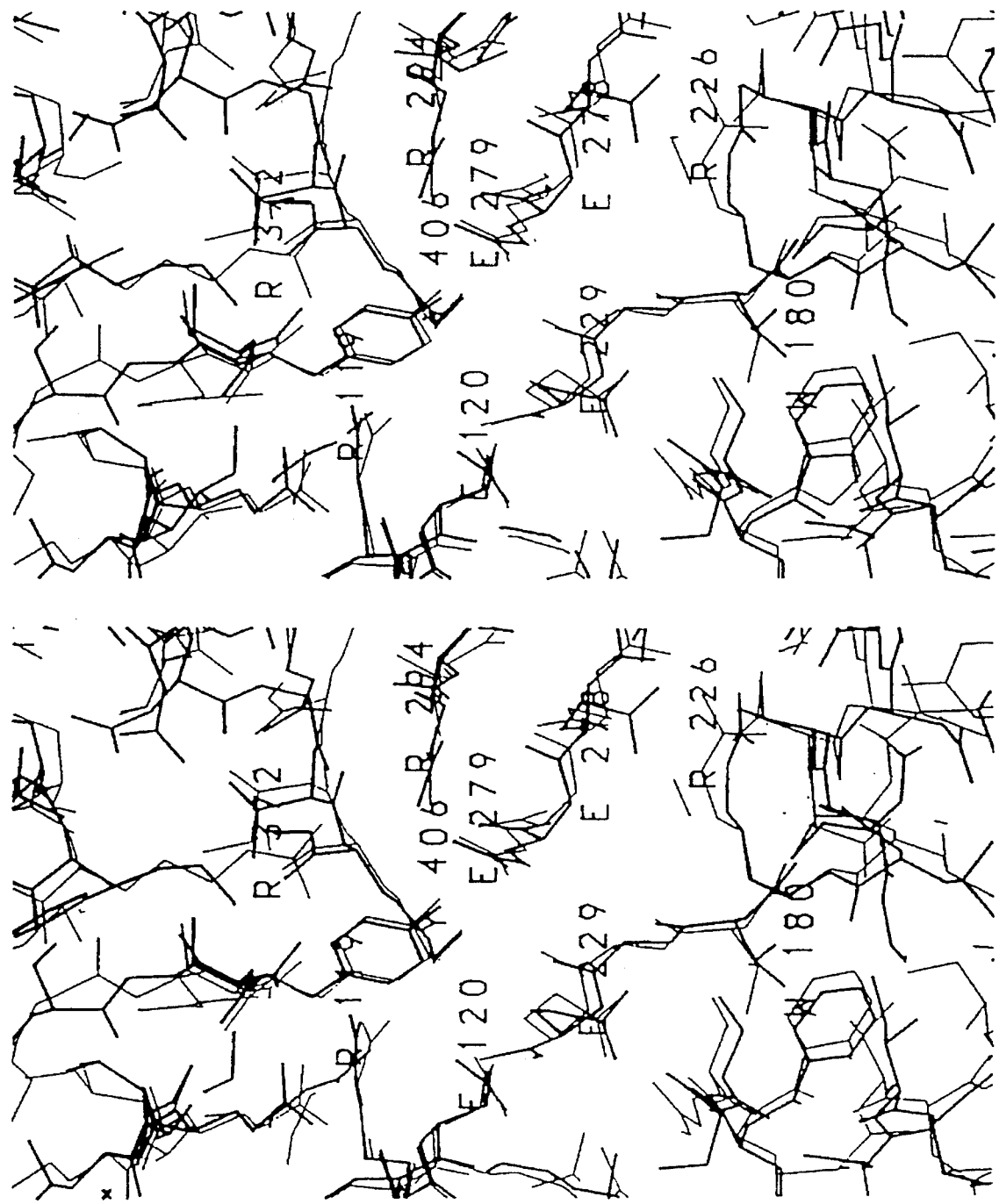
FIG. 3 shows a stereoview of the superimposition of the active sites for sialic add binding for N9 vs. B/Beijing NA (Bossart-Whitaker et. al., 1993).
Figure 4:
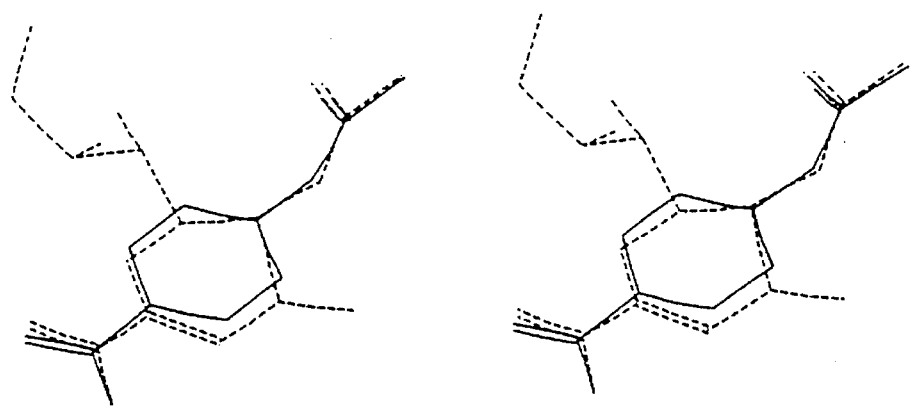
FIG. 4 shows a stereoview of the superimposition of DANA (broken lines, bound conformation) and N-acetyl-4-aminobenzoic acid (solid lines).

Structure-based drug design (for reviews, see Appelt et. al., 1991; Erickson and Fesik, 1992) has become an exciting new approach to drug development as a result of recent advances in x-ray crystallography and NMR methods, computer graphics software, computational methods, and computer hardware during the last decade. The most common variant of this approach uses x-ray crystallography to obtain a detailed, atomic-resolution structure for the macromolecular target (usually a protein). In favorable cases, ligands can be diffused into the active site of the protein crystal, or in less favorable cases the protein-ligand complex can be formed by co-crystallization, to provide by difference electron density maps the coordinates for bound ligand. Protein structures may thus be used for de novo design (new ligands are designed to bind to native protein), iterative design (the systematic modification of a lead ligand to improve its biological activity), or a posteriori analysis (the rationalization of existing SAR or a series of compounds).

The iterative design process (which by nature includes aspects of de novo and a posteriori design) has been successfully employed to develop ligands with significantly enhanced activities for a number of protein targets (for example, Erickson et. al., 1990; Varney et. al., 1992; Montgomery et al., 1993; Webber et. al., 1993). Additionally, x-ray crystallography has been employed to assist the design of numerous antiviral agents (see Laver and Air, 1990). The current invention targets influenza NA.

Highly-refined x-ray crystal structures for influenza virus NA's were first determined. These reveal that the sialic acid binding site in NA is highly conserved among the influenza A and B viruses. Furthermore, site-specific mutations of the conserved amino acids inactivate the enzyme. NA thus provides an attractive target for the design of broad spectrum anti-influenza agents.

In preliminary studies, the strum of a type A and type B NA bound to 2 -deoxy-2,3-dehydro-N-acetylneuraminic acid (DANA), a known inhibitor ($K_i$=10 μM) were determined.

In Vitro Evaluation for Inhibitory Actions on Neuraminidase

A preliminary screen uses whole virus as a source of neuraminidase, and 4 -methylumbelliferyl-N-acetyineuraminic acid (MUN) and fetuin as substrates. Then relative IC$_{50}$ values are determined. Compounds exhibiting activity greater than that for N-acetylneuraminic acid (NANA or sialic acid, a modest product inhibitor; IC$_{50}$ =10 mM) can then be more carefully evaluated. For the latter, purified influenza A and B neuraminidases, with the better-defined trisaccharide substrate N-acetylneuraminyl lactose, are used under Michaelis-Menton conditions to determine $K_i$ values. Compounds with $K_i$'s less than 100 μM will then be tested for inhibitory effects on viral replication in whole cells using the Madin-Darby canine kidney (MDCK) cell line, by measuring the effect of the inhibitor on virus yield (tissue-culture infectious dose). The cytotoxicity (cell viability) of inhibitors is then evaluated in MDCK cells spectrophotometrically using a metabolizable tetrazolium dye. Effects of compounds on rates of protein synthesis and cell division in treated cells would also be determined. The above protocol would be recognized and easily practiced by those skilled in the art.

Determination of the X-ray Crystal Structure of Inhibitor-Neuraminidase Complexes X-ray crystal structure determination of candidate inhibitors bound to NA was accomplished by diffusion of the synthetic ligand into protein crystals of types A and B NA's. Then difference density maps were used to obtain coordinates for the bound ligand. This step determined if ligand orientation was as expected and how the ligand interacted with conserved amino acid residues. These structures revealed that simple benzenoid structures containing the p-oriented acetamido and carboxylic acid moieties bound specifically to and oriented properly in the sialic acid binding site of NA.

Although the present invention has been described with reference to specific details of certain embodiments thereof, it is not intended that such details should be regarded as limitations upon the scope of the invention except as and to the extent that they are included in the accompanying claims.

EXAMPLES

A. Protein Crystals and Highly Refined X-ray Crystal Structures for Different Neuraminidases Disclosed herein are refined x-ray crystal structures of N9 and influenza B/Lee/40 NA, both as the native protein and the complex with DANA. In addition, another group has determined the structure for NA of B/Beijing (Burmeister et. al., 1992). Also, the coordinates of the N2 structure reported in 1983 were known (as of October, 1992). The sialic acid binding site is highly conserved among the various neuraminidases. Thus crystals and coordinates for three different neuraminidase-DANA complexes are disclosed herein.

Next, the native three-dimensional structure of neuraminidase from influenza virus A/Tern/Australia/G70c/75 (N9) was determined by the method of multiple isomorphous replacement (refined to 2.5 Å resolution) (Bossart-Whitaker et. al., 1993) and the inhibitor complex with DANA was also determined (refined to 2.8 Å resolution) (Bossart-Whitaker et al., 1993). The pronase-released NA head retains full enzymatic and antigenic activity and is a box-shaped tetramer with edge lengths of 90 Å and a maximal depth of 60 Å. The tetramer contains crystallographically equivalent monomers related by circular 4-fold symmetry. The secondary structure is 50% beta sheet, and the remaining residues form 24 strand-connecting loops or turns (one loop contains a small α-helix). For the DANA complex, the center of mass for the bound inhibitor is 32 Å from the 4-fold axis of the tetramer, lodged at the end of a shallow crater with 16 Å diameter and a depth of 8–10 Å. Twelve amino acid residues directly bind DANA, and six additional conserved amino acids line the active site pocket. The residues of the active site form an extensive array of hydrogen bonds which maintain a surprisingly rigid binding site. When the native site is compared to the DANA complex, only two residues have shifted. These are two arginines (Arg 294 and Arg 372), which are involved in interactions with the carboxylate oxygens on DANA, toward which they move slightly. Shown in FIG. 1 is a stereoview for the sialic acid binding site of the N9 NA - DANA complex and a listing (see FIG. 2) of amino acid contacts with DANA. (Bossart-Whitaker et al., 1993). Note that NANA (sialic acid) undergoes essentially the same interactions as DANA when bound to NA (Varghese et. al., 1992).

Similarly, the crystal structure of a type B neuraminidase, B/Lee/40, has also been determined (Janakiraman et. al., 1994). The native structure and the structure of the complex with DANA were refined to 1.8 Å resolution. Higher resolution structures allow for more critical evaluation of ligand orientation in the binding site, ligand-protein interactions, and the movement of amino acid residues in the protein when different ligands are bound.

The structure of A/Tokyo/67 (N2) neuraminidase in a crystal form of $C222_1$ has also been solved.

Finally, although sequence identity between neuraminidases of influenza A and B viruses is less than 30%, the three-dimensional arrangements for the conserved active site residues are nearly identical. This is illustrated by a superimposition of the active sites for neuraminidase from influenza A N9 and B/Beijing shown in FIG. 3 [Sialic Acid Binding Site for N9 vs. B/Beijing NA (Bossart-Whitaker et. al., 1993)].

B. Neuraminidase-Deficient Mutant

The neuraminidase-deficient mutant of the reassortant influenza virus A/NWS/$33_{HA}$-A/tern/Australia/GC70c/$75_{NA}$ (H1N9) was selected by passaging virus in Madin-Darby canine kidney (MDCK) cells in a medium containing neuraminidase from the bacterium *Micromonospora viridifaciens* and polyclonal antiserum against the influenza NA. Growth of the resulting mutant is dependent upon the addition of neuraminidase to the medium. Western blot analysis showed that the neuraminidase protein was absent from the mutant virus particles, and Northern hybridization showed that RNA segment 6, which codes for neuraminidase, had undergone massive deletion such that the only coding capacity is for the transmembrane sequence (Liu and Air, 1993).

C. Design of Benzenoid Inhibitors

2-Deoxy-2,3-didehydro-N-acetylneuraminic acid (DANA) is a known good inhibitor ($K_i$=4×$10^{-6}$M) for influenza A neuramidase (Taylor & von Itzstein, 1994). Evaluation of the interactions between DANA and the sialic acid binding site on neuraminidase reveal that, among the side chains found on the ring of DANA, the carboxylate most strongly associates with the binding site via 4 interactions to three different arginine residues (N2 numbering: Arg 118, 292, and 371). Additionally, the N-acetyl group is the only substituent which occupies a hydrophobic pocket (interactions of methyl with Ile 222 and Trp 178, along with other interactions of the amide carbonyl oxygen with Arg 152 and the amide nitrogen with an ordered water).

For the DANA-neuraminidase complex, the plane of the N-acetyl amide is oriented perpendicular to the plane of, and bisects the O—C═O bond of, the carboxylate. This produces an amide N to C1 distance of 5.51 Å, and an amide O to C1 distance of 6.20 Å.

All known good inhibitors of influenza neuraminidase are carbohydrate derivatives containing the pyran ring, and most are structurally similar to DANA. As drugs, these compounds suffer from potential problems including lack of oral activity, metabolic lability, complicated stereochemistry, difficulty in synthesis and excessive conformational flexibility. The present invention, however, describes simpler noncarbohydrate compounds containing the carboxylate and the N-acetyl groups, or alternative groups that can undergo similar interactions with the binding site, attached to a cyclic backbone "spacer". The cyclic spacer correctly orients the general groups or alternative side chain groupings to provide new classes of neuraminidase inhibitors for further elaboration.

The benzene ring spacer has inherently simple stereochemistry (i.e., no chiral carbons occur at side chain to ring branches), relative conformational rigidity (the predicted positioning of side chain functionality is simplified), relative ease of synthesis, and prospects for oral activity and good metabolic disposition (many useful drugs are based upon benzene).

D. Synthesis of Benzenoid Inhibitors

Figure 5:
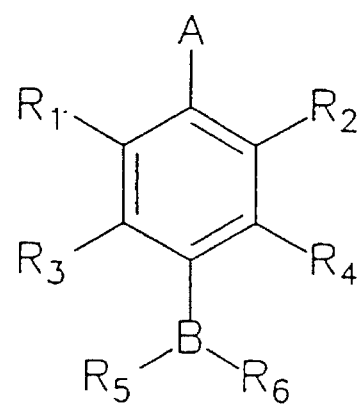
FIG. 5 shows the general structure of the class of compounds described herein and referred to as General Structure I.

Compounds with General Structure I (See FIG. 5) and their pharmaceutically acceptable salts and derivatives, may be prepared using any of several methods known in the art for the synthesis of substituted benzenoid compounds containing analogous structures.

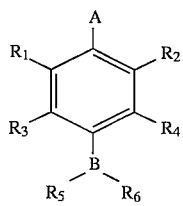

GENERAL STRUCTURE I

To illustrate, potential synthetic approaches for selected examples from General Structure I (Table 15) are summarized in the following two reaction schemes and are representative of the types of procedures to be employed. Table 12 listed the compounds successfully synthesized to date.

TABLE 12

| Compound | $R_1$ | $R_2$ | $R_3$ | $R_4$ |
|---|---|---|---|---|
| 101 | H | H | H | OH |
| 102 | H | H | H | OAc |
| 103 | $NO_2$ | $NO_2$ | H | OH |
| 104 | H | H | $NO_2$ | OAc |
| 105 | H | H | $NO_2$ | OH |
| 106 | H | H | $NH_2$ | OH |
| 107 | H | H | H | $NO_2$ |
| 108 | H | H | H | $NH_2$ |
| 109 | H | H | H | $NHCOCH_2OH$ |
| 110 | H | H | H | $NHCOCH(OH)CH_2OH$ |
| 111 | H | H | H | $NHCOCH_2NH_2$ |
| 112 | H | H | H | $NHCO(CH_2)_3NH_2$ |
| 113 | H | H | H | $NHC(NH)NH_2$ |

Table 15 proposes constructing a basic skeleton of General Structure I via formylation ortho to the acetylamino group. This could be accomplished using Friedel-Crafts alkylation with dichloromethyl methyl ether, which has been shown to be a general method for the formylation of numerous substituted benzenes [(A. Rieche et. al., *Chem. Ber*, 93, 88–94 (1960)]. As illustrated here, the o-formylation of 14 will provide target 24 (via intermediate 23), and the o-formylation of 25–27 will provide precursors 28–30 for the further elaboration to additional targets.

TABLE 15

Scheme for Synthesizing Benzenoid Candidate Inhibitors

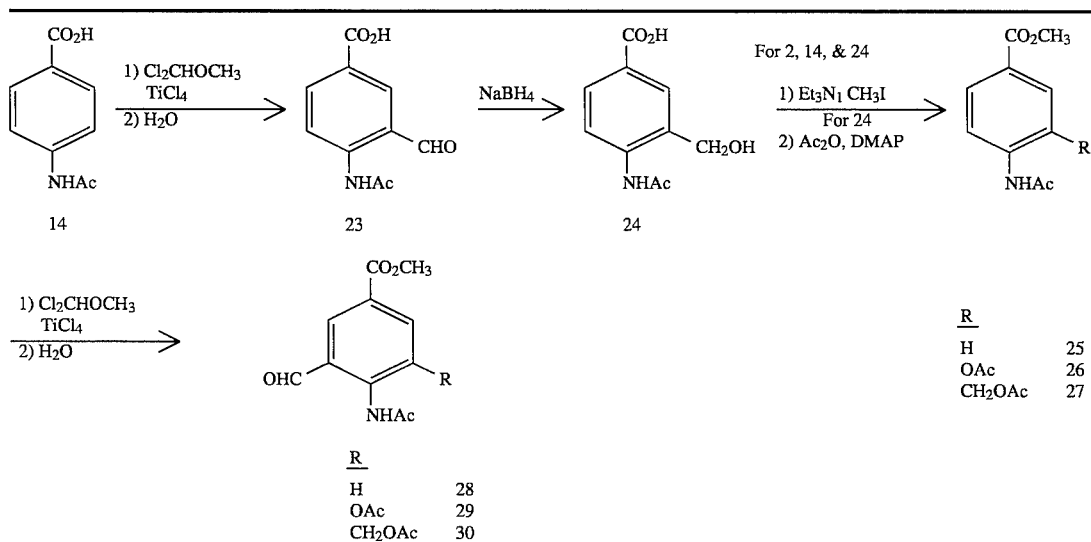

PATHWAY A:

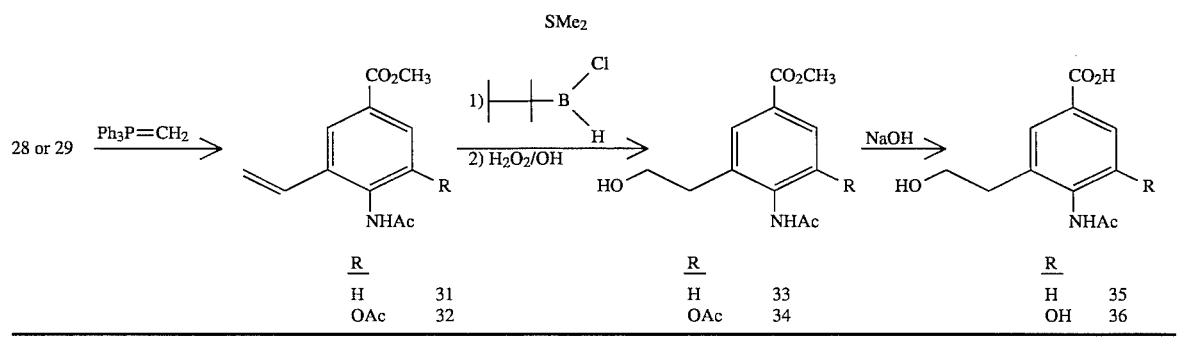

This key o-formylation step occurs early in the proposed syntheses, and if unexpected difficulties am encountered, several alternatives are possible. These include: (a) Other o-formylation methods could be employed, such as the o-formylation of anilines via the rearrangement of azasulfonium salts [P. Gassman and H. Drewes, *J. Am. Chem. Soc.*, 100, 7600–7610 (1978)], which has been used for the synthesis of substituted o-acetylamino-benzaldehydes. (b) Since the acetylamino group is a good "directed metalation group" (V. Snieckus, *Chem. Rev.*, 90, 879–933 (1990)], it is possible to regioselectively o-lithiate suitable derivatives of 14 and 25– 27. Reaction with appropriate electrophiles (epoxides, alkyl halides, aldehydes, etc.) would then provide an entry into desired targets. (c) The o-iodination of protected 14 and 25–27 could be employed in anticipation of a Heck-type coupling reaction [Y. Hatanaka et. al., *J. Am. Chem. Soc.*, 113, 7075–7076 (1991); K. Nilsson et. al., *J. Org. Chem.*, 57, 4015–4017 (1992)] to introduce o-substituents. Pathway A describes the proposed elaboration of precursors 28 and 29 to final products. Wittig olefination of the benzaldehydes will provide 31 and 32, and hydroboration-oxidation using thexylchloroborane [H. Brown et. al., *J. Org. Chem.*, 45, 4540–4542 (1980)] will provide hydroxyethyl derivatives 33 and 34. Basic hydrolysis of the esters then provides targets 35 and 36.

A similar procedure is proposed in Pathway B (Table 16) for the formation of additional targets. In this procedure 28–30 undergo conversion to iodomethyl derivatives 37–39, which are coupled with two different lithium dialkyl cuprates [G. Posner, *Org. React.*, 22, 253–400 (1975)] to provide 40–44. Glycol formation using N-methylmorpholine-N-oxide and catalytic $OsO_4$ [N. Iwasa et. al., *Chem. Lett.*, 721–1724 (1988)], or hydroboration as in Pathway A, followed by basic hydrolysis, then provides the final products 45–53.

TABLE 16

Scheme for Synthesizing Benzenoid Candidate Inhibitors

PATHWAY B:

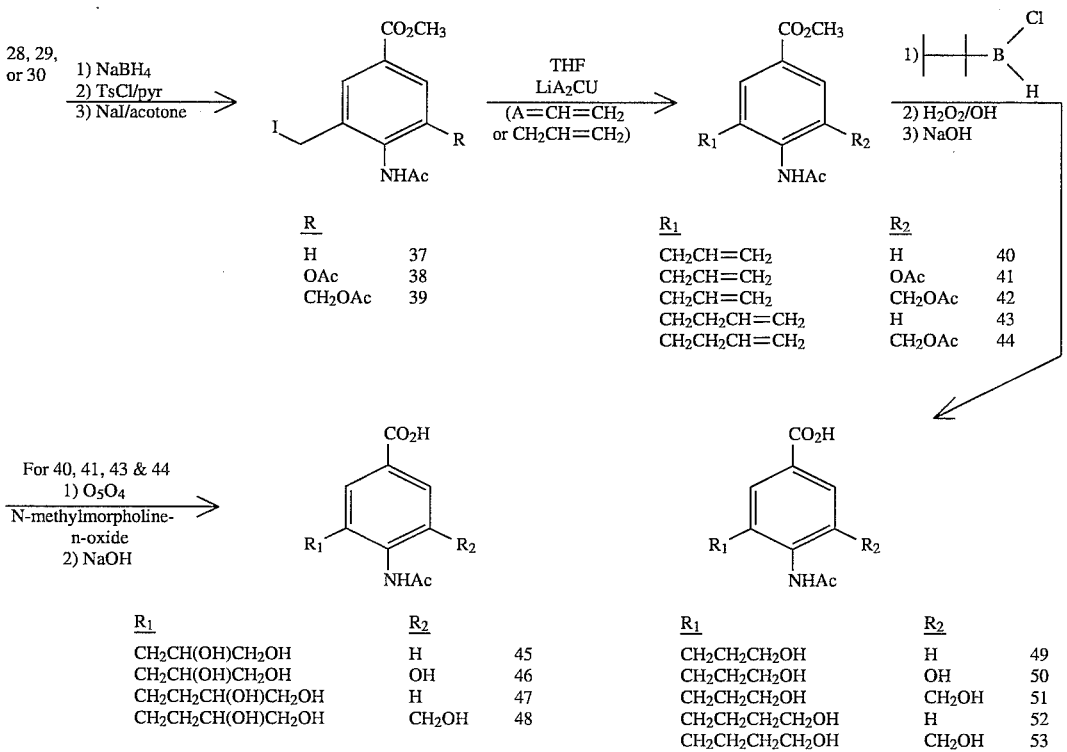

The following detailed examples for methods of preparation are for illustration only, and are not intended to represent a limitation of the invention. The structures of the compounds whose preparations are described below are summarized in Table 12. In all cases synthetic intermediates and products were found to be pure according to standards known to those skilled in the art (such as thin layer chromatography, melting or boiling points, gas chromatography, ion exchange chromatography, and/or high pressure liquid chromatography, elemental analysis, and spectroscopic methods). Furthermore, structures were characterized and fully assigned by spectroscopic methods considered standard practices by those skilled in the art (such as infrared, ultraviolet, and mass spectroscopies, $^1$H and $^{13}$C nuclear magnetic resonance spectroscopy, and/or x-ray crystallography). Selected spectral data are described for intermediates and products.

Three of the following products have been described previously in the literature, although the methods of preparation employed below have not been previously reported. Compound 101 was described as a metabolite of benoxinate (Kasuya, et. al., 1987). Compounds 107 and 108 were synthesized by other methods (Verma and Kahn, 1978; Ellis and Jones, 1974). None of these products have been suggested in methods as described herein.

EXAMPLE

The preparations of 4-(acetylamino)-3-hydroxybenzoic acid (101) and 4-(acetylamino)-3-acetoxybenzoic acid (102). The overall reaction scheme is shown in Table 17.

TABLE 17

Reaction Paths and the Chemical Structures of Compounds 13, 102 and 101

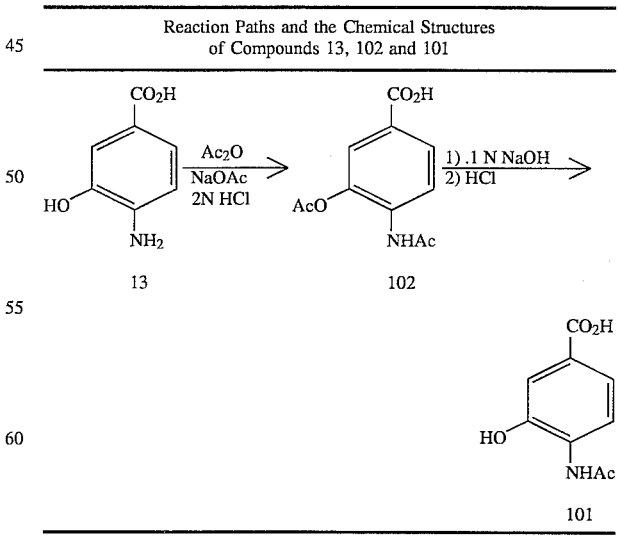

Preparation of 4-(Acetylamino)-3-Hydroxybenzoic Acid (101)

A solution of 102 (100 mg, 0.42 mmol) in 0.1N NaOH (5 mL) was stirred at room temperature for 30 minutes. Concentrated HCl was added dropwise to adjust the mixture to pH 2, and this was extracted with ethyl acetate (2×10 mL). The extracts were dried ($Na_2SO_4$), concentrated to dryness on a rotary evaporator, and the solid residue was washed out of the flask with dry hexane and filtered to give 101 (40 mg, 49% yield): mp 249°–250 C.

$^1$H NMR (DMSO-$d_6$) 2.13 (s, 3 H, $COCH_3$), 7.37 (dd, 1 H, aromatic, J=8 & 1.8 Hz), 7.44 (d, 1 H, aromatic, J=1.8 Hz), 8.01 (d, 1 H, aromatic, J=8 Hz), 9.26 (s, 1 H, NH).

Preparation of 3-Acetoxy-4-(Acetylamino)Benzoic Acid (102)

To a stirred solution of commercially available compound 13 (0.50 g, 3.3 mmol) in 2N HCl (10 mL) at 0° C. (ice bath) was added a solution of NaOAc (5.0 g, 61 mmol) in water (25 mL). To this was added $Ac_2O$ (5.4 g, 53 mmol). The mixture was stirred at 0° C. for 5 minutes, and it was then allowed to warm slowly to room temperature as the ice bath melted. After 4 hours a light brown precipitate had formed. This was filtered, washed with water (25 mL), and air-dried to provide 4-(acetylamino)-3-acetoxybenzoic acid (102; 450 mg, 58% yield): mp 219°– 221° C. ($CH_3OH/H_2O$).

$^1$H NMR (DMSO-$d_6$) 2.17 (s, 3 H, $COCH_3$), 2.35 (s, 3 H, $COCH_3$), 7.69 (d, 1 H, aromatic, J=1.8 Hz), 7.79 (dd, 1 H, aromatic, J=7 & 1.8 Hz), 8.17 (d, 1 H, aromatic, J=7 Hz), 9.3 (s, 1 H, NH).

EXAMPLE

The preparations of 4-(acetylamino)-3-hydroxy-2,6-dinitrobenzoic acid (103), 3-acetoxy-4-(acetylamino)-5-nitrobenzoic acid (104), 4-(acetylamino)-3-hydroxy-5-nitrobenzoic acid (105), and 3-amino-4-(acetylamino)-5-hydroxybenzoic acid, hydrochloride (106). The overall reaction scheme is shown in Table 18.

Preparation of 4-(Acetylamino)-3-Hydroxy-2,6-Dinitrobenzoic Acid (103)

3-Acetoxy-4-(acetylamino)benzoic acid (102; 2.00 g, 8.43 mmol) was added gradually to a paste made from concentrated $H_2SO_4$ (8.5 mL) and potassium nitrate (2.22 g, 22.0 mmol) at −10°–0° C. The reaction was stirred at 0° C. for 30 minutes, and the syrupy mass was poured onto cracked ice. After standing for one hour a yellow solid separated. This was filtered, washed on the filter with cold water, and air-dried to give 103 (1.60 g, 66.7% yield): mp 199°–203° C. (ethyl acetate/hexane).

$^1$H NMR (DMSO-$d_6$) 2.16 (s, 3 H, $NCOCH_3$), 8.73 (s, 1 H, aromatic), 9.72 (s, 1 H, NH).

Preparation of 3-Acetoxy-4-(Acetylamino)-5-Nitrobenzoic Acid (104)

Compound 102 (1.00 g, 4.21 mmol) was suspended with stirring in a mixture of $Ac_2O$ (8.33 mL, 8.99 g, 88.2 mmol) and dioxane (6.6 mL). This was cooled to 0° C., and a cold solution of the nitrating mixture made from $Ac_2O$ (3.33 mL, 3.59 g, 35.2 mmol) and concentrated $HNO_3$ (3.33 mL) was slowly added to the mixture containing 102. The reaction mixture was then warmed to 30°–35° C. until the reaction was complete as evidenced by TLC. The reaction mixture was poured onto ice/water (100 mL), extracted with EtOAc (4×50 mL), dried ($NaSO_4$), and concentrated to dryness on a rotary evaporator to give crude 104 (1.05 g, 89.9%) as an oil. Trituration with $CHCl_3$ gave a solid: mp 196°–201° C. (dioxane/hexane).

$^1$H NMR ($CD_3OD$) 8.42–8.33 (d, J=1.5 Hz, 1 H, aromatic), 8.05–8.12 (d, J=1.5 Hz, 1 H, aromatic), 2.35 (s, 3 H, $OCOCH_3$), 2.13 (s, 3 H, $NCOCH_3$).

Preparation of 4-(Acetylamino)-3-Hydroxy-5-Nitrobenzoic Acid (105)

Compound 104 (0.850 g, 3.54 mmol) was dissolved in 0.1N NaOH (80 mL), and the mixture was stirred at room temperature for 4 hours. This was acidified with concentrated HCl (2 mL), diluted with water (20 mL), and extracted with ethyl acetate (3×60 mL). The combined extracts were dried ($Na_2SO_4$) and concentrated on a rotary evaporator to give crystalline 105 (0.712 g, 98.4% yield): mp 256°–259 ° C (methanol).

TABLE 18

Reaction Paths and the Chemical Structures of Compounds 102, 103, 104, 105 and 106

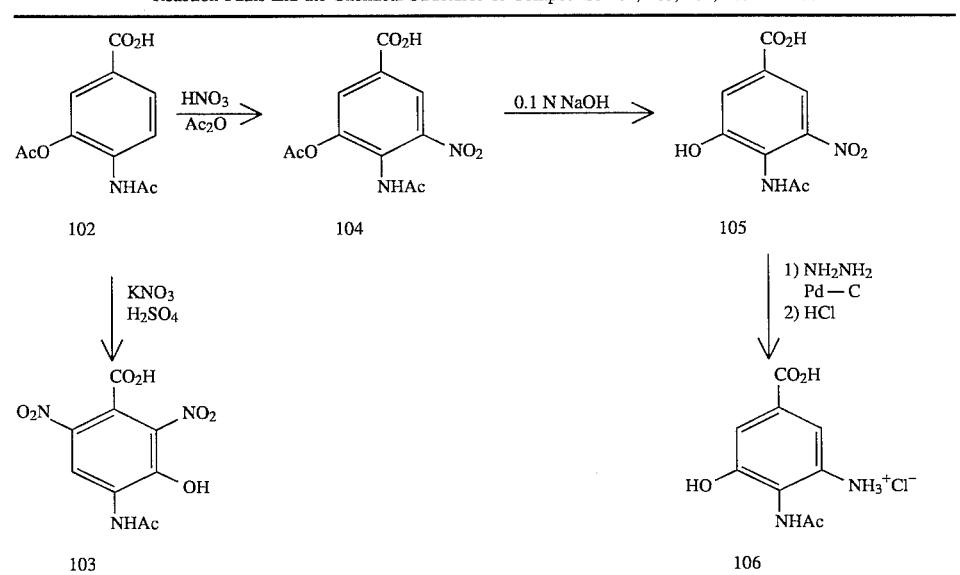

$^1$H NMR (DMSO-$d_6$) 10.93 (s, 1H, COOH), 9.90 (s, 1H, NH), 7.79–7.69 (m, 3 H, aromatic), 2.04 (s, 3 H, $NCOCH_3$).

Preparation of 3-Amino-4-(Acetylamino)-5-Hydroxybenzoic Acid, Hydrochloride (106)

Compound 105 (100 mg, 0.416 mmol) was dissolved in ethanol (3 mL), and Pd-C (100 mg) was added to it. To this mixture was added hydrazine hydrate (55% hydrazine, 0.10 mL, 55 mg, 1.7 mmol) dropwise. The reaction mixture was heated at reflux for 1 hour. The Pd-C was filtered and the ethanol was concentrated under vacuum to give the free amine of 106 as a pale yellow oil (85 mg, 97% yield). The oil was dissolved in ethanol (3 mL), HCl (gas) was bubbled through the solution for a few minutes, and ether (10 mL) was added. No precipate formed, so the solution was concentrated to dryness to give 106 (100 mg) as the hydrochloride salt: mp 220 ° C. (dec).

$^1$H NMR ($D_2O$) 7.45–7.40 (m, 2 H, aromatic), 2.22 (s, 3 H, NCOCH$_3$).

EXAMPLE

The preparations of 4-(acetylamino)-3-hydroxy-5-nitrobenzoic acid (107), 4 -(acetylamino)-3-aminobenzoic acid (108), and 4-(acetylamino)-3-guanidinobenzoic acid (113). The overall reaction scheme is shown in Table 19.

TABLE 19

Reaction Paths and the Chemical Structures of Compounds 14, 107, 108 and 113

[Structure: 14 (4-acetylaminobenzoic acid) → KNO$_3$/H$_2$SO$_4$ → 107 (with NO$_2$ group) → NH$_2$NH$_2$/Pd/C/EtOH → 108 (with NH$_2$ group) → NH$_2$CN/80 → 113 (with NHCNH$_2$, NH group)]

Preparation of 4-(Acetylamino)-3-Hydroxy-5-Nitrobenzoic Acid (107)

Commercially available compound 14 (5.00 g, 27.9 mmol) was gradually stirred into a paste prepared by adding finely pulverized potassium nitrate (6.70 g, 66.3 mmol) to concentrated $H_2SO_4$ (30 mL), and the mixture was stirred at −10° to 0 ° C. in a salt/ice bath for one hour. The syrupy mass was then slowly poured onto cracked ice. After standing for one hour the yellow precipitate was filtered, washed on the filter with cold water, and air-dried to give 107 (5.27 g, 84.3% yield): mp 215°–20° C. (ethanol). The literature (Verma and Khan, 1978) reports mp 218°–220 ° C.

$^1$H NMR (DMSO-d6) 10.57 (s, 1 H, COOH), 8.36 (s, 1 H, aromatic), 8.2 (d, J=8.5 Hz, 1 H, aromatic), 7.82 (d, J=8.5 Hz, 1H, aromatic), 2.11 (s, 3 H, COCH$_3$) .

Preparation of 4-(Acetylamino)-3-Aminobenzoic Acid Hydrochloride (108)

To a stirred mixture of 107 (1.00 g, 4.46 mmol) and 10% Pd-C (1.0 g) in ethanol (10 mL) and 5% HCl (1.2 mL) was added dropwise hydrazine hydrate (55% hydrazine, 1.0 mL, 17 mmol). The mixture was stirred at room temperature for 1 hour, the catalyst was filtered, and the filtrate was concentrated under reduced pressure. Compound 108 (0.875 g, 100%) was obtained as a white solid residue: mp 220°–223° C. (methanol/hexane). A literature reference (Ellis and Jones, 1974) did not report the mp.

$^1$H NMR (CD$_3$OD) 7.49–7.29 (m, 2 H, aromatic), 7.20–7.12 (m, 1 H, aromatic), 2.16 (s, 3 H, COCH$_3$).

Preparation of 4-(Acetylamino)-3-Guanidinobenzoic Acid (113)

A mixture of 108 (100 mg, 0.43 mmol) and cyanamide (27 mg, 0.65 mmol) was mixed and heated at 85–100 C. with stirring for 15 minutes. The liquid mass was cooled to room temperature, dissolved in hot water (0.7 mL), and acidified with 1–2 drops of conc. HCl. The thick solid which separated was filtered and dried to give crude 113 (160 mg). This was recrystallized from 5% HCl to give the pure hydrochloride salt of 113 (50 mg, 52%): mp 284–287 C.

$^1$H NMR (TFA) 2.50 (s, 3 H, NCOCH$_3$), 6.50 (bs, 4 H, C(NH$_2$)$_2^+$), 7.55 (d, 1 H, aromatic), 8.25–8.44 (m, 3 H, aromatic & N$\underline{H}$C(NH$_2$)$_2^+$), 9.30 (bs, 1 H, NHAc).

EXAMPLE

Preparations of 4-(acetylamino)-3-[(hydroxyacetyl)amino]benzoic acid (109), 4-(acetylamino)-3-[(2,3-dihydroxypropionyl)amino]benzoic acid (110), 4 -(acetylamino)-3-[(aminoacetyl)amino]benzoic acid (111), and 4-(acetylamino)-3-[ (4-aminobutanoyl)amino]benzoic acid (112). The overall reaction scheme is shown in Table 20.

TABLE 20

Reaction Paths and Chemical Structures of Compounds 15–22, 107, and 109–112

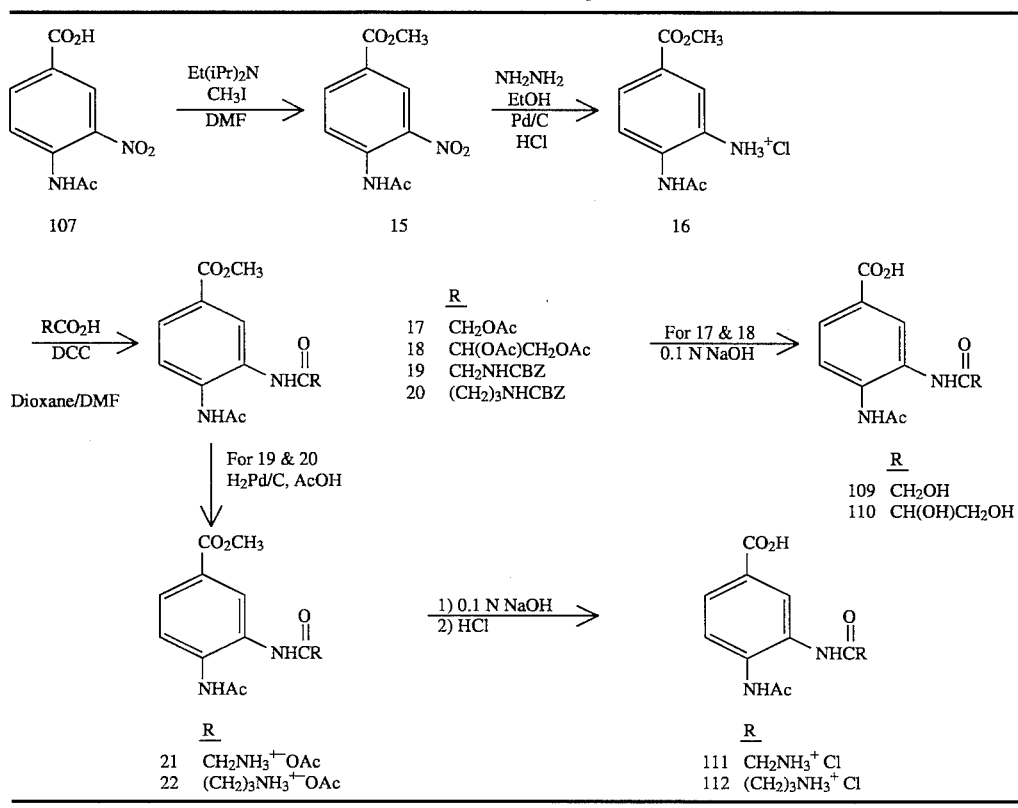

Preparation of Methyl 4-(Acetylamino)-3-Nitrobenzoate (15)

Compound 107 (1.50 g, 6.69 mmol) was dissolved in DMF (25 mL), and diisopropylethylamine (16.0, 92.7 mmol) and MeI (2.3 mL, 39 mmol) were added. The solid which formed was filtered and the filtrate was concentrated to dryness on a rotary evaporator to provide 15 (1.50 g, 94.3%) as a yellow solid: mp 123°–124° C. (ethanol). The literature (Appleton et al., 1970) reports mp 127° C.

Preparation of Methyl 4-(Acetylamino)-3-Aminobenzoate, Hydrochloride (16)

To a suspension of 15 (0.870 g, 3.65 mmol) in ethanol (30 mL) was added Pd-C (0.87 g) and 5% HCl (0.85 mL). Hydrazine hydrate (55% hydrazine, 0.85 mL, 0.47 g, 15 mmol) dissolved in ethanol (5mL) was then added dropwise to the above mixture. The reaction mixture was stirred at room temperature for ½ hour and the Pd-C was filtered. The filtrate was concentrated under vacuum to give 16 (0.500 g, 78.7% yield) as a white solid: mp 187°–190° C.

$^1$H NMR (DMSO-$d_6$) 9.21 (s, 1 H, NHCO), 7.50 (d, 1 H, aromatic), 7.36 (d, 1 H, aromatic), 7.14 (dd, 1 H, aromatic).

Preparation of Methyl 4-(Acetylamino)-3-[(Acetoxyacetyl)Amino]Benzoate (17)

Compound 16 (0.20 g, 0.96 mmol) was dissolved in a mixture of anhydrous DMF (2 mL) and anhydrous dioxane (5 mL), and the solution was cooled to 0°–5° C. in an ice bath. To this were added acetoxy acetic acid (0.124 g, 0.129 mmol) and DCC (0.198 g, 0.210 mL, 0.960 mmol). The reaction mixture was stirred for a few minutes at 0° C., the ice bath was removed, and the mixture was stirred at room temperature for 4 hours. The solid which separated was filtered and the filtrate was concentrated to dryness on a rotary evaporator. The solid residue was triturated with 5% HCl, filtered, and washed on the filter with water. The collected solid was then triturated with 5% NaHCO$_3$, filtered, washed with water, and dried under vacuum to give 17 (270 mg, 70.9% yield) as a white solid: mp 182°–186° C.

$^1$H NMR (DMSO-$d_6$) 2.08 (s, 3 H, NCOCH$_3$), 2.18 (s, 3 H, COCH$_3$), 3.83 (s, 3 H, CO$_2$CH$_3$), 4.68 (s, 2 H, CH$_2$), 7.73–7.81 (m, 2 H, aromatic), 8.11–8.16 (m, 1 H, aromatic), 9.65 (broad s, 1 H, NH), 9.57 (broad s, 1 H, NH).

Preparation of Methyl 4-(Acetylamino)-3-[(2,3-Diacetoxypropanoyl)Amino]Benzoate (18)

Compound 16 (0.12 g, 0.57 mmol) was dissolved in a mixture of DMF (2 mL) and dioxane (3 mL) and cooled to 0° C. A solution of 2,3-diacetoxypropionic acid (0.220 g, 1.15 mmol) in dioxane (3 mL) was added followed by the addition of dicyclohexylcarbodiimide (0.195 mL, 0.183 g, 0,870 mmol). The resulting reaction mixture was stirred for 3 hours, initially at 0° C. with slow warming to room temperature. The solid dicyclohexylurea which separated was filtered and the filtrate was concentrated to dryness on a rotary evaporator. The solid residue was filtered and washed on the filter with 5% HCl (5 mL), water (5 mL), 5% NaHCO$_3$ (5 mL), and again with water (2×10 mL). This was dried under vacuum to give 18 (200 mg, 91.3%) as a white solid: mp 130°–134° C.

$^1$H NMR (DMSO-$d_6$) 2.10 (s, 3 H, NCOCH$_3$), 2.20 (s, 3 H, OCOCH$_3$), 2.28 (s, 3 H, OCOCH$_3$), 3.91 (s, 3 H, COOCH$_3$), 4.46–4.68 (m, 2 H, CH$_2$—OCOCH$_3$), 5.43–5.49 (m, 1 H, CH—OCOCH$_3$), 7.48–7.56 (m, 1 H, aromatic), 7.84– 7.92 (m, 1 H, aromatic), 8.01–8.07 (broad s, 1 H, NH), 8.07–8.11 (m, 1 H, aromatic), 8.74–8.84 (broad s, 1 H, NH).

Preparation of Methyl 4-(Acetylamino)-3-{[(N-Benzyloxycarbonyl)Amino]Acetyl}Benzoate (19)

Compound 16 (0.20 g, 0.96 mmol) was dissolved in a mixture of anhydrous DMF (3 mL) and dioxane (5 mL) and cooled to 0° C. To this was added N-(benzyloxycarbonyl)-glycine (0.320 g, 1.53 mmol) and dicyclohexylcarbodiimide (0.295 g, 0.314 mL, 1.43 mmol). The reaction mixture was stirred overnight at room temperature, but the starting material did not completely disappear on TLC. The reaction mixture was filtered to remove dicyclohexylurea and the filtrate was concentrated to dryness on a rotary evaporator. The sticky semisolid residue was triturated with 5% HCl (5mL), filtered, and washed on the filter with water (5 mL). This was then triturated with 5% NaHCO$_3$ (5 mL), filtered, and washed on the filter with water (5 mL). This was dried under vacuum to give 19 (260 mg, 67.8% yield) as a white solid: mp 150°–153° C.

$^1$H NMR (DMSO-d$_6$) 2.11 (s, 3 H, NHCOCH$_3$), 3.79–3.95 (s, 5 H, CH$_2$—NH & CH$_3$COO), 7.28–7.45 (m, 5 H, aromatic), 7.58–7.67 (broad s, 1 H, NH), 7.67–7.87 (m, 2 H, aromatic), 8.06–8.20 (m, 1 H, aromatic), 9.41–9.54 (m, 2 H, NH).

Preparation of Methyl 4-(Acetylamino)-3-{4-[(N-Benzyloxycarbonyl)Amino]Butanoylamino} Benzoate (20)

Compound 16 (200 mg, 0.96 mmol) was dissolved in a mixture of anhydrous dioxane (2 mL) and anhydrous DMF (3 mL) and cooled to 0° C. To this was added 4-[N-(benzyloxycarbonyl)amino]butyric acid (395 mg, 1.78 mmol) followed by the addition of dicyclohexylcarbodiimide (0.32 mL, 0.300 g, 1.45 mmol). The resulting reaction mixture, initially at 0° C., was stirred and allowed to warm to room temperature overnight. The dicyclohexylurea which separated was filtered and the filtrate was concentrated to dryness on a rotary evaporator. The solid residue obtained was triturated with 5% HCl (10 mL), filtered, and washed on the filter with water. This was then triturated with 5% NaHCO$_3$ (10 mL), filtered, and again washed on the filter with water. The resulting solid was dried under vacuum to give 570 mg of a crude solid, mp 125°–167° C. This was purified by dissolving in chloroform (5 mL), since the impurities were soluble in chloroform but the desired product remained insoluble. The CHCl$_3$ solution was thus filtered to give 20 (200 mg, 60.0% yield) as a white solid: mp 166°–171° C.

$^1$H NMR (DMSO-d$_6$) 1.69–1.83 (m, 2 H, CH$_2$CH$_2$CH$_2$), 2.09 (s, 3 H, NHCOCH$_3$), 2.45–2.33 (m, 2 H, CO—CH$_2$), 3.04–3.11 (m, 2 H, N—CH$_2$), 3.82 (s, 3 H, COOCH$_3$), 5.02 (s, 2 H, CH$_2$—Ph), 7.32 (s, 5H, aromatic), 7.65–7.67 (m, 1 H, aromatic), 7.80–7.87 (m, 1 H, aromatic), 8.10–8.14 (m, 1 H, aromatic), 9.32–9.46 (broad s, 2 H, NH).

Preparation of Methyl 4-(Acetylamino)-3-[4-(Aminobutanoyl)Amino]Benzoate, Hydroacetate (21)

A mixture of 10% Pd-C (80 mg), water (1 mL). and glacial acetic acid (1 mL) was stirred at room temperature under 1.0 atmosphere of hydrogen gas for one hour. A solution of 19 (0.150 g, 0,375 mmol) in glacial acetic acid (5 mL) was then added, and the reaction mixture was stirred at room temperature for 24 hours. The catalyst was removed by filtration, washed on the filter with water (5 mL), and the filtrate was concentrated to dryness on a rotary evaporator to give an oily residue. This was dissolved in water (10 mL), extracted once with ethyl acetate (10 mL), and the aqueous layer was concentrated to dryness on a rotary evaporator. The oily residue was dried under vacuum to give 21 (80 mg, 66% yield).

$^1$H NMR (DMSO-d$_6$) 1.89 (s, 3 H, CH$_3$CO$_2$—), 2.10 (s, 3 H, NHCOCH$_3$), 3.33 (s, 2 H, CH$_2$—N), 3.84 (s, 3 H, CH$_3$OCO), 7.61–7.81 (m, 2 H, aromatic), 8.38–8.47 (m, 1 H, aromatic), 9.78–9.97 (broad s, 1 H, NH).

Preparation of 4-(Acetylamino)-3-[(4-Aminobutanoyl)Amino]Benzoate, hydroacetate (22)

A mixture of 10% Pd-C (60 mg), water (1 mL), and glacial acetic acid (1 mL) was stirred at room temperature under 1.0 atmosphere of hydrogen gas for one hour. A solution of 20 (100 mg, 0.234 mmol) in glacial acetic acid (5 mL) and chloroform (3 mL) was added to the mixture, and this was stirred under hydrogen at room temperature for 24 hours. The catalyst was filtered, washed on the filter with water (5 mL), and the filtrate was extracted with chloroform (2×5 mL). The aqueous layer was concentrated to dryness on a rotary evaporator and dried under vacuum to give 22 (70 mg, 83% yield) as a solid: mp 200°–204° C.

$^1$H NMR (DMSO-d$_6$) 1.87–1.94 (m, 5 H, CH$_2$CH$_2$CH$_2$ and CH$_3$CO$_2$—), 2.14 (s, 3 H, NCOCH$_3$), 2.51–2.60 (m, 2 H, CH$_2$—CO) 2.80–2.94 (m, 2 H, N—CH$_2$), 3.81–3.84 (s, 3 H, COOCH$_3$), 7.67–7.64 (m, 1 H, aromatic), 7.84–7.94 (m, 4 H, aromatic & NH$_3^+$), 8.18–8.22 (m, 1 H, aromatic), 9.84–9.89 (broad s, 2 H, NH).

Preparation of 4-(Acetylamino)-3-[(Hydroxyacety)Amino] Benzoic Acid (109)

Compound 17 (0.200 g, 0.652 mmol) was dissolved in 0.1N NaOH (7.93 mL) and stirred at room temperature for 2 hours. The alkaline aqueous layer was acidified to pH 2 with conc HCl, extracted with ethyl acetate (2×15 mL), and the extracts were dried (Na$_2$SO$_4$) and concentrated on a rotary evaporator to give only 8 mg of 109. The aqueous layer was concentrated on a rotary evaporator to 25% of the original volume, cooled, and the solid which separated was filtered. This was dried under vacuum to give 109 (60 mg, 58% yield) as a white solid: mp 214°–215 ° C.

$^1$H NMR (DMSO-d$_6$) 2.09 (s, 3 H, NCOCH$_3$), 4.00 (s, 2 H, CH$_2$OH), 5.69 (broad s, 1 H, OH), 7.47–7.55 (m, 1 H, aromatic), 7.59–7.75 (m, 1 H, aromatic), 9.35 (s, 1 H, NH), 9.75 (s, 1 H, NH), 12.34–12.95 (broad s, 1 H, COOH).

Preparation of 4-(Acetylamino)-3-[(2,3-Dihydroxypropionyl)Amino]Benzoic Acid (110)

Compound 18 (0.140 gins, 0.368 mmol) was taken up in cold 0.1N NaOH (8 mL) and stirred at 0° C. for 1 hour. The insoluble solid was filtered, the cooled filtrate was acidified to pH 3, and this was extracted with ethyl acetate (3×15 mL). The extracts were dried (Na$_2$SO$_4$) and concentrated on a rotary evaporator to give only 8 mg of solid product 110. The aqueous layer was then concentrated on a rotary evaporator and the residue dried under vacuum to give 110 (100 mg, 97.0% yield) as a white solid: mp 215°–217° C.

$^1$H NMR (DMSO-d$_6$) 2.09 (s, 3 H, NCOCH$_3$), 3.64 (broad s, 2 H, OH), 4.05–4.15 (m, 1 H, CH$_2$—OH), 4.88–4.94 ( m, 1 H, CH$_2$—OH ), 5.77–5.85 (m, 1 H, CH—OH), 7.56–7.78 (m, 2 H, aromatic), 8.20–8.29 (m, 1 H, aromatic), 9.40 (broad s, 1 H, NH), 9.63 (broad s, 1 H, NH), 12.81 (broad s, 1 H, COOH).

Preparation of 4-(Acetylamino)-3-[(Aminoacetyl)Amino] Benzoic Acid (111)

Compound 21 (80 mg, 0.24 mmol) was added to 0.1N NaOH (2mL) and the mixture was stirred at 0° C. for one hour. The solution was adjusted to pH 7 by the addition of 5% HCl (1.5 mL) and concentrated to dryness on a rotary evaporator to give a white solid (150 mg), which was a mixture of salts and product 111. This solid was dissolved in water, the insoluble material filtered, and the filtrate adjusted to pH 2–3 by the addition of 5% HCl (2–4 mL). The acidic solution was then concentrated to dryness on a rotary evaporator. The residue was dried under vacuum to give 111 (175 mg, >100% yield) as a white solid mixture containing inorganic salts: mp 220° C. (dec).

$^1$H NMR (DMSO-d$_6$) 2.16 (s, 3 H, NCOCH$_3$), 3.85–3.96 (s, 2 H, CH$_2$N), 7.69–7.77 (m, 1 H, aromatic), 7.93–8.00 (m, 1 H, aromatic), 8.14–8.21 (m, 1 H, aromatic), 8.26–8.37 (broad s, 2 H, NH$_3$), 9.90–10.05 (broad s, 1 H, NH), 10.50–10.65 (broad s, 1 H, NH).

Preparation of 4-(Acetylamino)-3-[(4-Aminobutanoyl)Amino]Benzoic Acid (112)

Compound 22 (60 mg, 0.17 mmol) was dissolved in cold 0.1N NaOH (1.5 mL) and stirred at 0° C. for one hour. The solution was adjusted to pH 7 and the aqueous layer was concentrated to dryness on a rotary evaporator. The residue was dried under vacuum to give 112 (136 mg) as a white solid mixture containing inorganic salts: mp 215°–240° C. (dec). This solid was dissolved in water (5 mL), the insoluble material was filtered, and the filtrate was concentrated to provide 112 (130 mg, 100%): mp 240°–245° C.

$^1$H NMR (D$_2$O) 1.89–1,92 (s, CH$_3$CO$_2$—), 1.98–2.10 (m, 2H, CH$_2$CH$_2$CH$_2$), 2.16–2.20 (s, 3 H, NCOCH$_3$), 2.55–2.64 (m, 2 H, COCH$_2$), 3.05–3.13 (m, 2 H, N—CH$_2$), 7.46–7.52 (m, 1 H, aromatic), 7.76–7.83 (m, 1 H, aromatic), 7.83–7.88 (m, 1 H, aromatic).

E. In Vitro Assay of the Inhibitory Activity

Comparison of inhibitory activities is by IC$_{50}$ to determine the concentration of inhibitor which causes 50% inhibition in a standard fluorometric assay. As described herein, the in vitro screen for effects of synthetic targets on neuraminidase utilizes two substrates, the fluorogenic 4-methylumbelliferyl-NANA (MUN) and the high molecular weight fetuin, with released sialic acid detected by the standard colorimetric assay (Aymard-Henry et al., 1973). In these assays, whole virus of type A or type B is the source of neuraminidase. The assay contains 0.1 mM 4-Me-umbelliferyl-N-acetyl-neuraminic acid in 100 μl of 50 mM sodium acetate at pH 6.0, 0.25 mM Ca$^{2+}$, 0.8 mM Mg$^{2°}$, 75 mM NaCl, with a fixed amount of purified virions as the neuraminidase source and dilutions of inhibitor included. Incubation is for 15 minutes at 37° C. 0.5 ml of "stop solution" (0.2M glycine, pH 11) is added and the fluorescence is read at 450 nm from excitation at 365 nm. The IC$_{50}$ is calculated by comparison to a sample without inhibitor but including the solvent in which the inhibitor was dissolved. All inhibitors were tested with viruses containing N2 (A/Tokyo/67) and type B (B/Memphis/3/89) neuraminidases. Inhibitors were also tested with a high MW substrate (fetuin) using the thiobarb assay procedure with small-scale modifications (Lentz, M. R., Webster, R. G., and Air, G. M. (1987).

The results using MUN as substrate are summarized in Table 10. Results with fetuin as substrate were similar. The above-described benzenoid compounds 101–112 contain much simpler side chain functionality than sialic acid. However, most are, as illustrated, approximately equipotent as inhibitors of influenza NA. Furthermore, compound 113 contains much simpler side chain functionality than DANA but is nearly equipotent as an inhibitor of influenza NA. Thus, the incorporation of additional interacting functional groups into the benzenoids should result in significantly enhanced activity.

TABLE 10

In vitro effects of inhibitors on NA in whole virus (IC$_5$O).

| Compound | MUN N2 | B/Mem/89 | Fetuin N2 | B/Mem/89 |
|---|---|---|---|---|
| 101 | >10 | >10 | 10 | 10 |
| 102 | >10 | >10 | 10 | 5 |
| 103 | 1 | 1 | 3 | 4 |
| 104 | 5 | 2 | 3 | 5 |
| 105 | 0.75 | 0.75 | 1 | 1 |
| 106 | >10 | 10 | >10 | >10 |
| 107 | 5 | 5 | 5 | 5 |
| 108 | >10 | >20 | >10 | N/D |
| 109 | 4 | 3 | >10 | 10 |
| 110 | 5 | 8 | 4 | >10 |
| 111 | 5 | 5 | 5 | 5 |
| 112 | >10 | >10 | >10 | >10 |
| 113 | 0.02 | 0.02 | 0.02 | 0.02 |
| sialic acid | N/D | >10 | N/D | N/D |
| DANA | 0.015 | 0.015 | 0.015 | 0.015 |

Note: N/D = not done. N/A = not available. The IC$_5$O unit is x μl of a 100 mM inhibitor solution to achieve 50% inhibition of NA activity.

Two benzenoids, compounds 105 and 113, stand out as significantly more potent than sialic acid. Interestingly, the nitro group alone (as in 107) or the phenol OH alone (as in 101) did not result in significant changes in activity. Compound is roughly 11 times more active than sialic acid, and compound 113 is about as active as DANA.

F. 3D Structure of NA-Benzenoid Inhibitor Complex

Native crystals of A/Tokyo/3/67 NA were grown by the hanging drop method (McPherson, 1985) using purified NA heads. To grow the crystals, 50 μl of protein and 50 μl of reservoir solution were used. The reservoir buffer consisted of 0.10M sodium phosphate and 0.15M sodium chloride solutions at pH 6.3. By X-ray methods, the space group of the N2 crystals was determined to be orthorhombic C222$_1$ with unit cell dimensions of a=120.97, b=141.14 and c= 142.16 Å. The N2-inhibitor complexes were prepared by soaking the native N2 C222$_1$ crystals in an about 5 mM buffer solution of compound/inhibitor for about 6 hours. The soaking buffer used contained 0.10M sodium phosphate, 0.15M sodium chloride, 5% DMSO, and 12.5% PEG 4000 at pH 6.3 (titrated using sodium hydroxide and hydrochloric acid).

The diffraction data were collected at room temperature on a SIEMENS multiple wire area detector with a RIGAKU rotating anode X-ray generator RU-200 using Cu Kα radiation. The data were processed using the XENGEN (Howard, 1985) package. For the structure determination of the native N2 C222$_1$ crystal form, the atomic coordinates of N2 protein that crystallized in tetragonal space group I422 (Varghese & Colman, 1991) were used as a model to obtain initial phases. The initial atomic model was obtained by molecular replacement methods (Fitzgerald, 1988). The structure was then refined by using the X-PLOR package (Brunger, 1992 and 1993) using rigid body, positional and simulated annealing procedures. The electron density for the structure was inspected on the Evans and Southerland PS-300 graphics system with FRODO software (Jones, 1978; Jones, 1985). Water molecules and sugar chains were fitted in the resulting ||F$_o$|–|F$_c$|5| electron density map. The resulting structure was used as a model in further N2-inhibitor complex structures. The N2-inhibitor complex structures were also refined using the X-PLOR (Brunger, 1992 and 1993) package and the inhibitor was included by building the molecule into ||F$_o$|–|F$_c$|| electron density maps, after initial rigid body refinements of the protein component. Finally, conjugate gradient and molecular dynamics refinements were performed and the addition of water molecules followed. The topology and the parameter files for inhibitors were created based on literature values and a small molecule crystal structure of the 4 -(acetylamino)-3-hydroxy-5-nitrobenzoic acid (compound 105) inhibitor obtained for this purpose (see below).

In the crystal of compound 105, the benzene ring atoms are planar within 0.026(2) Å with C—C bond length varying from 1.377(3) to 1.40(3) Å and endocyclic C—C—C bond angles from 118.7(2)° to 122.2(2)° which agree with accepted values (Bruno and Randaccio, 1980; Karle, 1952a & 1952b). The carboxyl, nitro, and N-acetyl groups are rotated with respect to the central benzene ring by 5.0(3)°, 45.0(2)°, and 37.3(1)°, respectively. The N-acetyl (N4, C7, O7, and O7) group is planar within 0.0009(2) Å. The C—O distance for the N-acetyl group is 1.209 Å. The two C—O bond distances of the carboxyl group are 1.290(3) Å (C9–O9) and 1.224(3) Å. (C9–O9') and the corresponding angles are 115.6()° (C1-C9 -O9), 120.2(2)° (C1-C9-O9'). For the nitro group, N—O distances are nearly equal: 1.231(3) Å (N5–O5) and 1.198(3) Å (N5–O5') and the corresponding angles are 117.0(2)° (C5-N5-O5) and 118.5(2)° (C5-N5-O5'). The C—O distance for the N-acetyl group is 1.209(3) Å. There are intensive hydrogen bond interactions present between molecules in the crystalline state.

TABLE 3

4-(acetylamino)-3-hydroxy-5-nitrobenzoic acid
Positional Parameters for Hydrogen Atoms
and their Estimated Standard Deviations

| ATOM | x | y | z | $B_{eq}(Å^2)$ |
|---|---|---|---|---|
| H—C2 | 0.511(3) | 0.376(2) | 0.175(3) | 3.8(3)* |
| H—O3 | 0.714 | 0.262 | 0.221 | 5.7 |
| H—N4 | 0.708(3) | 0.127(2) | 0.582(4) | 4.2(6)* |
| H—C6 | 1.118(3) | 0.301(2) | 0.476(3) | 3.5(5)* |
| H—C8 | −0.165 | 0.030 | −0.182 | 6.6* |
| H—C8[11] | 0.923 | 0.125 | 0.038 | 10.0 |
| H—C8[1] | 0.729 | −0.001 | −0.032 | 12.0 |
| H—O9 | 0.841 | 0.476 | 0.015 | 7.3 |

*Starred atoms were refined isotropically.

The compound crystallizes in a dimeric form with the constituent molecules hydrogen bonding between the carboxyl groups (Tables 3 and 4). A second intermolecular hydrogen bond is present between the oxygen O7 of the N-acetyl group and the H—O3 hydrogen of the hydroxyl group. Appropriate distances and angles for the H-bonds are shown in Tables 3, 4 and 5. Selected torsion angles describing the geometry of the phenyl substituents ($CO_2H$, $NO_2$, OH, and $C_2H_4NO$) are also shown in Tables 3, 4 and 5. Atomic coordinates, together with equivalent isotropic thermal parameters and structure amplitudes, are supplied in Tables 6–8 and Table 13. FIG. 14 represents the ORTEP drawing of compound 105.

TABLE 4

Bond Distances Involving Hydrogen Atoms
(In Angstroms)

| ATOM 1 | ATOM 2 | DISTANCE |
|---|---|---|
| O3 | H—O3 | 1.002(2) |
| O9 | H—O09 | 0.952(2) |
| N4 | H—N4 | 0.90(3) |

TABLE 4-continued

Bond Distances Involving Hydrogen Atoms
(In Angstroms)

| ATOM 1 | ATOM 2 | DISTANCE |
|---|---|---|
| C2 | H—C2 | 0.96(3) |
| C6 | H—C6 | 0.95(3) |
| C8 | H—C8 | 0.949(3) |
| C8 | H—C8[11] | 0.945(2) |
| C8 | H—C8[1] | 0.955(2) |

Numbers in parentheses are estimated standard deviations in the least significant digits.

TABLE 5

4-(acetylamino)-3-hydroxy-5-nitrobenzoic acid
Bond Angles Involving Hydrogen Atoms (in Degrees)

| ATOM 1 | ATOM 2 | ATOM 3 | ANGLE |
|---|---|---|---|
| C3 | O3 | H—O3 | 103.8(1) |
| C9 | O9 | H—O9 | 109.2(2) |
| C4 | N4 | H—N4 | 113.0(2) |
| C7 | N4 | H—N4 | 119.0(2) |
| C1 | C2 | H—C2 | 125.0(2) |
| C3 | C2 | H—C2 | 115.0(2) |
| C1 | C6 | H—C6 | 130.0(1) |
| C5 | C6 | H—C6 | 111.0(1) |
| C7 | C8 | H—C8 | 109.6(2) |
| C7 | C8 | H—C8[11] | 109.9(2) |
| C7 | C8 | H—C8[1] | 108.9(2) |
| H—C8 | C8 | H—C8[1] | 108.9(2) |
| H—C8 | C8 | H—C8[11] | 110.0(2) |
| H—C8[11] | C8 | H—C8[1] | 109.5(2) |

Numbers in parentheses are estimated standard deviations in the least significant digits.

The structures of N2-benzenoid complexes were determined for compounds 105, 106, 108–111, and 113. The complex crystals were prepared by soaking the $C222_1$ crystals of N2 in a solution containing 0.1M phosphate (pH 7.2), 0.15M NaCl, 12.5% PEG 3350, 5% DMSO, and 5 mM benzenoid. The diffraction data were collected on a SIEMENS area detector and processed using the XENGEN package. The statistics from the crystallographic refinements of compounds 105, 106 and 108 are shown in Table 11.

TABLE 11

Crystallographic Data for NA-Benzenoid Complexes

| Compound | Number of Reflections | Resolution, Å | R Factor, % | R.M.S. Bond Length, δÅ | R.M.S. Bond Angle, δ° |
|---|---|---|---|---|---|
| 105 | 33,264 | 1.8 | 26.1 | 0.028 | 2.6 |
| 106 | 25,898 | 2.4 | 22.5 | 0.024 | 2.3 |
| 108 | 17,723 | 2.4 | 21.0 | 0.023 | 2.4 |

Figure 8:
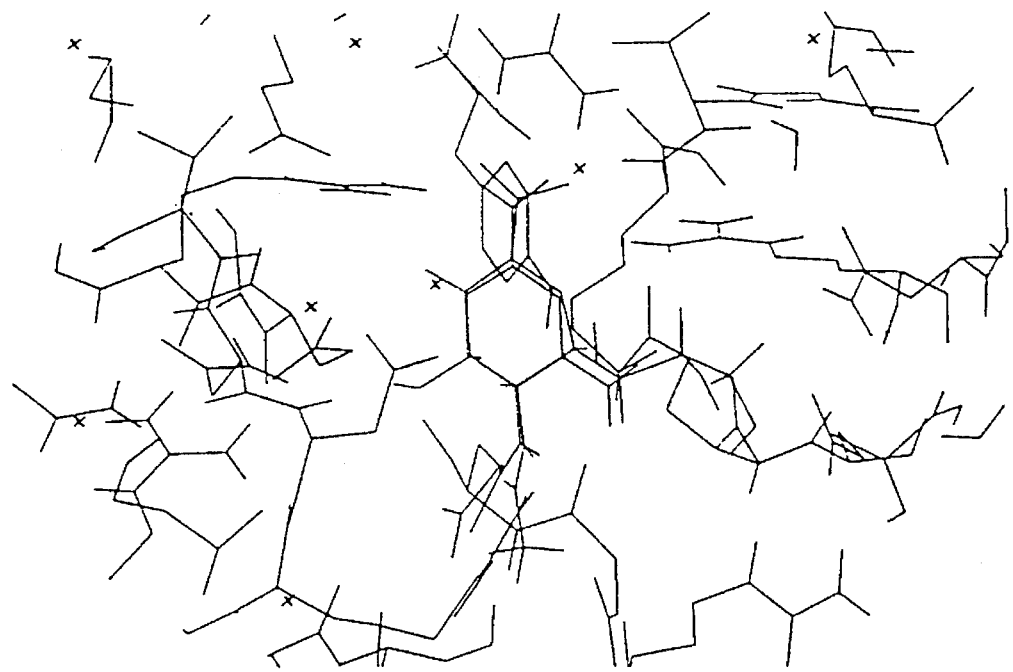
FIG. 8 shows a graphical image of the NA-105 complex, including superimposition over the complex of NA-DANA.
Figure 8:
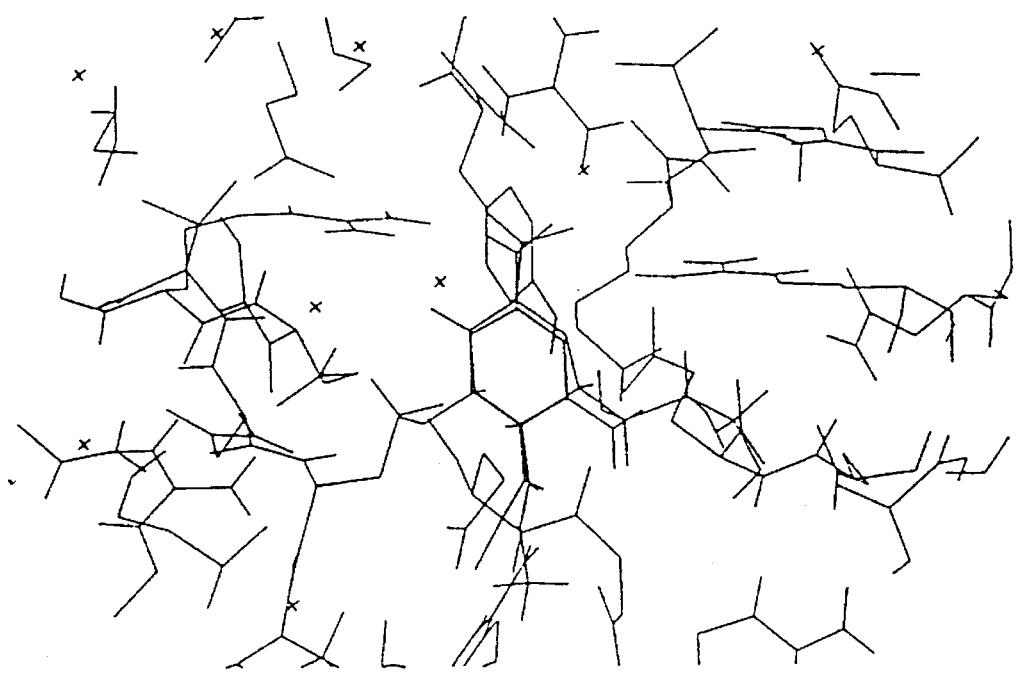

These structures reveal that the aromatic compounds occupy the same site as DANA in NA with similar interactions between the active site residues and the carboxyl and N-acetylamino groups.. An interaction between the benzene ring and the hydroxyl of Tyr 406 (N9 numbering) appears to dictate this orientation. This is illustrated in the graphics image of the NA-105 complex, which also contains a superimposed image of bound DANA (FIG. 8). Analysis suggested that the $NO_2$ and OH groups were not interacting significantly with the protein. Thus the surprisingly enhanced activity in 105 as compared to sialic acid must result from other effects. Possibilities include effects on water solubility, electron density of the benzene ring, and/or on the $pK_a$ of the amide N-H, carboxylate, or phenol. The magnitude of enhanced activity seen for 105 is consistent with such variables.

G. Computer Aided Design of the Inhibitors

Three computer programs, Macromodel, GRID and DelPhi, were used as a tool in the design of benzenoid inhibitors. As an aid in designing new ligands, the software GRID (for recent developments, see Wade et. al., 1993; Wade and Goodford, 1993), developed by P. J. Goodford, is used to study the inhibitor binding site of neuraminidase. This permits predictions of favorable changes to ligand structure involving the modification of previously observed interactions, or the incorporation of additional interactions (not found for DANA), into the next generation benzenoid targets. The GRID procedure determines energetically favorable binding regions on molecules of known structure, and may be applied to both small and macromolecules. In Goodford's method, a small chemical probe is passed through a three-dimensional array of points around a molecule (or binding site), and the interaction energy between the probe and target is calculated at each point in the array. The GRID energy function consists of Lennard-Jones, electrostatic, and explicit hydrogen bonding terms. Energies are computed as the sum of pairwise interactions between the probe and each atom in the target. A strength of this approach is that the hydrogen bonding term depends not only on the length of the bond, but also the orientation (angle) of the donor and acceptor atoms as well as their nature. Interactions involving more than two hydrogen bonds to a single probe may also be calculated. In this manner GRID can accurately reproduce experimental observations of hydrogen bonding geometries. Energy surface contours, established at any user-defined energy level, are then generated and displayed graphically using any of a variety of graphics programs. GRID thus can identify regions of the receptor surface where specific, favorable ligand-protein interactions may occur.

Several probes have been utilized:
(1) Methyl (—$CH_3$)
(2) Chorine (—Cl)
(3) Fluorine (—F)
(4) Ammonium (—$NH_3^+$)
(5) Amide (—NH2 and —NH—)
(6) Aromatic Amine (—N=)
(7) Carbonyl (=O)
(8) Carboxyl (—O)
(9) Ether (O)
(10) Hydroxyl (—OH)
(11) Water ($H_2O$)
(12) Phenol (—OH)

By contouring a slightly repulsive energy, a contour surface similar to a solvent-accessible surface is generated to define the volume shape within which all ligands must fit. The probes are then employed to determine if they might be incorporated into appropriate side chains for favorable interactions with the binding site.

Figure 9:
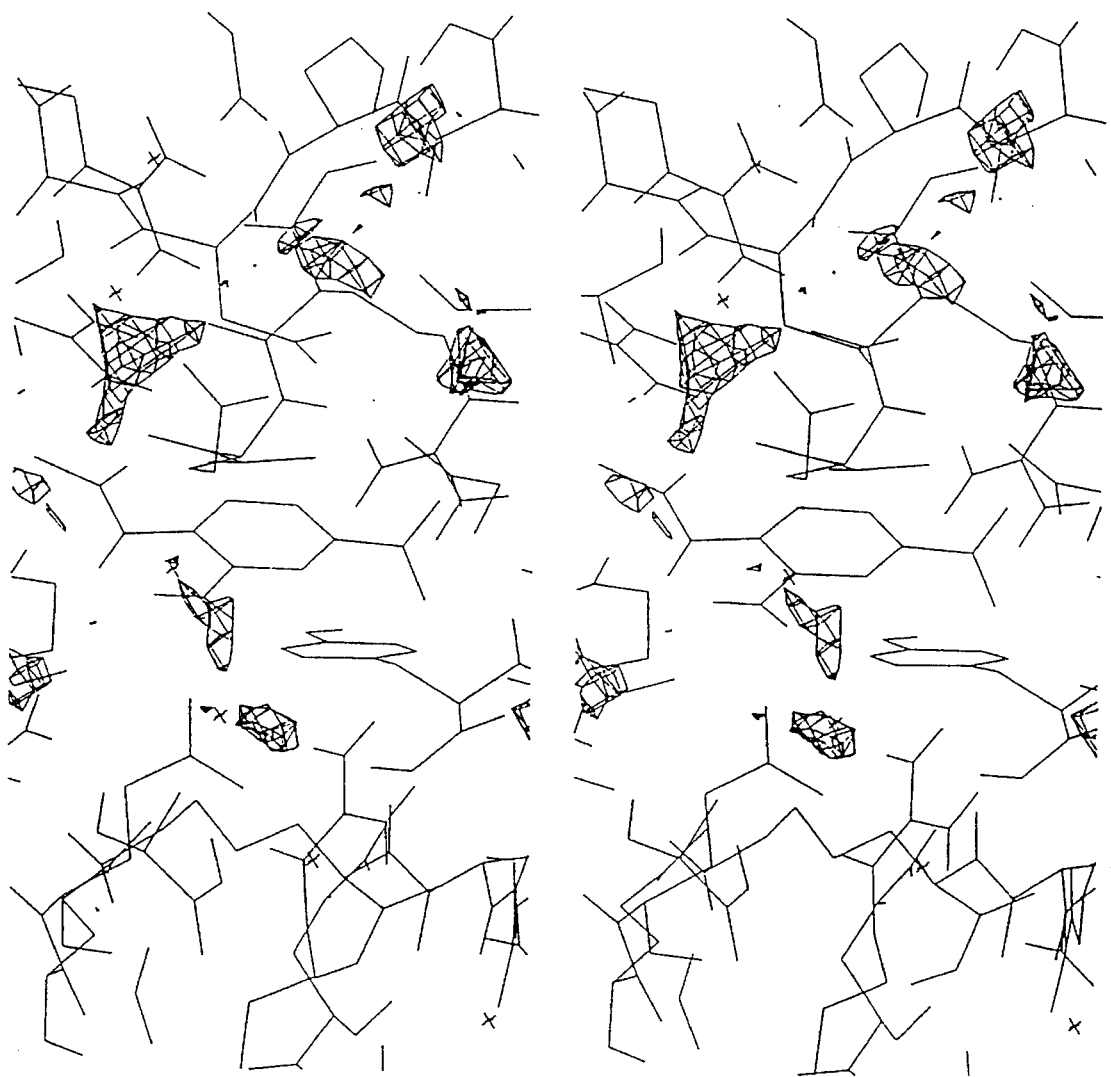
FIG. 9 shows a GRID map, using a water probe, of the NA-108 complex.

To illustrate the utility of GRID for aiding ligand design, a contour map was generated using water as the probe molecule, and the resulting surface was contoured at the −8.5 kcal/mole level. See FIG. 9 GRID Map, Using a Water Probe, for the NA-108 Complex. Attractive contours between the water probe and the protein indicate regions where water could remain undisplaced in the receptor binding pocket when the ligand binds. If water was predicted to bind very strongly to a site, newly designed ligands may use water as a "bridge" between ligand and protein. Alternatively, if other probes are found which bind more strongly than water at a given site, they may be used to displace water from the binding site. The release of bound water from a site is often desirable since it makes a favorable entropic contribution to the free energy of ligand binding.

Once new target compounds am designed, they are evaluated using several computational methods before synthesis. Molecular mechanics calculations (MM2* and MM3* as incorporated in Macromodel) are performed to insure that the required conformations are energetically reasonable. Also, conformational space will be searched using Monte Carlo methods as implemented in Macromodel. However, given the planar, rigid nature of the benzene nucleus, it is anticipated that extensive conformational freedom will be a minimal problem in the proposed class of structures. It is also possible to estimate the quality of fit for the newly designed ligand in the binding site.

Next, interaction energies of minimized ligands with the protein are calculated using the software program DelPhi (Klapper et. al., 1986).

The charge distribution on the inhibitor molecules was calculated using the semi-empirical procedures of MOPAC 6.0 (Dewar, 1983). All strums of N2 protein presented here were refined using only half of the asymmetric unit (one monomer of the neuraminidase protein) using the non-crystallographic symmetry element (2-fold axis) to generate the whole unit.

The $IC_{50}$ constants for three selected inhibitors (compounds 105, 106, and 108) have values of 5.0, 10.0 and 20.0 units, respectively. By solving a Poisson-Boltzman equation, $K_i$ binding constants of these inhibitor candidates were approximated to be $5.6 \times 10^{-5}$, $3.8 \times 10^{-4}$ and $7.1 \times 10^{-3}$ M, respectively (Gilson, Sharp & Honig, 1988; DelPhi 2.0, 1993; Tanford & Kirkwood, 1957; Bashford & Karplus, 1990; Davis et al., 1991; Juffer et al., 1991). These constants were used to set up the parameters for the calculation of the $K_i$ of newly designed inhibitors by the employment of DelPhi 2.0.

Terms contributing to the total electrostatic energy of a protein system were partitioned into three categories (Gilson & Honig, 1988). First, there was the Coulombic interaction of the charges with each other, $\Delta G_c^o$. Then, there was the interaction of charges with a polarizable solvent, $\Delta G_p^o$. Finally, the interaction of charges with the ion atmosphere in the solvent was calculated, $\Delta G_a^o$. Thus, the total electrostatic energy, $\Delta G^o$ can be written as:

$$\Delta G^o = \Delta G_c^0 + \Delta G_s^0 = \Sigma_i(\Delta G_{ci}^o + \Delta G_{si}^0)$$

Where $\Delta G_s^o = \Delta G_p^o + \Delta G_a^o$ and i denotes the contribution of each charge. $\Delta G^o$ can also be expressed in the form of a linear Poisson-Boltzmann (PB) equation:

$$\Delta G^o = \tfrac{1}{2}\Sigma_i q_i (\phi_{c,i} + \phi_{s,i})$$

Where $\phi_{c,i}$ is a Coulombic potential, and $\phi_{s,i}$ is a potential produced by the solvent. Both potentials are measured at the location of charge i.

The potential reference state is defined by a potential of all charges infinitely separated in a medium-corresponding to the dielectric constant of the molecule and containing atmosphere with zero ionic strength. All energies and potentials reported here are defined according to this reference state (Gilson & Honig, 1988).

The change in total electrostatic energy (i.e. the binding energy) when two molecules such as the protein and inhibitor form a complex may be calculated using a two-step thermodynamic process (Gilson & Honig, 1988). The initial state has beth molecules fully solvated and infinitely separated from each other. In step one, each molecule is partially desolvated by removing the solvent from regions that the other molecule will come to occupy in the complex after binding. The removed solvent is then replaced with a medium having a dielectric constant of the molecules and a zero ionic strength (no charge). The work involved in this process, $\Delta G_s$ is the change in the solvent interaction energies of the two molecules upon binding:

$$\Delta G_s = \Delta G_{s,1} + \Delta G_{s,2}$$

In the second thermodynamic step, the charges of a first molecule are transferred to the low-dielectric space prepared next to the second molecule from the previous step. The work done in this step $\Delta G_{inter}$ is the electrostatic interaction energy between the charges of the two molecules calculated with the complex surrounded by solvent:

$$\Delta G_{inter} = \Delta G_{compl} - (\Delta G_{1,2} + \Delta G_1)$$

Figure 10:
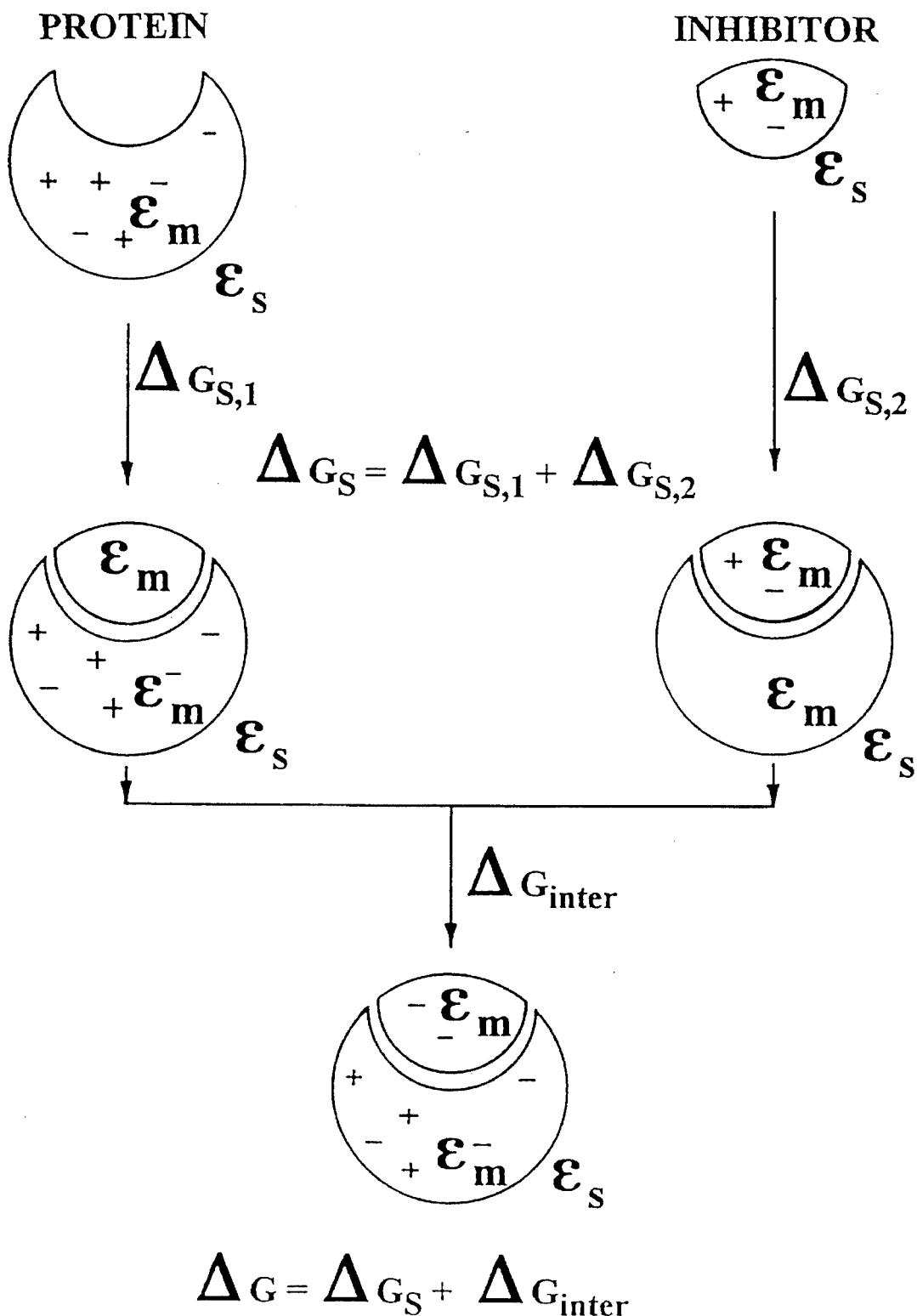
FIG. 10 shows a graphical representation of the thermodynamical processes for calculation of the change in total electrostatic energy of two molecules (protein and inhibitor) upon intermolecular binding where $\epsilon_m$ is the dielectric constant of the protein molecule ($\epsilon_m$=2.0) or of the inhibitor molecule and $\epsilon_s$ is the dielectric constant of the solvent ($\epsilon_s$=80.0 for a physiological liquid).

The final binding energy, $\Delta G$, is separated into the change in the hydration energy $\Delta G_s$ of both molecules plus the solvent screened electrostatic interaction energy $\Delta G_{inter}$ of the two molecules. The graphical representation of the above mentioned thermodynamical steps is rendered in FIG. 10. A summary of the results from DelPhi calculations is supplied in Table 14. The grid size used for the above calculations was 45–65 with 67% fill and an ion probe radius of 1.8 Å. The inner dielectric constant for protein varied from 2.0 to 4.0, whereas the outer dielectric constant for solvent varied from 78.3 to 80.0. At the introductory stage, the ionic strength of solvent was assigned a value of 0.145M (physiological liquid). At the latter stage of these simulations, the ionic strength of solvent was assumed to be 0.01M (Ripoll, 1993).

The modeled inhibitors compound 203 through compound 213 (Table 21) were first created based on small molecules which had previously solved crystal structures (Gozlan, P. H. & Riche, 1976; Carpy & Goursolle, 1980; Bryan et al., 1980; Bruno & Randaccio, 1980; Metzger et al., 1989; Soundarajan et al., 1993; Metzger et al., 1993; Nielsen & Larsen, 1993; Kageyama et al., 1993). Second, every inhibitor modeled was modeled inside the N2 active site. In this way, the crystal structure of N2 with known inhibitors together with the GRID maps were used to guide the placement of specific substituents on the core benzene ring of the modeled inhibitors. Finally, an energy X-PLOR refinement of inhibitor inside protein was done using a conjugate gradient technique. Next, a careful determination using FRODO was undertaken to check the conformation of the inhibitor and its orientation. The visual examination was followed by DelPhi calculations to obtain binding energy and binding K constants.

TABLE 21

Chemical Structures for Several Relevant Inhibitor Candidates 105, 106, 108, 203, 205, 206, 207, 208, 209, 209[1], 210, 211, 212 and 213
COMPOUNDS

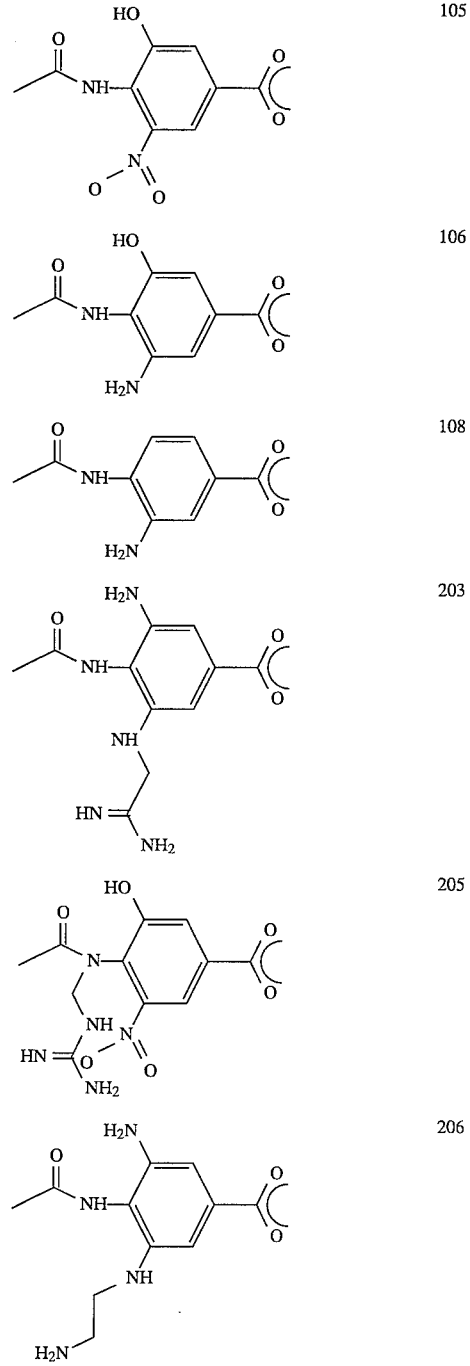

TABLE 21-continued

Chemical Structures for Several Relevant Inhibitor Candidates
105, 106, 108, 203, 205, 206, 207, 208, 209, 209[1], 210, 211,
212 and 213
COMPOUNDS

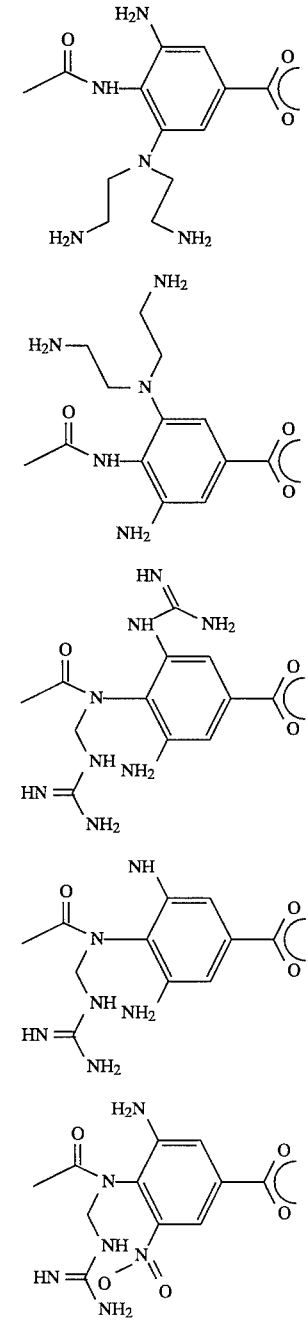

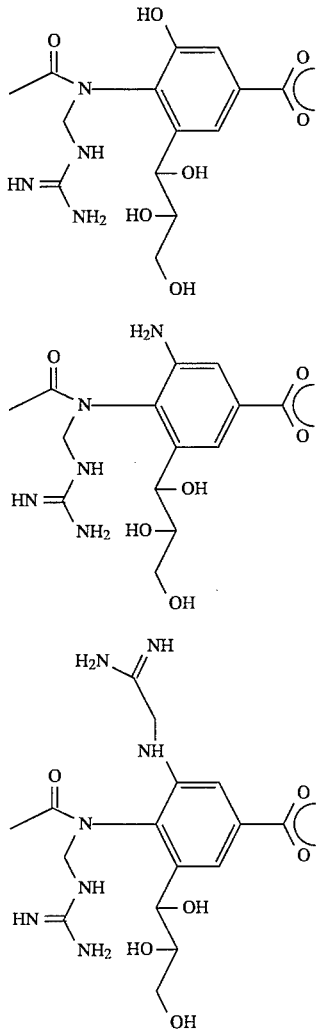

The FDPB method used here, DelPhi, (Tanford & Kirkwood, 1957; Bashford & Karplus, 1990; Davis et al., 1991; Juffer et al., 1991) makes possible reasonable estimates for the large solvent polarization terms that are frequently neglected in conformational analyses. As seen in Table 14, charge-solvent interactions can make large contributions to the total energy of a macromolecular system. The values for this interaction depend strongly on a dielectric constant $\epsilon$. Without exact knowledge of $\epsilon$ for inhibitors, the calculations of $\Delta G_{s,2}$ (and $\Delta G_s$, $\Delta G$ as a consequence) have a very large inherent error. A way of measuring or calculating $\epsilon$ is necessary to obtain introductory agreement with the expected experimental values. As shown in Table 14, it is possible to obtain results in qualitative agreement with experimental values. Binding affinity constant, K, reflects accurately the experimental values observed. The measured value of $K_{total}$ for B/Lee/40—DANA complex is $\sim 5.6 \times 10^{-6}$ which is close to the calculated value of $4.8 \times 10^{-6}$. As noted above, it has been found that inhibitor compound 105 binds strongest to N2, while compound 106 bind fairly well and compound 108 binds the weakest to N2. In order to elucidate the thermodynamic properties of the N2/inhibitor binding, a $K_{electr}$ is reported in Table 14. This constant corresponds only to a pure electrostatic interaction between a protein and inhibitor, without consideration of solvent environment influence. It is seen that the values of $K_{electr}$ agree qualitatively with the binding affinity, but the values of binding affinities are overestimated. In order to obtain quantitative agreement with experiment, it is necessary to develop atomic parameters which yield appropriate hydration energies for compounds representative of the chemical groups found in proteins and inhibitors, such as carboxylates, ammoniums, alcohols (Gilson & Honig, 1988), $pK_a$ of protein residues (ionizable groups) (Yang et al., 1993), and ionization potential changes of residues (Gilson, 1993).

Figure 11:
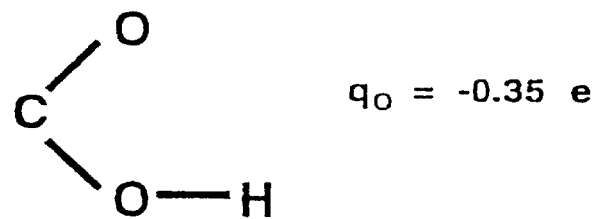
FIG. 11 shows the charges of a carboxyl group for the relevant inhibitor candidates as a function of protonation of the group. p$K_a$ analysis suggests that the charges of the deprotonated carboxyl are more relevant.
Figure 11:
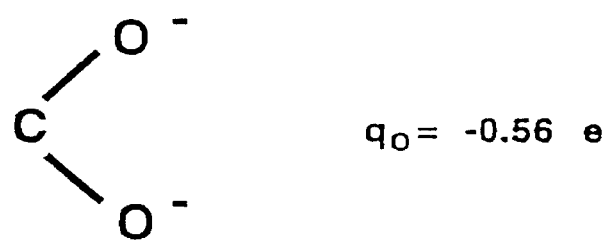
Figure 7:
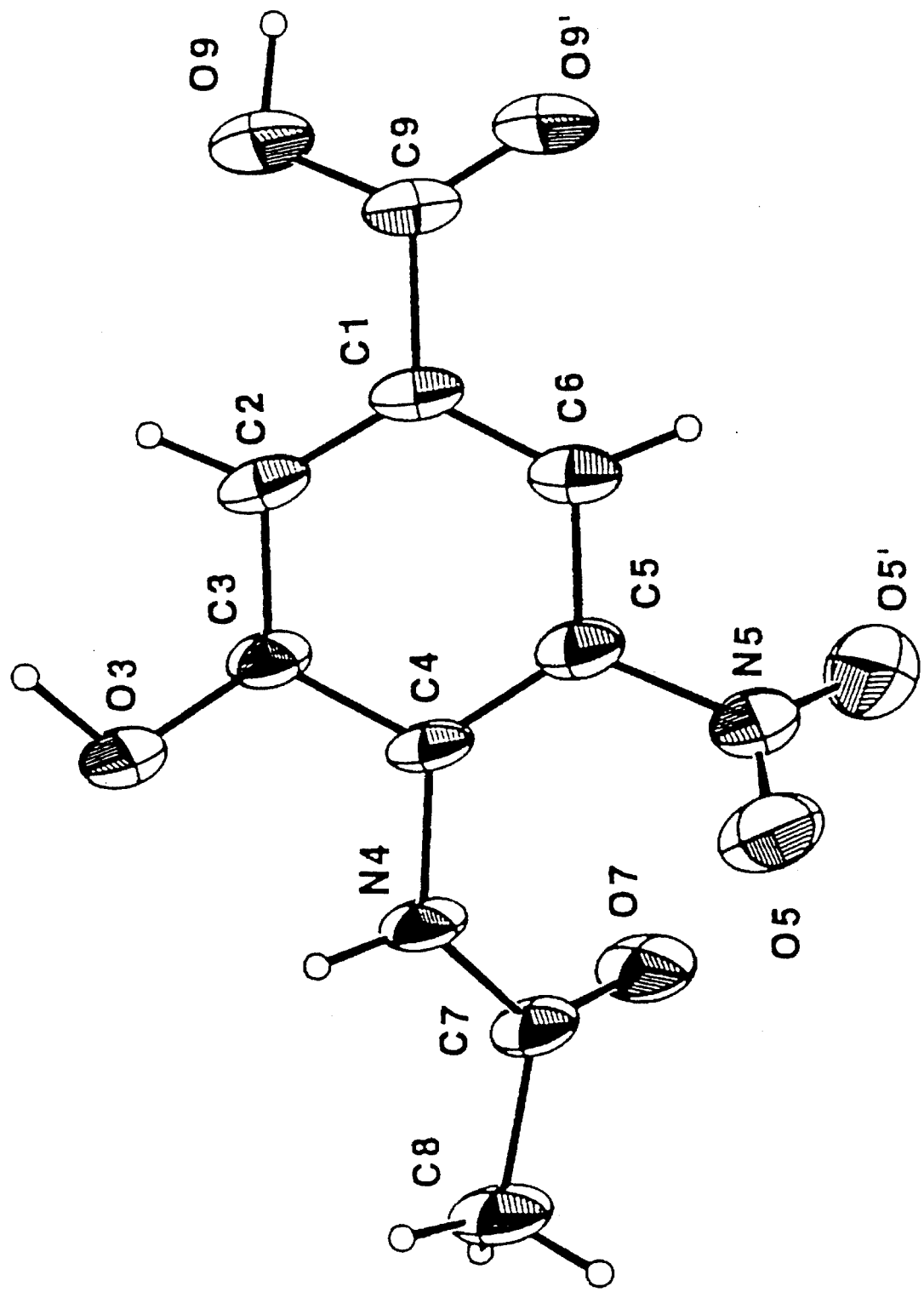
FIG. 7 represents the ORTEP drawing of compound 105 4-(acetylamino)- 3-hydroxy-5-nitrobenzoic acid.

Charges also play an important role in the elucidation of the above calculations. The charge data for the current inhibitors was calculated and proved to be sensitive to charge magnitude and distribution. The $pK_a$ value for the candidate inhibitors was approximated to be around 3.5 based on comparison to $pK_a$ of benzoic acid (~ 3.0) (CRC Handbook, 1993) and acetic acid (~4.0)(CRC Handbook, 1993). The N2 protein soak solution with various inhibitors and the mother liquor had a pH of 6.5. This strongly suggests that at this pH, the inhibitors are deprotonated at the carboxyl group (Yang et al., 1993; Gilson, 1993). As follows, the total charge of these inhibitors was assumed to be equal to $-1.0$ of the electron charge. FIG. 11 shows the different charges on carboxyl groups of the candidate inhibitors based on the presence/absence of the involved proton. FIG. 16 supplies the numbering scheme.

Calculated charges for several inhibitor candidates are listed according to functional groups in Table 9. These charges were calculates using MOPAC 6.0 AM1 algorithm (Dewar et al., 1985). Because of the above assumptions, every candidate molecule had a $-1$ e charge assigned and no proton present on the carboxyl group.

TABLE 9

Figure 6:
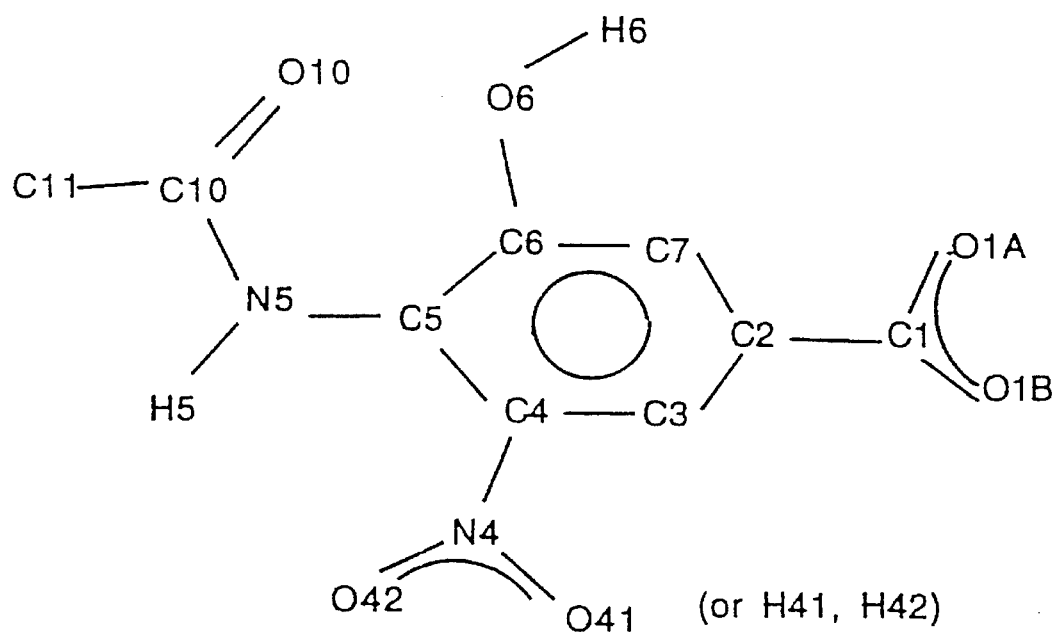
FIG. 6 shows a general structure for 4-(acetylamino)-3-hydroxy-5-nitrobenzoic acid 105 and the numbering scheme for its constituent atoms.

Partial charge distribution on the molecules (molecular charge = −1 e, no carboxylic proton) in the units of one electron charge. Numbering scheme is explained in FIG. 6.

| ATOM NAME | BASIC CHARGE | 105 CHARGE | 108 CHARGE | 106 CHARGE |
|---|---|---|---|---|
| O1A | −0.56 | −0.56 | −0.55 | −0.55 |
| O1B | −0.56 | −0.56 | −0.55 | −0.55 |
| C1 | 0.36 | 0.36 | 0.36 | 0.36 |
| N5 | −0.32 | −0.32 | −0.32 | −0.27 |
| H5 | 0.22 | 0.23 | 0.26 | 0.22 |
| C10 | 0.30 | 0.30 | 0.31 | 0.29 |
| O10 | −0.37 | −0.37 | −.39 | −0.39 |
| C11 | −0.25 | −0.25 | −0.24 | −0.24 |
| O6 | — | — | −0.29 | −0.29 |
| H6 | — | — | 0.23 | 0.23 |
| N4 | — | −0.31 | 0.57 | −0.31 |
| O41 | — | — | −0.40 | — |
| O42 | — | — | −0.40 | — |
| H41 | — | 0.15 | — | 0.18 |
| H42 | — | 0.15 | — | 0.18 |

The charge distribution of each candidate molecule was consistent from one molecule to the next. These calculations were examined by comparison of dipole moments and ionization constants of molecules with the same parameters from similar molecules with known values. Also, the same calculations were performed with m-nitrobenzoic acid and proved to be very similar (20% error) to measured values (CRC Handbook, 1993).

H. Classes of Compounds

As used herein, the "effective amount" of a compound of the invention required for use in the methods described herein will vary not only with the particular compound selected but also with the mode of administration, the nature of the condition in the subject, and the age and health of the subject. The exact dosage will ultimately be determined by a physician or other person skilled in the art. However, a suitable dose will generally range from about 0.01 to about 200 mg/kg of bodyweight per day. More preferably, an effective amount (suitable dose) will range from 0.1 to 50 mg/kg/day. Treatment may occur before infection by influenza (i.e. prophylaxis), at the start of infection, or after the onset of established symptoms. Treatment with the effective amount may be given 1 to 4 times daily and the typical duration will range from 3 to 7 days, or until virus is no longer present and/or symptoms have disappeared. Those skilled in the art will recognize that deviations from the above described treatment methods and effective amounts are possible and are to be included in the subject matter taught herein.

Furthermore, it is possible that, during therapy, the compounds may be administered as pure chemical or as a pure pharmaceutically acceptable salt or derivative. However, it is preferable to provide the active chemical, or its pharmaceutically acceptable salt or derivative, as a pharmaceutical formulation, either as a dry powder (tablet or capsule form or with a suitable carrier), or as a solution or suspension (in water or in physiologically acceptable solvents or cosolvents such as ethanol, propylene glycol, or PEG 400). The appropriate pharmaceutical formulation may be administered by oral, intranasal, intravenous, intramuscular or other appropriate modes. The desired dosage (effective amount) may be administered in one or in divided doses at appropriate intervals each day. The compounds and compositions of the invention may also be administered in combination with other therapeutic agents. Those skilled in the art will appreciate that dosages and modes of administration are readily determinable without undue experimentation.

This invention thus describes a class of influenza virus neuraminidase inhibitors, their pharmaceutically acceptable salts and derivatives, and mixtures thereof having general structure I.

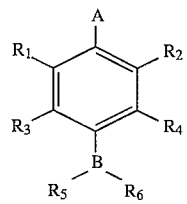

GENERAL STRUCTURE I

In structure I, A should be acidic because it is dominantly involved in the interaction with three positively charged arginine side chains in the binding site. Thus, the possible constituents for A include $CO_2H$, $CO_2CH_3$ (potential "prodrug"), $NO_2$, $SO_3H$ and $PO_3H_2$. In addition, constituent B is nitrogen in sialic acid and DANA. Thus, a potential new inhibitor could retain the nitrogen at position B. However, substitution with CH, O, or S would likely retain most of the useful characteristics at site B while introducing versatility for substituents $R_5$ and $R_6$.

Based upon computer-assisted molecular modeling studies, the x-ray crystal structures of several influenza neuraminidases and their complexes with sialic acid, DANA, and synthetic inhibitors having general structure I, evaluation of the enzyme's sialic acid binding site surface for sites that would interact favorably with additional ligand functionality (e.g., using GRID), the calculations of binding constants for newly designed ligands, and in vitro enzymatic studies with the compounds in Table 12, constituents suitable for $R_1$–$R_6$ in general structure I have been determined. $R_1$ and $R_2$ each may be either H, $NO_2$ or $(CH_m)_nX_1$, where m is either 1 or 2, n is an integer from 0 to 4 and $X_1$ is one of the following: guanidino, OH. $NH_2$, SH, $NO_2$, F, Cl, Br, I, CN, $CF_3$, $CO_2H$, $SO_3H$ and $PO_3H_2$. $R_3$ and $R_4$ are each selected from the following: H, $(CH_o)_pX_2$, $(CH_o)_pCHX_2CH_2X_2$, $NH(CH_o)_pCHX_2CH_2X_2$, $NHCO(CH_o)_pCH_2X_2$, and $NHCO(CH_o)_pCHX_2CH_2X_2$ where o is either 1 or 2, p is an integer from 0 to 4 and $X_2$ is selected from the group consisting of H, guanidino, OH, $NH_2$, SH, $NO_2$, $CF_3$, $CO_2H$, $SO_3H$ and $PO_3H_2$. Also, $R_5$ is chosen from the following constituents: H, OH, $NH_2$, $(CH_k)_1X_3$, $CO(CH_k)_1X_3$, $SO(CH_k)_1X_3$ and $SO_2(CH_k)_1X_3$ where k is either 1 or 2, l is an integer from 0 to 4 and $X_3$ is guanidino, OH, $NH_2$, SH, $NO_2$, $CF_3$, $CO_2H$, $SO_3H$ or $PO_3H_2$. Finally, $R_6$ is H, $CH(OH)X_4$, $CH(NH_2)X_4$, $COX_4$, $SOX_4$, or $SO_2X_4$, where $X_4$ is H, $CH_3$, $CH_3CH_2$, $CH_3CHCH_3$, $CH_3CH_2CH_2$ or a halogen substituted analog of $X_4$. In this embodiment, $R_3$ is not H when $R_4$ is H.

In another preferable embodiment, this invention provides a class of influenza virus neuraminidase inhibitors, their analogs, their pharmaceutically acceptable salts and derivatives, and mixtures thereof having the same general formula. However, in these inhibitors, constituent A is $CO_2H$ or $CO_2CH_3$, and B is either CH or N. Also, both $R_1$ and $R_2$ are H or $NO_2$. $R_3$ is H, OH, $NH_2$, guanidino, $NO_2$, F, Cl or Br. Furthermore, $R_4$ is further divided into constituent $QR_7$ where Q is selected from O, NH or $CH_2$ and $R_7$ is either H, $(CH_2)_oX_1$, $(CH_2)_oCHX_1CH_2X_1$, $CO(CH_2)_oCH_2X_1$ or $CO(CH_2)_o CHX_1CH_2X_1$ where o is an integer from 0 to 4 and $X_1$ is either H, guanidino, OH or $NH_2$. In addition, $R_5$ is $COCH_3$ and $R_6$ is $(CH_2)_pX_2$ where p is an integer from 0 to 4 and $X_2$ is OH, $NH_2$ or guanidino.

In yet another embodiment, this invention provides further influenza virus neuraminidase inhibitors, their analogs, their pharmaceutically acceptable salts and derivatives, and mixtures thereof having the same general formula I (as above). But in this embodiment, A is either $CO_2H$ or $CO_2CH_3$, B is N, $R_1$ is H or $NO_2$ and $R_2$ is H or $NO_2$. In addition, $R_3$ is either H, OH, $NO_2$, $NH_2$, or guanidino. $R_4$ is selected from the group consisting of the following: H, OH, OAc, $NH_2$, guanidino, $NHCOCH_2OH$, $NHCOCH(OH)CH_2OH$, $NHCOCH_2NH_2$, $NHCOCH_2CH_2CH_2NH_2$, CHO, $CH_2OH$, $CH_2OAc$, $CH_2CH_2OH$, $CH_2CH_2CH_2OH$, $CH_2CH(OH)CH_2OH$, $CH_2CH_2CH_2CH_2OH$, $CH_2CH_2CH(OH)CH_2OH$, $CH_2I$, $CH=CH_2$, $CH_2CH=CH_2$ or $CH_2CH_2CH=CH_2$. $R_5$ is H and $R_6$ is $COCH_3$. However, in this embodiment, $R_4$ is not H when $R_3$ is H.

In addition, these compounds may be formed into compositions for inhibiting influenza virus neuraminidase in humans or animals. Such compositions would comprise an effective amount of one or more of the above compounds based on the general formula I depicted above, its analogs, its pharmaceutically acceptable salts or derivatives, or mixtures thereof in a pharmaceutically acceptable carrier.

Thus in another preferred embodiment, this invention provides a method of inhibiting influenza virus neuraminidase. This method entails the step of administering to a subject (which may be a human or an animal) a pharmaceutically acceptable amount of a composition comprising effective amounts of a pharmaceutically acceptable carrier and a compound, its analogs, its pharmaceutically acceptable salts or derivatives, or mixtures thereof having the following formula:

GENERAL STRUCTURE I

[Chemical structure: benzene ring with substituents A (top), $R_1$ and $R_2$ (upper sides), $R_3$ and $R_4$ (lower sides), B (bottom) bearing $R_5$ and $R_6$]

In the compounds of this method, constituent A may be $CO_2H$, $CO_2CH_3$, $NO_2$, $SO_3H$ or $PO_3H_2$. In addition, B may be any of the following: CH, N, O and S. $R_1$ and $R_2$ each may be either H, $NO_2$, or $(CH_m)_nX_1$, where m is either 1 or 2, n is an integer from 0 to 4 and $X_1$ is one of the following: guanidino, OH, $NH_2$, SH, $NO_2$, F, Cl, Br, I, CN, $CF_3$, $CO_2H$, $SO_3H$ and $PO_3H_2$. $R_3$ and $R_4$ are each selected from the following: H, $(CH_o)_pX_2$, $(CH_o)_pCHX_2CH_2X_2$, $NH(CH_o)_pCHX_2CH_2X_2$, $NHCO(CH_o)_pCH_2X_2$ and $NHCO(CH_o)_pCHX_2CH_2X_2$ where o is either 1 or 2, p is an integer from 0 to 4 and $X_2$ is selected from the group consisting of H, guanidino, OH, $NH_2$, SH, $NO_2$, $CF_3$, $CO_2H$, $SO_3H$ and $PO_3H_2$. Also, $R_5$ is chosen from the following constituents: H, OH, $NH_2$, $(CH_k)_1X_3$, $CO(CH_k)_1X_3$, $SO(CH_k)_1X_3$ and $SO_2(CH_k)_1X_3$ where k is either 1 or 2, l is an integer from 0 to 4 and $X_3$ is guanidino, OH, $NH_2$, SH, $NO_2$, $CF_3$, $CO_2H$, $SO_3H$ or $PO_3H$. Finally, $R_6$ is H, $CH(OH)X_4$, $CH(NH_2)X_4$, $COX_4$, $SOX_4$, or $SO_2X_4$, where $X_4$ is H, $CH_3$, $CH_3CH_2$, $CH_3CHCH_3$, $CH_3CH_2CH_2$ or a halogen substituted analog of $X_4$.

In another preferable embodiment, this invention provides methods using the following class of influenza virus neuraminidase inhibitors, their analogs, their pharmaceutically acceptable salts and derivatives, and mixtures thereof having the same general formula I depicted above. In these inhibitors, constituent A is $CO_2H$ or $CO_2CH_3$ and B is either CH or N. Also, both $R_1$ and $R_2$ are H or $NO_2$. $R_3$ is H, OH, $NH_2$, guanidino, $NO_2$, F, Cl or Br. Furthermore, $R_4$ is further divided into constituent $QR_7$ where Q is selected from O, NH or $CH_2$ and $R_7$ is either H, $(CH_2)_oX_1$, $(CH_2)_oCHX_1CH_2X_1$, $CO(CH_2)_oCH_2X_1$ or $CO(CH_2)_oCHX_1CH_2X_1$ where o is an integer from 0 to 4 and $X_1$ is either H, guanidino, OH or $NH_2$. In addition, $R_5$ is $COCH_3$ and $R_6$ is $(CH_2)_pX_2$ where p is an integer from 0 to 4 and $X_2$ is OH, $NH_2$ or guanidino.

In yet another embodiment, this invention provides methods using a further class of influenza virus neuraminidase inhibitors, their analogs, their pharmaceutically acceptable salts and derivatives, and mixtures thereof having the same general formula as above. In this embodiment, A is either $CO_2H$ or $CO_2CH_3$, B is N, $R_1$ is H or $NO_2$ and $R_2$ is H or $NO_2$. In addition, $R_3$ is either H, OH, $NO_2$, $NH_2$, or guanidino. $R_4$ is selected from the group consisting of the following: H, OH, OAc, $NH_2$, guanidino, $NHCOCH_2OH$, $NHCOCH(OH)CH_2OH$, $NHCOCH_2NH_2$, $NHCOCH_2CH_2CH_2NH_2$, CHO, $CH_2OH$, $CH_2OAc$, $CH_2CH_2OH$, $CH_2CH_2CH_2OH$, $CH_2CH(OH)CH_2OH$, $CH_2CH_2CH_2CH_2OH$, $CH_2CH_2CH(OH)CH_2OH$, $CH_2I$, $CH=CH_2$, $CH_2CH=CH_2$ or $CH_2CH_2CH=CH_2$. $R_5$ is H and $R_6$ is $COCH_3$.

TABLE 6

4-(acetylamino)-3-hydroxy-5-nitrobenzoic acid
General Displacement Parameter Expressions-B's

| NAME | $B_{11}$ | $B_{22}$ | $B_{33}$ | $B_{12}$ | $B_{13}$ | $B_{23}$ | $B_{eq}$ |
|------|----------|----------|----------|----------|----------|----------|----------|
| O3   | 4.69(5)  | 6.80(6)  | 3.01(5)  | 3.79(4)  | 1.80(4)  | 3.01(4)  | 4.16(3)  |
| O5[1]| 6.12(6)  | 6.89(8)  | 4.70(6)  | 3.38(5)  | 3.10(5)  | 2.63(6)  | 5.26(4)  |
| O5   | 4.85(6)  | 4.52(6)  | 4.45(6)  | 2.02(5)  | 1.61(5)  | 2.64(5)  | 4.41(4)  |
| O7   | 5.37(6)  | 6.04(6)  | 1.75(4)  | 3.48(4)  | 0.80(4)  | 1.48(4)  | 4.16(4)  |
| O9   | 5.45(6)  | 6.61(6)  | 5.61(6)  | 3.91(4)  | 2.22(5)  | 4.45(5)  | 5.15(4)  |
| O9[1]| 4.99(6)  | 8.44(7)  | 6.28(7)  | 4.41(5)  | 2.25(5)  | 5.33(5)  | 5.71(4)  |
| N4   | 3.77(6)  | 4.19(6)  | 1.67(5)  | 2.39(4)  | 0.58(4)  | 1.51(4)  | 3.04(4)  |
| N5   | 3.53(6)  | 4.97(7)  | 2.54(5)  | 2.00(5)  | 0.91(4)  | 1.86(5)  | 3.54(4)  |
| C1   | 3.08(7)  | 3.07(6)  | 2.03(6)  | 1.39(5)  | −0.06(5) | 0.93(5)  | 2.92(4)  |
| C2   | 3.62(7)  | 3.46(7)  | 1.84(6)  | 1.52(5)  | 0.31(5)  | 1.20(5)  | 3.06(4)  |
| C3   | 3.14(6)  | 3.74(7)  | 1.71(6)  | 1.75(5)  | 0.43(5)  | 1.11(5)  | 2.84(4)  |
| C4   | 3.11(6)  | 3.14(6)  | 1.48(6)  | 1.52(5)  | 0.11(5)  | 1.01(5)  | 2.66(4)  |
| C5   | 3.26(7)  | 3.57(7)  | 2.00(6)  | 1.54(5)  | 0.44(5)  | 1.19(5)  | 2.98(4)  |
| C6   | 2.98(7)  | 3.75(7)  | 2.48(7)  | 1.61(5)  | 0.24(5)  | 1.13(6)  | 3.17(4)  |
| C7   | 3.34(7)  | 3.78(7)  | 1.66(6)  | 1.65(5)  | 0.25(5)  | 1.27(5)  | 2.97(4)  |
| C8   | 4.48(8)  | 4.72(7)  | 2.55(7)  | 2.61(6)  | 0.42(6)  | 1.88(6)  | 3.86(5)  |
| C9   | 3.52(7)  | 3.52(7)  | 2.92(7)  | 1.69(5)  | 0.32(5)  | 1.53(5)  | 3.40(5)  |

The form of the anisotropic displacement parameter is: $\exp[-0.25\{h^2 a^{*2} B_{11} + k^{2} b^{*2} B_{22} + l^2 c^{*2} B_{33} + 2hka^* b^* B_{12} + 2hla^* c^* B_{13} + 2klb^* c^* B_{23}\}]$ where $a^*$, $b^*$, and $c^*$ are reciprocal lattice constants.

TABLE 7

4-(acetylamino)-3-hydroxy-5-nitrobenzoic acid
General Displacement Parameter Expressions - U's

| NAME | $U_{11}$ | $U_{22}$ | $U_{33}$ | $U_{12}$ | $U_{13}$ | $U_{23}$ |
|------|----------|----------|----------|----------|----------|----------|
| O3   | 0.0594(6)| 0.0861(8)| 0.0382(6)| 0.0481(5)| 0.0227(5)| 0.0381(5)|
| O5[1]| 0.0775(8)| 0.087(1) | 0.0595(7)| 0.0428(7)| 0.0393(6)| 0.0333(7)|
| O5   | 0.0614(8)| 0.0572(7)| 0.0564(8)| 0.0255(6)| 0.0204(6)| 0.0334(6)|
| O7   | 0.0680(8)| 0.0765(8)| 0.0222(6)| 0.0441(6)| 0.0102(5)| 0.0187(6)|
| O9   | 0.0690(8)| 0.0837(7)| 0.0710(8)| 0.0495(6)| 0.0281(6)| 0.0563(6)|
| O9[1]| 0.0632(8)| 0.1068(8)| 0.0796(9)| 0.0559(6)| 0.0285(7)| 0.0675(7)|
| N4   | 0.0478(7)| 0.0530(7)| 0.0212(6)| 0.0302(5)| 0.0073(5)| 0.0192(6)|
| N5   | 0.0447(8)| 0.0629(9)| 0.0322(7)| 0.0253(6)| 0.0116(6)| 0.0235(6)|
| C1   | 0.0389(9)| 0.0389(8)| 0.0257(8)| 0.0176(6)| −0.0008(7)| 0.0118(7)|
| C2   | 0.0458(9)| 0.0438(9)| 0.0234(7)| 0.0193(7)| 0.0039(7)| 0.0152(7)|
| C3   | 0.0398(8)| 0.0474(8)| 0.0216(7)| 0.0221(6)| 0.0054(6)| 0.0141(7)|
| C4   | 0.0394(8)| 0.0398(8)| 0.0187(7)| 0.0192(6)| 0.0014(6)| 0.0128(6)|
| C5   | 0.0413(9)| 0.0452(9)| 0.0254(7)| 0.0195(7)| 0.0056(6)| 0.0150(7)|
| C6   | 0.0377(8)| 0.0475(9)| 0.0314(9)| 0.0204(7)| 0.0030(7)| 0.0143(7)|
| C7   | 0.0423(9)| 0.0479(9)| 0.0210(7)| 0.0209(7)| 0.0032(6)| 0.0161(6)|
| C8   | 0.057(1) | 0.060(1) | 0.0323(9)| 0.0331(7)| 0.0053(8)| 0.0238(8)|
| C9   | 0.0446(9)| 0.0446(9)| 0.0370(9)| 0.0214(7)| 0.0040(7)| 0.0194(7)|

The form of the anisotropic displacement parameter is: $\exp[-2\pi^2\{h^2 a^{*2} U_{11} + k^2 b^{*2} U_{22} + l^2 c^{*2} U_{33} + 2hka^* b^* U_{12} + 2hla^* c^* U_{13} + 2klb^* c^* U_{23}\}]$ where $a^*$, $b^*$, and $c^*$ are reciprocal lattice constants.

TABLE 8

4-(acetylamino)-3-hydroxy-5-nitrobenzoic acid
Root-Mean-Square Amplitudes of Anisotropic Displacement in Angstroms

| ATOM | MIN. | INT'MED. | MAX. |
|------|------|----------|------|
| O3   | 0.140| 0.210    | 0.307|
| O5[1]| 0.211| 0.245    | 0.308|
| O5   | 0.175| 0.251    | 0.272|
| O7   | 0.132| 0.222    | 0.303|
| O9   | 0.142| 0.262    | 0.326|
| O9[1]| 0.143| 0.258    | 0.360|
| N4   | 0.109| 0.205    | 0.248|
| N5   | 0.151| 0.218    | 0.254|
| C1   | 0.126| 0.197    | 0.237|
| C2   | 0.127| 0.210    | 0.236|
| C3   | 0.126| 0.202    | 0.226|
| C4   | 0.108| 0.197    | 0.225|
| C5   | 0.137| 0.212    | 0.223|
| C6   | 0.142| 0.217    | 0.230|
| C7   | 0.116| 0.217    | 0.229|
| C8   | 0.126| 0.241    | 0.269|
| C9   | 0.141| 0.218    | 0.249|

TABLE 13

Structure Amplitudes for 4-(acetylamino)-3-hydroxy-5-nitrobenzoic acid
Values of 10*Fobs and 10*Fcalc

| H | K | L | Fobs | Fcalc | SigF | H | K | L | Fobs | Fcalc | SigF | H | K | L | Fobs | Fcalc | SigF |
|---|---|---|---|---|---|---|---|---|---|---|---|---|---|---|---|---|---|
| -8 | -1 | 3 | 44 | 40 | 1 | -8 | 2 | 2 | 48 | 49 | 1 | -7 | -3 | 4 | 13 | 17 | 1 | -7 | -3 | 4 | 24 | 24 | 1 |
| -8 | -1 | 4 | 25 | 22 | 1 | -8 | 2 | 5 | 16 | 12 | 1 | -7 | -3 | 1 | 27 | 26 | 1 | -7 | -3 | 6 | 27 | 22 | 1 |
| -8 | 0 | 1 | 16 | 16 | 1 | -8 | 3 | 1 | 10 | 7 | 1 | -7 | -3 | 3 | 42 | 41 | 1 | -7 | -2 | 2 | 25 | 22 | 1 |
| -8 | 0 | 2 | 17 | 18 | 1 | -8 | 3 | 2 | 15 | 13 | 1 | -7 | -2 | 4 | 26 | 25 | 1 | -7 | -2 | 3 | 11 | 11 | 1 |
| -8 | 0 | 3 | 23 | 19 | 1 | -8 | 3 | 3 | 72 | 76 | 1 | -7 | -2 | 2 | 31 | 33 | 1 | -7 | -2 | 5 | 14 | 11 | 1 |
| -8 | 0 | 5 | 22 | 17 | 1 | -8 | 3 | 5 | 12 | 9 | 1 | -7 | -2 | 3 | 12 | 11 | 1 | -7 | -2 | 6 | 43 | 36 | 1 |
| -8 | -1 | 1 | 10 | 11 | 1 | -8 | 3 | 1 | 26 | 26 | 1 | -7 | -2 | 1 | 47 | 45 | 1 | -7 | 7 | 1 | 71 | 69 | 1 |
| -8 | -1 | 2 | 86 | 89 | 1 | -8 | 4 | 2 | 63 | 65 | 1 | -7 | 8 | 2 | 36 | 31 | 1 | -7 | 7 | 2 | 48 | 47 | 1 |
| -8 | -1 | 3 | 11 | 11 | 1 | -8 | 4 | 4 | 13 | 7 | 1 | -7 | 8 | 1 | 12 | 13 | 1 | -7 | 7 | 3 | 23 | 23 | 1 |
| -8 | -1 | 4 | 45 | 42 | 1 | -8 | 4 | 5 | 27 | 25 | 1 | -7 | -3 | 2 | 9 | 8 | 1 | -7 | 7 | 5 | 14 | 12 | 1 |
| -8 | -1 | 5 | 10 | 8 | 1 | -8 | 4 | 3 | 12 | 11 | 1 | -7 | -3 | 3 | 23 | 19 | 1 | -7 | 8 | 1 | 35 | 34 | 1 |
| -8 | 2 | 1 | 42 | 41 | 1 | -8 | 5 | 5 | 12 | 15 | 1 | -7 | 8 | 2 | 16 | 11 | 1 | -7 | 8 | 2 | 21 | 19 | 1 |
| -8 | 2 | 3 | 10 | 7 | 1 | -8 | 5 | 3 | 30 | 30 | 1 | -7 | 8 | 3 | 14 | 14 | 1 | -7 | 8 | 4 | 29 | 27 | 1 |
| -7 | -3 | 4 | 23 | 24 | 1 | -7 | 3 | 6 | 64 | 57 | 1 | -6 | 8 | 4 | 19 | 17 | 1 | -7 | 8 | 5 | 7 | 4 | 1 |
| -7 | -3 | 1 | 53 | 54 | 1 | -7 | 3 | 1 | 41 | 44 | 1 | -6 | 8 | 1 | 59 | 56 | 1 | -7 | 9 | 1 | 175 | 178 | 1 |
| -7 | 9 | 2 | 38 | 34 | 1 | -7 | 4 | 2 | 65 | 65 | 1 | -6 | 9 | 2 | 29 | 29 | 1 | -7 | 9 | 2 | 164 | 158 | 1 |
| -7 | 9 | 1 | 10 | 9 | 1 | -7 | 4 | 3 | 57 | 62 | 1 | -6 | 9 | 3 | 87 | 87 | 1 | -7 | 9 | 4 | 10 | 8 | 1 |
| -7 | 10 | 2 | 11 | 12 | 1 | -7 | 4 | 4 | 83 | 89 | 1 | -6 | 10 | 4 | 16 | 14 | 1 | -7 | 10 | 1 | 25 | 28 | 1 |
| -7 | 10 | 2 | 13 | 12 | 1 | -7 | 4 | 5 | 43 | 35 | 1 | -6 | 10 | 5 | 50 | 48 | 1 | -7 | 10 | 2 | 69 | 68 | 1 |
| -7 | -6 | 3 | 31 | 29 | 1 | -7 | 4 | 6 | 17 | 19 | 1 | -6 | 10 | 1 | 26 | 29 | 1 | -7 | 10 | 3 | 50 | 49 | 1 |
| -7 | -6 | 5 | 14 | 12 | 1 | -7 | 5 | 2 | 23 | 23 | 1 | -6 | 10 | 2 | 11 | 8 | 1 | -7 | 10 | 2 | 89 | 87 | 1 |
| -7 | -6 | 1 | 87 | 83 | 1 | -7 | 5 | 3 | 34 | 35 | 1 | -6 | -9 | 4 | 19 | 20 | 1 | -7 | -9 | 2 | 16 | 16 | 1 |
| -7 | -5 | 2 | 90 | 84 | 1 | -7 | 5 | 3 | 66 | 68 | 1 | -6 | -9 | 1 | 64 | 63 | 1 | -7 | -9 | 3 | 15 | 14 | 1 |
| -7 | -5 | 3 | 11 | 11 | 1 | -7 | 5 | 5 | 9 | 9 | 1 | -6 | -9 | 2 | 9 | 11 | 1 | -7 | -9 | 4 | 31 | 24 | 1 |
| -7 | -5 | 5 | 12 | 9 | 1 | -7 | 5 | 6 | 13 | 9 | 1 | -6 | -8 | 2 | 27 | 22 | 1 | -7 | -9 | 4 | 51 | 49 | 1 |
| -7 | -5 | 1 | 21 | 21 | 1 | -7 | 6 | 1 | 29 | 33 | 1 | -6 | -8 | 3 | 12 | 11 | 1 | -7 | -8 | 5 | 27 | 27 | 1 |
| -7 | -4 | 2 | 50 | 41 | 1 | -7 | 6 | 2 | 23 | 26 | 1 | -6 | -8 | 4 | 13 | 10 | 1 | -7 | -8 | 6 | 12 | 11 | 1 |
| -7 | -4 | 3 | 78 | 73 | 1 | -7 | 6 | 3 | 62 | 61 | 1 | -6 | -8 | 5 | 53 | 52 | 1 | -7 | -8 | 2 | 13 | 13 | 1 |
| -7 | -4 | 4 | 16 | 12 | 1 | -7 | 6 | 4 | 67 | 68 | 1 | -6 | 0 | 1 | 31 | 29 | 1 | -6 | -8 | 3 | 34 | 35 | 1 |
| -7 | -4 | 5 | 28 | 24 | 1 | -7 | 6 | 7 | 58 | 56 | 1 | -6 | 0 | 2 | 10 | 9 | 1 | -6 | 8 | 5 | 70 | 69 | 1 |
| -7 | -4 | 6 | 24 | 21 | 1 | -7 | 6 | 2 | 29 | 32 | 1 | -6 | 0 | 4 | 12 | 9 | 1 | -6 | 8 | 6 | 21 | 22 | 1 |
| -7 | -3 | 3 | 24 | 21 | 1 | -7 | 7 | 4 | 21 | 20 | 1 | -6 | 0 | 1 | 21 | 24 | 1 | -6 | -1 | 1 | 19 | 18 | 1 |
| -7 | -3 | 4 | 93 | 89 | 1 | -7 | 7 | 5 | 78 | 85 | 1 | -6 | -1 | 2 | 10 | 10 | 1 | -6 | -1 | 2 | 19 | 16 | 1 |
| -7 | -3 | 5 | 100 | 98 | 1 | -7 | 7 | 6 | 58 | 55 | 1 | -6 | -1 | 3 | 23 | 22 | 1 | -6 | -1 | 4 | 37 | 35 | 1 |
| -7 | -3 | 5 | 44 | 38 | 1 | -7 | 7 | 1 | 75 | 69 | 1 | -6 | -1 | 4 | 88 | 84 | 1 | -6 | -1 | 5 | 9 | 11 | 1 |
| -7 | -3 | 6 | 19 | 14 | 1 | -7 | 7 | 2 | 35 | 29 | 1 | -6 | -1 | 2 | 22 | 20 | 1 | -6 | 6 | 6 | 40 | 41 | 1 |
| -7 | -2 | 2 | 16 | 13 | 1 | -7 | 7 | 3 | 19 | 23 | 1 | -6 | 2 | 3 | 62 | 58 | 1 | -6 | 6 | 6 | 32 | 3 | 1 |
| -7 | -2 | 3 | 9 | 10 | 1 | -7 | 8 | 1 | 41 | 42 | 1 | -6 | 2 | 4 | 29 | 27 | 1 | -6 | -2 | 7 | 12 | 13 | 1 | 12 |
| -7 | -2 | 4 | 19 | 18 | 1 | -7 | 8 | 2 | 76 | 74 | 1 | -6 | 2 | 5 | 13 | 11 | 1 | -6 | -2 | 8 | 30 | 27 | 1 |
| -7 | -2 | 5 | 77 | 75 | 1 | -7 | 8 | 3 | 46 | 42 | 1 | -6 | -3 | 6 | 13 | 17 | 1 | -6 | -2 | 1 | 137 | 154 | 1 |
| -7 | -2 | 6 | 23 | 20 | 1 | -7 | 8 | 4 | 16 | 15 | 1 | -6 | -3 | 7 | 66 | 64 | 1 | -6 | -2 | 2 | 64 | 61 | 1 |
| -7 | -2 | 7 | 33 | 31 | 1 | -7 | 8 | 5 | 70 | 69 | 1 | -6 | -3 | 2 | 28 | 26 | 1 | -6 | -2 | 3 | 49 | 49 | 1 |
| -7 | -1 | 2 | 16 | 16 | 1 | -7 | 9 | 2 | 32 | 36 | 1 | -6 | -3 | 3 | 37 | 33 | 1 | -6 | -2 | 4 | 187 | 195 | 1 |
| -7 | -1 | 3 | 64 | 67 | 1 | -7 | 9 | 4 | 108 | 112 | 1 | -6 | -3 | 4 | 10 | 10 | 1 | -6 | -2 | 5 | 37 | 33 | 1 | 2 |
| -7 | -1 | 3 | 26 | 27 | 1 | -7 | 10 | 5 | 25 | 20 | 1 | -6 | 2 | 5 | 25 | 20 | 1 | -6 | -1 | 6 | 123 | 115 | 1 |
| -7 | -1 | 4 | 144 | 144 | 1 | -7 | 10 | 6 | 28 | 26 | 1 | -6 | 2 | 6 | 46 | 48 | 1 | -6 | -1 | 7 | 47 | 47 | 1 |
| -7 | -1 | 5 | 61 | 63 | 1 | | | | | | | | | | | | | | | | | | |

TABLE 13-continued

Structure Amplitudes for 4-(acetylamino)-3-hydroxy-5-nitrobenzoic acid
Values of 10*Fobs and 10*Fcalc

| H | K | L | Fobs | Fcalc | SigF | H | K | L | Fobs | Fcalc | SigF | H | K | L | Fobs | Fcalc | SigF |
|---|---|---|------|-------|------|---|---|---|------|-------|------|---|---|---|------|-------|------|
| -6 | -1 | 6 | 55 | 47 | 1 | -6 | 2 | 7 | 41 | 33 | 1 | -5 | -1 | 8 | 37 | 36 | 1 |
| -6 | -1 | 7 | 15 | 16 | 1 | -6 | 3 | 1 | 52 | 53 | 1 | -5 | 0 | 1 | 30 | 24 | 1 |
| -7 | -1 | 1 | 38 | 39 | 1 | -6 | 3 | 2 | 93 | 105 | 1 | -5 | 0 | 2 | 88 | 90 | 1 |
| -7 | -1 | 2 | 31 | 31 | 2 | -6 | 3 | 3 | 45 | 51 | 1 | -5 | 0 | 3 | 26 | 30 | 1 |
| -7 | -1 | 3 | 43 | 38 | 1 | -6 | 3 | 4 | 39 | 42 | 1 | -5 | 0 | 4 | 80 | 87 | 1 |
| -7 | -1 | 4 | 49 | 41 | 1 | -6 | 3 | 5 | 12 | 9 | 1 | -5 | 0 | 5 | 249 | 252 | 1 |
| -7 | -1 | 5 | 14 | 11 | 1 | -6 | 3 | 6 | 14 | 11 | 1 | -5 | 0 | 6 | 102 | 100 | 1 |
| -7 | -1 | 6 | 65 | 66 | 1 | -6 | 3 | 7 | 15 | 15 | 1 | -5 | 0 | 7 | 62 | 59 | 1 |
| -7 | 0 | -1 | 48 | 51 | 1 | -6 | 4 | 2 | 35 | 40 | 1 | -5 | 1 | 1 | 21 | 19 | 1 |
| -7 | 0 | 2 | 31 | 28 | 2 | -6 | 4 | 4 | 59 | 65 | 1 | -5 | 1 | 3 | 75 | 75 | 1 |
| -7 | 0 | 3 | 49 | 45 | 1 | -6 | 5 | 1 | 87 | 97 | 1 | -5 | 1 | 4 | 43 | 41 | 1 |
| -7 | 0 | 4 | 22 | 20 | 1 | -6 | 5 | 2 | 92 | 95 | 1 | -5 | 1 | 5 | 80 | 81 | 1 |
| -7 | 0 | 5 | 10 | 9 | 1 | -6 | 5 | 3 | 46 | 46 | 2 | -5 | 1 | 6 | 59 | 55 | 1 |
| -7 | 0 | 6 | 41 | 48 | 1 | -6 | 5 | 4 | 59 | 55 | 1 | -5 | 1 | 7 | 30 | 28 | 1 |
| -7 | -1 | 2 | 42 | 44 | 2 | -6 | 5 | 5 | 15 | 16 | 1 | -5 | 1 | 8 | 17 | 17 | 1 |
| -7 | -1 | 4 | 57 | 57 | 1 | -6 | 5 | 6 | 106 | 117 | 1 | -5 | 2 | 1 | 8 | 8 | 2 |
| -7 | -1 | 5 | 51 | 45 | 1 | -6 | 6 | 1 | 16 | 17 | 1 | -5 | 2 | 2 | 7 | 2 | 1 |
| -7 | -1 | 6 | 54 | 50 | 1 | -6 | 6 | 2 | 24 | 23 | 1 | -5 | 2 | 3 | 115 | 120 | 1 |
| -7 | -1 | 7 | 10 | 9 | 1 | -6 | 6 | 3 | 93 | 90 | 1 | -5 | 2 | 4 | 36 | 36 | 1 |
| -7 | -2 | 2 | 99 | 104 | 1 | -6 | 6 | 4 | 40 | 41 | 1 | -5 | 2 | 5 | 59 | 62 | 1 |
| -7 | -2 | 3 | 82 | 84 | 1 | -6 | 6 | 5 | 132 | 142 | 2 | -5 | 2 | 6 | 228 | 222 | 1 |
| -7 | -2 | 5 | 34 | 34 | 1 | -6 | 6 | 6 | 11 | 10 | 1 | -5 | 2 | 7 | 48 | 43 | 1 |
| -7 | -2 | 6 | 25 | 26 | 1 | -6 | 7 | 1 | 75 | 76 | 1 | -5 | 3 | 1 | 112 | 123 | 1 |
| -7 | -2 | 7 | 63 | 68 | 1 | -6 | 7 | 2 | 39 | 39 | 1 | -5 | 3 | 2 | 93 | 97 | 1 |
| -7 | -3 | 1 | 14 | 18 | 1 | -6 | 7 | 4 | 16 | 14 | 1 | -5 | 3 | 3 | 16 | 22 | 1 |
| -7 | -3 | 2 | 32 | 31 | 2 | -6 | 7 | 5 | 51 | 49 | 1 | -5 | 3 | 4 | 29 | 33 | 1 |
| -7 | -3 | 3 | 79 | 73 | 1 | -6 | 8 | -1 | 15 | 14 | 2 | -5 | 3 | 4 | 57 | 58 | 1 |
| -7 | -3 | 4 | 13 | 11 | 1 | -4 | 3 | 6 | 70 | 78 | 1 | -5 | 3 | 5 | 12 | 11 | 1 |
| -7 | -3 | 6 | 72 | 73 | 1 | -4 | 4 | -1 | 64 | 62 | 1 | -5 | 3 | 6 | 199 | 191 | 1 |
| -7 | -4 | 1 | 49 | 53 | 1 | -4 | 4 | 2 | 47 | 52 | 2 | -5 | 4 | 4 | 38 | 37 | 1 |
| -7 | -4 | 2 | 22 | 22 | 2 | -4 | 4 | 3 | 44 | 44 | 1 | -5 | 4 | 5 | 34 | 31 | 1 |
| -7 | -4 | 5 | 21 | 20 | 1 | -4 | 4 | 5 | 125 | 122 | 1 | -5 | 4 | 6 | 27 | 12 | 1 |
| -7 | -4 | 6 | 21 | 21 | 1 | -4 | 4 | 6 | 93 | 91 | 1 | -5 | 5 | 1 | 10 | 7 | 1 |
| -7 | -4 | 7 | 32 | 34 | 1 | -4 | 5 | 1 | 30 | 30 | 1 | -5 | 5 | 2 | 67 | 72 | 1 |
| -7 | -5 | 1 | 23 | 20 | 2 | -4 | 5 | 2 | 33 | 32 | 1 | -5 | 6 | 1 | 9 | 8 | 2 |
| -7 | -5 | 2 | 31 | 30 | 1 | -4 | 5 | 3 | 130 | 131 | 2 | -5 | 6 | 2 | 24 | 25 | 1 |
| -7 | -5 | 5 | 91 | 95 | 1 | -4 | 5 | 4 | 15 | 12 | 1 | -5 | 6 | 3 | 32 | 28 | 1 |
| -7 | -5 | 6 | 15 | 16 | 1 | -4 | 5 | 5 | 13 | 9 | 1 | -5 | 6 | 4 | 13 | 10 | 1 |
| -7 | -5 | 7 | 98 | 102 | 1 | -4 | 5 | 6 | 117 | 122 | 1 | -5 | 6 | 5 | 34 | 30 | 1 |
| -7 | -4 | 2 | 33 | 31 | 1 | -4 | 6 | 2 | 57 | 60 | 1 | -5 | 6 | 6 | 76 | 81 | 1 |
| -7 | -4 | 4 | 53 | 34 | 1 | -4 | 6 | 3 | 66 | 67 | 1 | -5 | 7 | 2 | 74 | 70 | 1 |
| -7 | -4 | 5 | 29 | 20 | 1 | -4 | 6 | 4 | 13 | 11 | 1 | -5 | 7 | 3 | 81 | 83 | 1 |
| -7 | -4 | 6 | 33 | 26 | 2 | -4 | 6 | 5 | 83 | 85 | 1 | -5 | 7 | 4 | 86 | 80 | 1 |
| -7 | -4 | 7 | 65 | 65 | 1 | -4 | 7 | -1 | 79 | 84 | 1 | -5 | 7 | 5 | 61 | 58 | 1 |
| -7 | -3 | -1 | 30 | 31 | 1 | -4 | 7 | 2 | 47 | 47 | 1 | -5 | 8 | 1 | 15 | 14 | 1 |
| -7 | -3 | 1 | 108 | 120 | 1 | -4 | 7 | 3 | 79 | 83 | 1 | -5 | 8 | -1 | 131 | 129 | 1 |
| -7 | -3 | 3 | 12 | 12 | 2 | -4 | 7 | 4 | 21 | 21 | 2 | -5 | 8 | 3 | 27 | 23 | 2 |

TABLE 13-continued

Structure Amplitudes for 4-(acetylamino)-3-hydroxy-5-nitrobenzoic acid
Values of 10*Fobs and 10*Fcalc

| H | K | L | Fobs | Fcalc | SigF | H | K | L | Fobs | Fcalc | SigF | H | K | L | Fobs | Fcalc | SigF |
|---|---|---|------|-------|------|---|---|---|------|-------|------|---|---|---|------|-------|------|
| -4 | -3 | 4 | 50 | 57 | 1 | -4 | 7 | 5 | 14 | 15 | 1 | -3 | -9 | 3 | 65 | 59 | 1 | -3 | 8 | 5 | 45 | 43 | 1 |
| -4 | -3 | 5 | 39 | 41 | 1 | -4 | 8 | 1 | 86 | 88 | 1 | -3 | -9 | 4 | 13 | 15 | 1 | -3 | 9 | 1 | 41 | 40 | 1 |
| -4 | -3 | 7 | 54 | 53 | 1 | -4 | 8 | 2 | 16 | 17 | 1 | -3 | -9 | 5 | 10 | 11 | 1 | -3 | 9 | 2 | 82 | 83 | 1 |
| -4 | -3 | 8 | 18 | 15 | 1 | -4 | 8 | 3 | 65 | 63 | 1 | -3 | -8 | 1 | 56 | 58 | 1 | -3 | 10 | 2 | 57 | 55 | 1 |
| -4 | -2 | 1 | 16 | 16 | 1 | -4 | 8 | 4 | 64 | 65 | 1 | -3 | -8 | 2 | 53 | 50 | 1 | -3 | 10 | 3 | 10 | 10 | 1 |
| -4 | -2 | 2 | 75 | 79 | 1 | -4 | 8 | 5 | 18 | 17 | 1 | -3 | -8 | 3 | 30 | 29 | 1 | -3 | 10 | 4 | 14 | 14 | 1 |
| -4 | -2 | 4 | 31 | 26 | 1 | -4 | 9 | 1 | 96 | 94 | 1 | -3 | -8 | 4 | 32 | 34 | 1 | -3 | 11 | 1 | 70 | 66 | 1 |
| -4 | -2 | 5 | 43 | 44 | 1 | -4 | 9 | 2 | 13 | 9 | 1 | -3 | -8 | 6 | 10 | 12 | 1 | -3 | 12 | 1 | 27 | 26 | 1 |
| -4 | -2 | 7 | 24 | 21 | 1 | -4 | 9 | 3 | 42 | 43 | 1 | -3 | -7 | 1 | 15 | 16 | 1 | -3 | -11 | 3 | 13 | 15 | 1 |
| -4 | -2 | 8 | 9 | 9 | 1 | -4 | -3 | 8 | 11 | 10 | 1 | -3 | -7 | 2 | 17 | 17 | 1 | -3 | -11 | 4 | 7 | 10 | 1 |
| -4 | -1 | 1 | 116 | 115 | 1 | -3 | -3 | 1 | 82 | 83 | 1 | -3 | -7 | 3 | 11 | 8 | 1 | -3 | -10 | 2 | 25 | 22 | 1 |
| -4 | -1 | 2 | 128 | 142 | 1 | -3 | -3 | 2 | 14 | 14 | 1 | -3 | -7 | 4 | 11 | 13 | 1 | -3 | -10 | 3 | 12 | 12 | 1 |
| -4 | -1 | 3 | 23 | 25 | 1 | -3 | -3 | 3 | 124 | 129 | 1 | -3 | -7 | 5 | 19 | 21 | 1 | -3 | -10 | 4 | 10 | 3 | 1 |
| -4 | -1 | 4 | 49 | 57 | 1 | -3 | -3 | 4 | 57 | 61 | 1 | -3 | -6 | 1 | 35 | 38 | 1 | -3 | -10 | 5 | 45 | 43 | 1 |
| -4 | -1 | 5 | 97 | 98 | 1 | -3 | -3 | 5 | 29 | 32 | 2 | -3 | -6 | 2 | 41 | 42 | 1 | -3 | -9 | 1 | 22 | 21 | 1 |
| -4 | -1 | 6 | 63 | 60 | 1 | -3 | -3 | 7 | 52 | 56 | 1 | -3 | -6 | 3 | 109 | 111 | 2 | -3 | -9 | 2 | 31 | 32 | 1 |
| -4 | -1 | 8 | 23 | 27 | 1 | -3 | -3 | 8 | 45 | 45 | 1 | -3 | -6 | 4 | 61 | 59 | 1 | -3 | -9 | 5 | 74 | 75 | 1 |
| -4 | 0 | 1 | 24 | 25 | 1 | -3 | -2 | 1 | 92 | 99 | 1 | -3 | -6 | 6 | 12 | 13 | 1 | -3 | -9 | 6 | 49 | 49 | 1 |
| -4 | 0 | 3 | 53 | 53 | 1 | -3 | -2 | 3 | 78 | 81 | 1 | -3 | -6 | 5 | 29 | 32 | 2 | -3 | -8 | 1 | 59 | 64 | 1 |
| -4 | 0 | 4 | 114 | 114 | 1 | -3 | -2 | 4 | 63 | 56 | 1 | -3 | -5 | 4 | 47 | 57 | 1 | -3 | -8 | 2 | 15 | 15 | 1 |
| -4 | 0 | 5 | 65 | 63 | 1 | -3 | -2 | 5 | 34 | 35 | 1 | -3 | -5 | 5 | 35 | 40 | 1 | -3 | -8 | 4 | 91 | 92 | 1 |
| -4 | 0 | 6 | 44 | 41 | 1 | -3 | -2 | 6 | 40 | 38 | 1 | -3 | -5 | 6 | 22 | 24 | 2 | -3 | -8 | 5 | 31 | 28 | 1 |
| -4 | 0 | 7 | 98 | 122 | 1 | -3 | -2 | 7 | 81 | 89 | 1 | -3 | -4 | 1 | 116 | 128 | 1 | -3 | -8 | 6 | 22 | 22 | 1 |
| -4 | 0 | 8 | 101 | 109 | 1 | -3 | -2 | 8 | 32 | 36 | 1 | -3 | -4 | 2 | 79 | 84 | 1 | -3 | -8 | 7 | 22 | 25 | 1 |
| -4 | -1 | 5 | 40 | 41 | 1 | -3 | -1 | 2 | 9 | 7 | 1 | -3 | -4 | 3 | 93 | 99 | 1 | -3 | -7 | 1 | 116 | 123 | 1 |
| -4 | -1 | 6 | 20 | 19 | 1 | -3 | -1 | 4 | 70 | 70 | 2 | -3 | -4 | 4 | 36 | 33 | 1 | -3 | -7 | 2 | 41 | 39 | 1 |
| -4 | -1 | 8 | 233 | 259 | 1 | -3 | -1 | 6 | 87 | 84 | 1 | -3 | -4 | 5 | 42 | 44 | 1 | -3 | -7 | 3 | 40 | 43 | 1 |
| -4 | 2 | 2 | 14 | 15 | 1 | -3 | -1 | 7 | 27 | 30 | 1 | -3 | -4 | 7 | 33 | 29 | 1 | -3 | -7 | 4 | 23 | 23 | 1 |
| -4 | 2 | 3 | 48 | 44 | 1 | -3 | -1 | 8 | 79 | 83 | 1 | -3 | -4 | 8 | 66 | 70 | 1 | -3 | -7 | 7 | 43 | 43 | 1 |
| -4 | 2 | 4 | 54 | 53 | 1 | -3 | 0 | 4 | 14 | 16 | 1 | -3 | -3 | 1 | 18 | 15 | 1 | -3 | -6 | 4 | 147 | 147 | 1 |
| -4 | 2 | 5 | 33 | 29 | 1 | -3 | 0 | 5 | 98 | 96 | 1 | -3 | -3 | 4 | 46 | 49 | 1 | -3 | -6 | 5 | 22 | 23 | 1 |
| -4 | 2 | 6 | 132 | 131 | 1 | -3 | 0 | 6 | 129 | 130 | 1 | -3 | -3 | 5 | 52 | 52 | 1 | -3 | -6 | 6 | 63 | 64 | 1 |
| -4 | 2 | 7 | 19 | 19 | 1 | -3 | 0 | 7 | 31 | 34 | 1 | -3 | -3 | 6 | 58 | 64 | 1 | -3 | -6 | 1 | 10 | 6 | 1 |
| -4 | 2 | 8 | 48 | 45 | 1 | -3 | 0 | 8 | 45 | 48 | 2 | -3 | -3 | 7 | 25 | 25 | 1 | -3 | -6 | 2 | 48 | 52 | 1 |
| -4 | 3 | 2 | 241 | 262 | 1 | -3 | 1 | 2 | 171 | 184 | 1 | -3 | -3 | 1 | 181 | 194 | 1 | -3 | -6 | 3 | 152 | 151 | 1 |
| -4 | 3 | 3 | 191 | 188 | 1 | -3 | 1 | 3 | 127 | 135 | 1 | -3 | -3 | 2 | 39 | 37 | 1 | -3 | -6 | 4 | 109 | 106 | 1 |
| -4 | 3 | 4 | 95 | 96 | 1 | -3 | 1 | 4 | 71 | 75 | 1 | -3 | -3 | 3 | 52 | 56 | 1 | -3 | -6 | 5 | 100 | 95 | 1 |
| -4 | 3 | 5 | 15 | 12 | 1 | -3 | 1 | 5 | 37 | 39 | 1 | -3 | -3 | 4 | 49 | 49 | 1 | -3 | -6 | 6 | 69 | 71 | 1 |
| -4 | 3 | 7 | 10 | 14 | 1 | -3 | 1 | 6 | 52 | 48 | 2 | -3 | -3 | 5 | 28 | 29 | 1 | -3 | 6 | 1 | 39 | 36 | 1 |
| -4 | -5 | 1 | 41 | 43 | 1 | -3 | 1 | 7 | 30 | 32 | 1 | -3 | -3 | 6 | 33 | 32 | 1 | -3 | 6 | 2 | 44 | 48 | 1 |
| -4 | -4 | 2 | 159 | 163 | 1 | -3 | 2 | 5 | 74 | 74 | 1 | -3 | -3 | 7 | 60 | 63 | 1 | -3 | 6 | 3 | 61 | 57 | 1 |
| -4 | -4 | 3 | 216 | 223 | 1 | -3 | 2 | 6 | 43 | 42 | 2 | -3 | -3 | 8 | 239 | 247 | 1 | -3 | 6 | 4 | 18 | 13 | 1 |
| -4 | -4 | 4 | 76 | 75 | 1 | -3 | 2 | 7 | 85 | 87 | 1 | -3 | -2 | 2 | 23 | 32 | 1 | -3 | 7 | 2 | 22 | 21 | 1 |
| -4 | -4 | 5 | 115 | 117 | 1 | -3 | 2 | 8 | 26 | 28 | 1 | -3 | -2 | 4 | 144 | 147 | 1 | -3 | 7 | 3 | 18 | 18 | 1 |
| -4 | -4 | 6 | 72 | 80 | 2 | -3 | 3 | 4 | 193 | 199 | 1 | -3 | -2 | 5 | 89 | 93 | 1 | -3 | 7 | 5 | 28 | 31 | 2 |
| -2 | -4 | 6 | 43 | 43 | 1 | -3 | 3 | 5 | 204 | 206 | 1 | -3 | -2 | 6 | 46 | 52 | 2 | -3 | 7 | 2 | 31 | 24 | 1 |
| | | | | | | -3 | 3 | 6 | 90 | 83 | 2 | -3 | -2 | 7 | 33 | 37 | 1 | -3 | -6 | 2 | 71 | 72 | 1 |

TABLE 13-continued

Structure Amplitudes for 4-(acetylamino)-3-hydroxy-5-nitrobenzoic acid
Values of 10*Fobs and 10*Fcalc

| H | K | L | Fobs | Fcalc | SigF | H | K | L | Fobs | Fcalc | SigF | H | K | L | Fobs | Fcalc | SigF |
|---|---|---|------|-------|------|---|---|---|------|-------|------|---|---|---|------|-------|------|
| -2 | -4 | 7 | 20 | 21 | 2 | -2 | -1 | 6 | 69 | 70 | 1 | -1 | -3 | 3 | 118 | 121 | 1 |
| -2 | -4 | 8 | 23 | 27 | 1 | -2 | -1 | 7 | 34 | 34 | 1 | -1 | -3 | 4 | 205 | 206 | 1 |
| -2 | -3 | 2 | 66 | 61 | 1 | -2 | -1 | 8 | 22 | 20 | 1 | -1 | -3 | 5 | 495 | 488 | 1 |
| -2 | -3 | 3 | 271 | 272 | 1 | -2 | 0 | 2 | 28 | 25 | 1 | -1 | -3 | 6 | 91 | 89 | 1 |
| -2 | -3 | 5 | 87 | 85 | 1 | -2 | 0 | 3 | 12 | 9 | 1 | -1 | -3 | 7 | 83 | 85 | 1 |
| -2 | -3 | 6 | 16 | 21 | 1 | -2 | 0 | 5 | 65 | 68 | 2 | -1 | -3 | 1 | 72 | 71 | 1 |
| -2 | -3 | 8 | 23 | 26 | 1 | -2 | 0 | 6 | 29 | 26 | 1 | -1 | -3 | 2 | 22 | 22 | 1 |
| -2 | -2 | 2 | 63 | 58 | 1 | -2 | 0 | 7 | 16 | 18 | 1 | -1 | -3 | 4 | 39 | 40 | 1 |
| -2 | -2 | 3 | 181 | 186 | 1 | -2 | 1 | 3 | 125 | 116 | 1 | -1 | -3 | 5 | 330 | 344 | 1 |
| -2 | -2 | 4 | 163 | 170 | 1 | -2 | 1 | 4 | 53 | 50 | 1 | -1 | -3 | 6 | 34 | 34 | 1 |
| -2 | -2 | 6 | 51 | 53 | 1 | -2 | 1 | 5 | 138 | 132 | 1 | -1 | -2 | 4 | 47 | 49 | 1 |
| -2 | 5 | 1 | 82 | 91 | 1 | -2 | -2 | 6 | 65 | 63 | 1 | -1 | -2 | 5 | 29 | 33 | 1 |
| -2 | 5 | 2 | 31 | 29 | 1 | -2 | -2 | 8 | 19 | 19 | 1 | -1 | -2 | 6 | 47 | 54 | 1 |
| -2 | 6 | 3 | 25 | 26 | 1 | -2 | -1 | 2 | 31 | 35 | 1 | -1 | -2 | 8 | 356 | 382 | 1 |
| -2 | 6 | 4 | 71 | 72 | 1 | -2 | -1 | 3 | 101 | 106 | 1 | -1 | -2 | 2 | 425 | 410 | 1 |
| -2 | 6 | 6 | 44 | 47 | 1 | -2 | -1 | 5 | 96 | 100 | 1 | -1 | -2 | 3 | 267 | 245 | 1 |
| -2 | 6 | 1 | 36 | 36 | 1 | -2 | -1 | 6 | 68 | 70 | 1 | -1 | -2 | 4 | 25 | 29 | 1 |
| -2 | 7 | 2 | 70 | 69 | 1 | -2 | -1 | 1 | 19 | 21 | 1 | -1 | -2 | 5 | 40 | 38 | 1 |
| -2 | 7 | 5 | 16 | 9 | 1 | -2 | -1 | 2 | 20 | 21 | 1 | -1 | -2 | 6 | 30 | 29 | 1 |
| -2 | 8 | 1 | 55 | 56 | 1 | -2 | -1 | 3 | 79 | 84 | 1 | -1 | -2 | 8 | 293 | 319 | 1 |
| -2 | 8 | 3 | 125 | 125 | 1 | -2 | -1 | 4 | 20 | 20 | 1 | -1 | -2 | 2 | 23 | 14 | 1 |
| -2 | 8 | 4 | 58 | 55 | 1 | -2 | -1 | 5 | 24 | 20 | 1 | -1 | 0 | 3 | 92 | 90 | 1 |
| -2 | 8 | 5 | 46 | 46 | 1 | -2 | -1 | 6 | 92 | 89 | 1 | -1 | 0 | 4 | 150 | 148 | 1 |
| -2 | 8 | 6 | 56 | 55 | 1 | -2 | -1 | 7 | 11 | 12 | 1 | -1 | 0 | 5 | 31 | 29 | 1 |
| -2 | 8 | 1 | 23 | 22 | 2 | -2 | -1 | 1 | 57 | 57 | 1 | -1 | 0 | 6 | 51 | 52 | 1 |
| -2 | 9 | 2 | 39 | 36 | 1 | -2 | -1 | 2 | 79 | 75 | 1 | -1 | 0 | 7 | 90 | 90 | 1 |
| -2 | 9 | 3 | 19 | 16 | 1 | -2 | -1 | 3 | 74 | 76 | 1 | -1 | 1 | 3 | 142 | 142 | 1 |
| -2 | 9 | 4 | 33 | 30 | 1 | -2 | -1 | 4 | 100 | 97 | 1 | -1 | 1 | 5 | 191 | 187 | 1 |
| -2 | 9 | 5 | 18 | 20 | 2 | -2 | -1 | 5 | 78 | 83 | 1 | -1 | 1 | 7 | 112 | 111 | 1 |
| -2 | 10 | 2 | 27 | 23 | 1 | -2 | -1 | 6 | 31 | 33 | 1 | -1 | 2 | 2 | 47 | 47 | 1 |
| -2 | 10 | 3 | 17 | 16 | 1 | -2 | -1 | 7 | 33 | 36 | 1 | -1 | 2 | 3 | 36 | 38 | 1 |
| -2 | 10 | 4 | 15 | 15 | 1 | -2 | -1 | 1 | 71 | 65 | 1 | -1 | 2 | 4 | 77 | 79 | 1 |
| -2 | 10 | 5 | 33 | 34 | 1 | -2 | -1 | 2 | 46 | 49 | 1 | -1 | 2 | 5 | 233 | 231 | 1 |
| -2 | 11 | 2 | 25 | 27 | 1 | -2 | -1 | 3 | 12 | 11 | 1 | -1 | 2 | 6 | 76 | 74 | 1 |
| -2 | 11 | 3 | 74 | 74 | 1 | -2 | -1 | 4 | 64 | 65 | 1 | -1 | 3 | 1 | 35 | 36 | 1 |
| -2 | -11 | 1 | 20 | 18 | 2 | -2 | -1 | 5 | 37 | 38 | 1 | -1 | 3 | 3 | 35 | 34 | 1 |
| -2 | -10 | 2 | 56 | 57 | 1 | -2 | -1 | 2 | 147 | 146 | 1 | -1 | 3 | 5 | 48 | 51 | 1 |
| -2 | -10 | 3 | 98 | 97 | 1 | -2 | -1 | 3 | 58 | 58 | 1 | -1 | 3 | 6 | 146 | 153 | 1 |
| -2 | -10 | 5 | 9 | 7 | 1 | -2 | -1 | 4 | 85 | 90 | 1 | -1 | 3 | 1 | 8 | 10 | 2 |
| -2 | -9 | 2 | 9 | 9 | 1 | -2 | -1 | 5 | 15 | 11 | 1 | -1 | 3 | 3 | 76 | 66 | 1 |
| -2 | -9 | 3 | 59 | 60 | 1 | -2 | -1 | 6 | 60 | 64 | 1 | -1 | 4 | 4 | 83 | 84 | 1 |
| -2 | -9 | 4 | 91 | 94 | 1 | -2 | -1 | 7 | 14 | 19 | 1 | -1 | 4 | 5 | 157 | 159 | 1 |
| -2 | -9 | 5 | 33 | 34 | 1 | -2 | -1 | 2 | 117 | 117 | 1 | -1 | 4 | 7 | 32 | 37 | 1 |
| -2 | -9 | 6 | 67 | 66 | 1 | -2 | -1 | 3 | 151 | 151 | 1 | -1 | 4 | 2 | 112 | 109 | 1 |
| -2 | -8 | 1 | 43 | 45 | 1 | -2 | -1 | 4 | 45 | 44 | 1 | -1 | 4 | 3 | 130 | 133 | 1 |
| -2 | -8 | 2 | 29 | 28 | 1 | -2 | -1 | 5 | 34 | 30 | 2 | -1 | 4 | 5 | 42 | 43 | 1 |
| -1 | -8 | 2 | 59 | 58 | 1 | -1 | -6 | 6 | 63 | 67 | 1 | -1 | 4 | 6 | 28 | 32 | 1 |

TABLE 13-continued

Structure Amplitudes for 4-(acetylamino)-3-hydroxy-5-nitrobenzoic acid
Values of 10*Fobs and 10*Fcalc

| H | K | L | Fobs | Fcalc | SigF | H | K | L | Fobs | Fcalc | SigF | H | K | L | Fobs | Fcalc | SigF |
|---|---|---|------|-------|------|---|---|---|------|-------|------|---|---|---|------|-------|------|
| −1 | −8 | 3 | 120 | 122 | 1 | −1 | −5 | 1 | 48 | 49 | 1 | 1 | 9 | 2 | 89 | 92 | 1 |
| −1 | −8 | 4 | 85 | 84 | 1 | −1 | −5 | 2 | 87 | 91 | 1 | 1 | 9 | 3 | 108 | 105 | 1 |
| −1 | −8 | 5 | 61 | 63 | 1 | −1 | −5 | 3 | 21 | 28 | 1 | 1 | 10 | 1 | 69 | 68 | 1 |
| −1 | −8 | 6 | 44 | 46 | 1 | −1 | −5 | 4 | 54 | 55 | 1 | 1 | 10 | 2 | 19 | 21 | 1 |
| −1 | 11 | 2 | 14 | 18 | 1 | 0 | −5 | 5 | 50 | 54 | 1 | 1 | 11 | 0 | 62 | 70 | 1 |
| 0 | −12 | 1 | 65 | 67 | 1 | 0 | 6 | 6 | 37 | 36 | 2 | 1 | −11 | 1 | 44 | 46 | 1 |
| 0 | −12 | 2 | 41 | 41 | 1 | 0 | 6 | 0 | 11 | 9 | 1 | −1 | 0 | 6 | 390 | 383 | 1 |
| 0 | −12 | 3 | 13 | 13 | 1 | 0 | 7 | 2 | 82 | 79 | 1 | −1 | 0 | 7 | 221 | 224 | 1 |
| 0 | −11 | 1 | 16 | 16 | 1 | 0 | 7 | 4 | 59 | 60 | 2 | −1 | 0 | 2 | 36 | 38 | 1 |
| 0 | −11 | 2 | 16 | 13 | 1 | 0 | 7 | 5 | 12 | 13 | 1 | −1 | 0 | 3 | 15 | 13 | 1 |
| 0 | −11 | 3 | 70 | 70 | 1 | 0 | 7 | 1 | 13 | 9 | 1 | 1 | 0 | 4 | 28 | 28 | 1 |
| 0 | −11 | 4 | 30 | 28 | 1 | 0 | 8 | 2 | 30 | 28 | 2 | 1 | 0 | 5 | 17 | 11 | 1 |
| 0 | −10 | 2 | 139 | 138 | 1 | 0 | 8 | 4 | 26 | 29 | 1 | 1 | 5 | 0 | 155 | 161 | 1 |
| 0 | −10 | 3 | 127 | 126 | 1 | 0 | 8 | 0 | 14 | 16 | 1 | 1 | 5 | 1 | 143 | 142 | 1 |
| 0 | −10 | 4 | 48 | 48 | 1 | 0 | 9 | 0 | 50 | 50 | 1 | 1 | 5 | 2 | 23 | 22 | 1 |
| 0 | −10 | 5 | 15 | 16 | 1 | 0 | 10 | 0 | 25 | 21 | 1 | 1 | 5 | 3 | 29 | 27 | 1 |
| 0 | −10 | 6 | 61 | 65 | 1 | 0 | 11 | 0 | 33 | 30 | 1 | 1 | 6 | 0 | 97 | 89 | 1 |
| 0 | −9 | 1 | 23 | 25 | 1 | 0 | 11 | 1 | 26 | 28 | 1 | 1 | 6 | 1 | 30 | 34 | 1 |
| 0 | −9 | 2 | 23 | 24 | 1 | 0 | −12 | 0 | 29 | 25 | 1 | 1 | 6 | 2 | 158 | 161 | 9 |
| 0 | −9 | 3 | 80 | 78 | 1 | 0 | −12 | 2 | 17 | 18 | 1 | 1 | 6 | 4 | 73 | 78 | 2 |
| 0 | −9 | 4 | 203 | 19 | 1 | 0 | −12 | 3 | 24 | 23 | 1 | 1 | 6 | 5 | 25 | 27 | 1 |
| 0 | −9 | 5 | 87 | 91 | 1 | 0 | −11 | 0 | 42 | 41 | 3 | 1 | 7 | 0 | 31 | 30 | 4 |
| 0 | −8 | 1 | 105 | 111 | 1 | 0 | −11 | 1 | 23 | 23 | 1 | 1 | 7 | 2 | 34 | 32 | 1 |
| 0 | −8 | 2 | 62 | 63 | 1 | 0 | −11 | 2 | 25 | 22 | 1 | 1 | 7 | 3 | 57 | 59 | 1 |
| 0 | −8 | 3 | 154 | 149 | 1 | 0 | −11 | 3 | 41 | 43 | 1 | 1 | 7 | 4 | 104 | 112 | 3 |
| 0 | −8 | 4 | 203 | 202 | 1 | 0 | −10 | 0 | 68 | 68 | 4 | 1 | 8 | 0 | 34 | 29 | 1 |
| 0 | −8 | 5 | 95 | 96 | 1 | 0 | −10 | 1 | 14 | 11 | 1 | 1 | 8 | 2 | 10 | 4 | 1 |
| 0 | −8 | 6 | 17 | 18 | 1 | 0 | −10 | 2 | 20 | 17 | 1 | 1 | 8 | 3 | 23 | 20 | 2 |
| 0 | −7 | 1 | 141 | 151 | 1 | 0 | −10 | 4 | 96 | 97 | 1 | 1 | 8 | 4 | 53 | 59 | 1 |
| 0 | −7 | 2 | 16 | 11 | 1 | 0 | −10 | 5 | 25 | 23 | 1 | 1 | 9 | 0 | 18 | 18 | 1 |
| 0 | −7 | 3 | 50 | 53 | 1 | 0 | −9 | 0 | 14 | 15 | 2 | 1 | 9 | 2 | 12 | 12 | 3 |
| 0 | −7 | 4 | 195 | 193 | 1 | 0 | −9 | 3 | 12 | 4 | 1 | 1 | 10 | 0 | 10 | 12 | 2 |
| 0 | −7 | 5 | 277 | 275 | 2 | 0 | −9 | 4 | 125 | 127 | 1 | 1 | 11 | 1 | 13 | 12 | 1 |
| 0 | −7 | 6 | 36 | 39 | 1 | 0 | −9 | 5 | 50 | 48 | 1 | 1 | −12 | 2 | 25 | 22 | 1 |
| 0 | −7 | 7 | 21 | 21 | 1 | 0 | −9 | 6 | 21 | 21 | 1 | 1 | −12 | 0 | 31 | 29 | 1 |
| 0 | −6 | 1 | 96 | 104 | 1 | 0 | −8 | 0 | 14 | 17 | 1 | 1 | −11 | 0 | 29 | 27 | 1 |
| 0 | 2 | 1 | 1121 | 1131 | 1 | 0 | −8 | 1 | 94 | 98 | 6 | 1 | −11 | 1 | 20 | 22 | 1 |
| 0 | 2 | 2 | 29 | 34 | 3 | 0 | −8 | 2 | 71 | 69 | 1 | 1 | −11 | 3 | 15 | 14 | 1 |
| 0 | 2 | 3 | 17 | 17 | 1 | 0 | −8 | 4 | 61 | 61 | 2 | 1 | −11 | 4 | 12 | 10 | 1 |
| 0 | 2 | 5 | 15 | 16 | 1 | 0 | −8 | 5 | 35 | 38 | 2 | 1 | −10 | 0 | 49 | 50 | 1 |
| 0 | 2 | 6 | 32 | 36 | 1 | 0 | −8 | 6 | 37 | 33 | 2 | 1 | −10 | 1 | 28 | 28 | 1 |
| 0 | 3 | 1 | 256 | 264 | 1 | 0 | −7 | 0 | 88 | 94 | 1 | 1 | −10 | 3 | 31 | 30 | 2 |
| 0 | 3 | 2 | 221 | 211 | 1 | 0 | −7 | 1 | 17 | 16 | 7 | 1 | −10 | 4 | 302 | 303 | 1 |
| 0 | 3 | 3 | 296 | 295 | 1 | 0 | −7 | 2 | 217 | 213 | 1 | 1 | −10 | 5 | 45 | 46 | 1 |
| 0 | 3 | 4 | 139 | 130 | 1 | 0 | −7 | 3 | 59 | 57 | 1 | 1 | −10 | 6 | 71 | 68 | 1 |
| 0 | 3 | 5 | 71 | 68 | 1 | 0 | −7 | 4 | 19 | 14 | 1 | 1 | −10 | 0 | 77 | 74 | 1 |
| 0 | 3 | 5 | 118 | 116 | 1 | 0 | −7 | 1 | 127 | 121 | 1 | 1 | −9 | 1 | 112 | 103 | 1 |

TABLE 13-continued

Structure Amplitudes for 4-(acetylamino)-3-hydroxy-5-nitrobenzoic acid
Values of 10*Fobs and 10*Fcalc

| H | K | L | Fobs | Fcalc | SigF | H | K | L | Fobs | Fcalc | SigF | H | K | L | Fobs | Fcalc | SigF |
|---|---|---|------|-------|------|---|---|---|------|-------|------|---|---|---|------|-------|------|
| 0 | 4 | 0 | 159 | 163 | 4 | 1 | −7 | 4 | 256 | 249 | 1 | 2 | −4 | 3 | 27 | 27 | 1 |
| 0 | 4 | 1 | 171 | 166 | 1 | 1 | −7 | 7 | 27 | 35 | 1 | 2 | −4 | 4 | 101 | 94 | 1 |
| 0 | 4 | 2 | 344 | 345 | 1 | 1 | −6 | 0 | 24 | 24 | 3 | 2 | −4 | 5 | 179 | 167 | 1 |
| 0 | 4 | 3 | 31 | 26 | 1 | 1 | −6 | 1 | 358 | 336 | 1 | 2 | −5 | 0 | 22 | 22 | 1 |
| 0 | 4 | 4 | 11 | 10 | 1 | 1 | −6 | 2 | 26 | 20 | 1 | 2 | −5 | 1 | 188 | 188 | 1 |
| 0 | 4 | 4 | 13 | 9 | 1 | 1 | −6 | 3 | 101 | 96 | 1 | 2 | −5 | 2 | 234 | 212 | 1 |
| 0 | 4 | 5 | 123 | 139 | 1 | 1 | −6 | 4 | 43 | 44 | 1 | 2 | −5 | 4 | 139 | 128 | 1 |
| 0 | 5 | 0 | 83 | 79 | 7 | 1 | −6 | 5 | 80 | 83 | 1 | 2 | −3 | 5 | 280 | 266 | 1 |
| 0 | 5 | 1 | 46 | 44 | 1 | 1 | −6 | 7 | 32 | 37 | 1 | 2 | −3 | 6 | 117 | 122 | 1 |
| 0 | 5 | 2 | 56 | 57 | 1 | 1 | −5 | 1 | 197 | 183 | 1 | 2 | −3 | 7 | 171 | 192 | 1 |
| 0 | 5 | 3 | 72 | 72 | 1 | 1 | −5 | 2 | 135 | 120 | 1 | 2 | −2 | 0 | 100 | 101 | 1 |
| 0 | 5 | 4 | 91 | 94 | 1 | 1 | −5 | 3 | 212 | 193 | 1 | 2 | −2 | 3 | 32 | 31 | 4 |
| 0 | 5 | 5 | 35 | 36 | 1 | 1 | −5 | 4 | 93 | 87 | 1 | 2 | −2 | 5 | 63 | 63 | 1 |
| 0 | 5 | 6 | 30 | 36 | 1 | 1 | −5 | 4 | 54 | 56 | 1 | 2 | −2 | 6 | 22 | 19 | 2 |
| 0 | 6 | 0 | 62 | 66 | 1 | 1 | 2 | 0 | 103 | 102 | 8 | 2 | −2 | 7 | 33 | 30 | 1 |
| 0 | 6 | 2 | 58 | 52 | 1 | 1 | 3 | 1 | 117 | 118 | 1 | 2 | −1 | 1 | 157 | 143 | 1 |
| 0 | 6 | 3 | 140 | 142 | 1 | 1 | 3 | 2 | 260 | 251 | 1 | 2 | −1 | 3 | 154 | 138 | 1 |
| 0 | 6 | 4 | 37 | 37 | 2 | 1 | 3 | 3 | 20 | 19 | 1 | 2 | −1 | 4 | 62 | 66 | 1 |
| 0 | 6 | 5 | 27 | 22 | 1 | 1 | −3 | 4 | 17 | 15 | 1 | 2 | −1 | 5 | 123 | 118 | 2 |
| 0 | 2 | 7 | 46 | 48 | 2 | 1 | −3 | 6 | 153 | 145 | 1 | 2 | −7 | 0 | 30 | 29 | 1 |
| 2 | −3 | 0 | 123 | 138 | 4 | 1 | −3 | 7 | 40 | 38 | 2 | 2 | −7 | 1 | 60 | 62 | 1 |
| 2 | −3 | 2 | 604 | 536 | 1 | 1 | −2 | 2 | 92 | 87 | 1 | 2 | −7 | 3 | 31 | 32 | 1 |
| 2 | −3 | 4 | 38 | 34 | 1 | 1 | −2 | 3 | 112 | 101 | 1 | 2 | −6 | 4 | 27 | 19 | 2 |
| 2 | −2 | 4 | 65 | 63 | 1 | 1 | −2 | 4 | 201 | 193 | 1 | 2 | −6 | 5 | 107 | 98 | 1 |
| 2 | −2 | 5 | 18 | 15 | 1 | 1 | −2 | 5 | 76 | 79 | 1 | 2 | −6 | 6 | 69 | 64 | 1 |
| 2 | −2 | 6 | 161 | 186 | 7 | 1 | −2 | 6 | 11 | 12 | 1 | 2 | 2 | 0 | 25 | 22 | 1 |
| 2 | −1 | 0 | 389 | 376 | 1 | 1 | −1 | 0 | 203 | 225 | 9 | 2 | 2 | 1 | 33 | 35 | 1 |
| 2 | −1 | 3 | 33 | 34 | 1 | 1 | −1 | 1 | 62 | 57 | 1 | 2 | 2 | 2 | 43 | 40 | 1 |
| 2 | −1 | 4 | 39 | 35 | 1 | 1 | −1 | 2 | 23 | 24 | 1 | 2 | 2 | 3 | 83 | 85 | 1 |
| 2 | −1 | 5 | 29 | 30 | 1 | 1 | −1 | 3 | 230 | 215 | 1 | 2 | 2 | 4 | 29 | 31 | 1 |
| 2 | −1 | 6 | 75 | 75 | 1 | 1 | −1 | 5 | 47 | 51 | 1 | 2 | 3 | 5 | 58 | 59 | 1 |
| 2 | 0 | 0 | 445 | 510 | 21 | 1 | 0 | 0 | 26 | 30 | 2 | 2 | 3 | 0 | 91 | 86 | 1 |
| 2 | 0 | 1 | 209 | 201 | 1 | 1 | 0 | 1 | 100 | 10 | 1 | 2 | 3 | 1 | 23 | 23 | 1 |
| 2 | 0 | 2 | 25 | 24 | 1 | 1 | 0 | 2 | 117 | 112 | 1 | 2 | 3 | 2 | 43 | 45 | 1 |
| 2 | 0 | 3 | 207 | 197 | 1 | 1 | 0 | 3 | 50 | 44 | 1 | 2 | 3 | 3 | 54 | 61 | 2 |
| 2 | 0 | 4 | 227 | 214 | 1 | 1 | 0 | 4 | 107 | 107 | 1 | 2 | 3 | 4 | 44 | 47 | 1 |
| 2 | 0 | 6 | 16 | 18 | 1 | 1 | 0 | 5 | 57 | 57 | 1 | 2 | 3 | 5 | 28 | 27 | 1 |
| 2 | 0 | 0 | 453 | 499 | 36 | 1 | 1 | 0 | 120 | 122 | 10 | 2 | 4 | 2 | 33 | 36 | 2 |
| 2 | 1 | 1 | 59 | 60 | 1 | 1 | 1 | 1 | 123 | 120 | 1 | 2 | 4 | 3 | 18 | 13 | 3 |
| 2 | 1 | 2 | 72 | 72 | 1 | 1 | 1 | 2 | 151 | 146 | 1 | 2 | 4 | 4 | 32 | 32 | 1 |
| 2 | 1 | 3 | 23 | 20 | 1 | 1 | 1 | 3 | 21 | 21 | 1 | 2 | 4 | 0 | 32 | 33 | 1 |
| 2 | 1 | 4 | 41 | 39 | 1 | 1 | 1 | 4 | 88 | 88 | 1 | 2 | 4 | 1 | 49 | 47 | 1 |
| 2 | 1 | 5 | 67 | 67 | 18 | 1 | 6 | 5 | 44 | 42 | 1 | 2 | 4 | 2 | 17 | 17 | 1 |
| 2 | 2 | 0 | 197 | 216 | 1 | 1 | 6 | 2 | 31 | 32 | 2 | 2 | 5 | 3 | 15 | 13 | 1 |
| 2 | 2 | 1 | 237 | 245 | 1 | 1 | 7 | 0 | 43 | 46 | 5 | 2 | 5 | 0 | 13 | 14 | 1 |
| 2 | 2 | 2 | 99 | 98 | 1 | 1 | 7 | 1 | 12 | 8 | 1 | 2 | 5 | 1 | 45 | 47 | 6 |
| 2 | 2 | 3 | 90 | 97 | 2 | 1 | 7 | 3 | 51 | 58 | 1 | 2 | 5 | 2 | 15 | 12 | 1 |

| H | K | L | Fobs | Fcalc | SigF |
|---|---|---|------|-------|------|
| 2 | −6 | 5 | 25 | 21 | 1 |
| 2 | −6 | 6 | 30 | 30 | 1 |
| 2 | −5 | 0 | 111 | 109 | 1 |
| 2 | −5 | 1 | 127 | 116 | 1 |
| 2 | −5 | 2 | 133 | 122 | 1 |
| 2 | −5 | 4 | 125 | 116 | 1 |
| 2 | −5 | 5 | 69 | 67 | 1 |
| 2 | −5 | 6 | 17 | 19 | 1 |
| 2 | −5 | 7 | 33 | 33 | 1 |
| 2 | −4 | 0 | 411 | 422 | 11 |
| 2 | −4 | 4 | 122 | 114 | 1 |
| 2 | −4 | 5 | 68 | 64 | 1 |
| 2 | −4 | 6 | 75 | 74 | 1 |
| 2 | −4 | 7 | 29 | 32 | 1 |
| 2 | −4 | 0 | 43 | 36 | 3 |
| 2 | −3 | 1 | 133 | 126 | 1 |
| 2 | −3 | 2 | 236 | 215 | 1 |
| 2 | −3 | 4 | 35 | 36 | 2 |
| 2 | −3 | 5 | 33 | 36 | 1 |
| 2 | −3 | 0 | 9 | 10 | 1 |
| 2 | −3 | 1 | 84 | 92 | 1 |
| 2 | −3 | 3 | 25 | 23 | 1 |
| 2 | −3 | 4 | 47 | 47 | 2 |
| 2 | −3 | 0 | 132 | 140 | 5 |
| 2 | −3 | 1 | 33 | 32 | 1 |
| 2 | −3 | 2 | 70 | 70 | 1 |
| 2 | −2 | 4 | 14 | 11 | 1 |
| 2 | −2 | 5 | 140 | 134 | 1 |
| 2 | −2 | 0 | 35 | 34 | 1 |
| 2 | −2 | 1 | 78 | 84 | 1 |
| 2 | −2 | 3 | 10 | 9 | 1 |
| 2 | −2 | 4 | 42 | 43 | 3 |
| 2 | −2 | 5 | 37 | 35 | 1 |
| 2 | −1 | 0 | 54 | 53 | 2 |
| 2 | −1 | 1 | 36 | 31 | 1 |
| 2 | −1 | 2 | 60 | 68 | 2 |
| 2 | −1 | 3 | 137 | 134 | 1 |
| 2 | −1 | 4 | 162 | 162 | 2 |
| 2 | −1 | 0 | 31 | 33 | 1 |
| 2 | −1 | 1 | 42 | 42 | 2 |
| 2 | −1 | 2 | 121 | 132 | 1 |
| 2 | −1 | 3 | 15 | 12 | 8 |
| 2 | −1 | 0 | 84 | 84 | 1 |
| 2 | −1 | 2 | 83 | 81 | 2 |
| 2 | −1 | 3 | 35 | 31 | 1 |
| 2 | −1 | 5 | 30 | 34 | 1 |
| 2 | 0 | 0 | 168 | 176 | 16 |

TABLE 13-continued

Structure Amplitudes for 4-(acetylamino)-3-hydroxy-5-nitrobenzoic acid
Values of 10*Fobs and 10*Fcalc

| H | K | L | Fobs | Fcalc | SigF | H | K | L | Fobs | Fcalc | SigF | H | K | L | Fobs | Fcalc | SigF |
|---|---|---|------|-------|------|---|---|---|------|-------|------|---|---|---|------|-------|------|
| 2 | 2 | 4 | 62 | 64 | 1 | 2 | 8 | 0 | 73 | 71 | 9 | 3 | 0 | 1 | 15 | 16 | 1 |
| 2 | 2 | 5 | 49 | 50 | 1 | 2 | 8 | 1 | 23 | 23 | 1 | 4 | 0 | 2 | 76 | 69 | 11 |
| 2 | 2 | 6 | 23 | 26 | 1 | 2 | 8 | 2 | 49 | 49 | 3 | 5 | 0 | 1 | 23 | 19 | 1 |
| 2 | 3 | 0 | 83 | 94 | 7 | 2 | 9 | 0 | 32 | 34 | 3 | 5 | −7 | 2 | 41 | 43 | 1 |
| 2 | 3 | 1 | 26 | 33 | 1 | 2 | 10 | 0 | 12 | 12 | 1 | 5 | −7 | 3 | 32 | 30 | 1 |
| 2 | 3 | 2 | 23 | 20 | 1 | 2 | −12 | 2 | 14 | 15 | 1 | 5 | −7 | 4 | 27 | 25 | 1 |
| 2 | 3 | 3 | 101 | 98 | 9 | 2 | −12 | 1 | 27 | 25 | 1 | 5 | −6 | 0 | 46 | 45 | 1 |
| 2 | 4 | 0 | 45 | 45 | 1 | 2 | −12 | 0 | 8 | 6 | 1 | 5 | −6 | 1 | 63 | 61 | 1 |
| 2 | 4 | 3 | 35 | 39 | 5 | 2 | −11 | 1 | 65 | 59 | 6 | 5 | −6 | 2 | 14 | 15 | 1 |
| 2 | 5 | 0 | 60 | 57 | 1 | 2 | −11 | 0 | 42 | 4 | 11 | 5 | −6 | 3 | 88 | 91 | 1 |
| 2 | 5 | 2 | 90 | 90 | 1 | 2 | −10 | 1 | 14 | 15 | 1 | 5 | −5 | 0 | 81 | 78 | 1 |
| 2 | 5 | 3 | 37 | 36 | 1 | 2 | −10 | 3 | 53 | 52 | 3 | 5 | −5 | 1 | 22 | 23 | 1 |
| 2 | 5 | 4 | 12 | 13 | 2 | 2 | −10 | 2 | 65 | 67 | 1 | 5 | −5 | 2 | 16 | 20 | 1 |
| 2 | 5 | 5 | 49 | 46 | 1 | 2 | −10 | 1 | 72 | 74 | 1 | 5 | −5 | 3 | 87 | 86 | 1 |
| 2 | 6 | 1 | 26 | 24 | 1 | 2 | −9 | 2 | 28 | 31 | 2 | 5 | −5 | 4 | 16 | 13 | 1 |
| 2 | 6 | 3 | 95 | 94 | 1 | 2 | −9 | 3 | 50 | 55 | 1 | 5 | −4 | 0 | 47 | 51 | 1 |
| 2 | 6 | 4 | 59 | 56 | 2 | 2 | −9 | 5 | 59 | 47 | 1 | 5 | −4 | 1 | 38 | 40 | 1 |
| 2 | 6 | 5 | 8 | 8 | 1 | 2 | −9 | 1 | 34 | 36 | 2 | 5 | −4 | 2 | 41 | 38 | 1 |
| 2 | 7 | 0 | 50 | 52 | 1 | 2 | −9 | 4 | 22 | 20 | 1 | 5 | −4 | 3 | 57 | 58 | 1 |
| 2 | 7 | 2 | 110 | 107 | 1 | 2 | −8 | 2 | 76 | 77 | 1 | 5 | −4 | 4 | 41 | 46 | 1 |
| 2 | 7 | 3 | 126 | 121 | 1 | 2 | −8 | 3 | 39 | 39 | 1 | 5 | −4 | 5 | 99 | 101 | 2 |
| 2 | 7 | 4 | 31 | 29 | 1 | 2 | −8 | 4 | 49 | 51 | 1 | 5 | −3 | 0 | 30 | 28 | 1 |
| 3 | −4 | 0 | 167 | 156 | 6 | 2 | −8 | 5 | 36 | 39 | 1 | 5 | −3 | 2 | 52 | 57 | 1 |
| 3 | −4 | 1 | 153 | 137 | 2 | 2 | −8 | 0 | 50 | 49 | 1 | 5 | −3 | 3 | 63 | 57 | 1 |
| 3 | −4 | 2 | 211 | 193 | 1 | 2 | −8 | 1 | 118 | 112 | 1 | 5 | −3 | 1 | 98 | 100 | 1 |
| 3 | −4 | 3 | 115 | 114 | 1 | 2 | −8 | 2 | 58 | 63 | 1 | 5 | −3 | 5 | 73 | 79 | 1 |
| 3 | −4 | 4 | 78 | 76 | 1 | 2 | −8 | 3 | 101 | 100 | 1 | 5 | −2 | 0 | 41 | 44 | 1 |
| 3 | −4 | 5 | 15 | 15 | 1 | 2 | −8 | 4 | 24 | 24 | 1 | 5 | −2 | 1 | 32 | 36 | 1 |
| 3 | −4 | 6 | 144 | 153 | 1 | 2 | −7 | 0 | 36 | 38 | 1 | 5 | −2 | 2 | 124 | 115 | 1 |
| 3 | −3 | 0 | 131 | 126 | 1 | 2 | −7 | 1 | 11 | 12 | 1 | 5 | −2 | 3 | 91 | 90 | 1 |
| 3 | −3 | 2 | 14 | 13 | 1 | 2 | −7 | 2 | 73 | 74 | 1 | 5 | −2 | 4 | 86 | 92 | 1 |
| 3 | −3 | 3 | 30 | 35 | 4 | 4 | −11 | 0 | 13 | 13 | 1 | 5 | −1 | 2 | 39 | 42 | 1 |
| 3 | −1 | 1 | 51 | 49 | 1 | 5 | −11 | 1 | 50 | 47 | 3 | 7 | 0 | 0 | 65 | 64 | 1 |
| 3 | −1 | 2 | 29 | 26 | 2 | 5 | −10 | 0 | 18 | 17 | 1 | 7 | 0 | 1 | 18 | 19 | 2 |
| 3 | −1 | 3 | 133 | 131 | 1 | 5 | −10 | 1 | 8 | 7 | 4 | 7 | 1 | 0 | 23 | 23 | 7 |
| 3 | −1 | 4 | 73 | 71 | 1 | 5 | −9 | 0 | 12 | 10 | 1 | 7 | 0 | 1 | 64 | 64 | 7 |
| 3 | 0 | 0 | 74 | 77 | 6 | 5 | −9 | 1 | 69 | 70 | 1 | 7 | −6 | 0 | 24 | 23 | 1 |
| 3 | 0 | 2 | 93 | 89 | 2 | 5 | −8 | 0 | 29 | 29 | 1 | 7 | −4 | 1 | 25 | 24 | 3 |
| 3 | 0 | 3 | 31 | 28 | 1 | 5 | −8 | 2 | 43 | 41 | 2 | 8 | 0 | 0 | 19 | 16 | 1 |
| 3 | 0 | 4 | 45 | 49 | 1 | 5 | −8 | 3 | 32 | 33 | 3 | 8 | −1 | 0 | 16 | 13 | 1 |
| 3 | 1 | 0 | 17 | 13 | 1 | 5 | −8 | 0 | 39 | 39 | 1 |   |   |   |    |    |   |
| 3 | 1 | 2 | 13 | 13 | 1 | 5 | −7 | 1 | 25 | 23 | 1 |   |   |   |    |    |   |
| 3 | 1 | 3 | 39 | 39 | 1 | 5 | −7 | 2 | 41 | 41 | 1 |   |   |   |    |    |   |
| 3 | 1 | 5 | 28 | 27 | 1 | 5 | −7 | 0 | 81 | 84 | 1 |   |   |   |    |    |   |
| 4 | 0 | 3 | 54 | 55 | 2 | 4 | −6 | 2 | 27 | 20 | 1 |   |   |   |    |    |   |
| 4 | 0 | 5 | 38 | 39 | 1 | 4 | −6 | 0 | 107 | 111 | 1 |   |   |   |    |    |   |
| 4 | −1 | 0 | 57 | 49 | 4 | 4 | −6 | 1 | 14 | 12 | 4 |   |   |   |    |    |   |

Fobs / Fcalc / SigF (additional columns):

| H | K | L | Fobs | Fcalc | SigF |
|---|---|---|------|-------|------|
| 4 | 0 | 1 | 132 | 127 | 1 |
| 4 | 0 | 2 | 36 | 35 | 1 |
| 4 | −7 | 1 | 65 | 68 | 1 |
| 4 | −7 | 2 | 69 | 62 | 1 |
| 4 | −7 | 3 | 42 | 48 | 1 |
| 4 | −6 | 4 | 30 | 30 | 1 |
| 4 | −6 | 0 | 101 | 110 | 1 |
| 4 | −6 | 1 | 165 | 174 | 3 |
| 4 | −6 | 2 | 17 | 20 | 1 |
| 4 | −6 | 3 | 61 | 64 | 1 |
| 4 | −5 | 4 | 83 | 86 | 1 |
| 4 | −5 | 0 | 114 | 155 | 5 |
| 4 | −5 | 1 | 213 | 217 | 1 |
| 4 | −5 | 2 | 21 | 25 | 1 |
| 4 | −5 | 3 | 29 | 30 | 2 |
| 4 | −5 | 4 | 47 | 48 | 1 |
| 4 | −4 | 0 | 37 | 39 | 1 |
| 4 | −4 | 1 | 73 | 76 | 1 |
| 4 | −4 | 2 | 119 | 122 | 6 |
| 4 | −4 | 3 | 29 | 27 | 1 |
| 4 | −4 | 0 | 95 | 94 | 2 |
| 4 | −3 | 1 | 112 | 119 | 1 |
| 4 | −3 | 2 | 121 | 115 | 1 |
| 4 | −3 | 3 | 143 | 143 | 1 |
| 4 | −3 | 4 | 57 | 55 | 2 |
| 4 | −2 | 0 | 63 | 64 | 3 |
| 4 | −2 | 1 | 97 | 106 | 4 |
| 4 | −2 | 2 | 81 | 81 | 1 |
| 4 | −2 | 3 | 47 | 46 | 1 |
| 4 | −2 | 4 | 80 | 75 | 1 |
| 4 | −2 | 0 | 110 | 110 | 1 |

TABLE 13-continued

Structure Amplitudes for 4-(acetylamino)-3-hydroxy-5-nitrobenzoic acid
Values of 10*Fobs and 10*Fcalc

| H | K | L | Fobs | Fcalc | SigF | H | K | L | Fobs | Fcalc | SigF | H | K | L | Fobs | Fcalc | SigF |
|---|---|---|------|-------|------|---|---|---|------|-------|------|---|---|---|------|-------|------|
| 4 | 1 | 1 | 156 | 154 | 1 | 4 | -6 | 2 | 19 | 18 | 1 | | | | | | |
| 4 | 1 | 2 | 46 | 44 | 1 | 4 | -6 | 3 | 52 | 50 | 1 | | | | | | |
| 4 | 1 | 3 | 19 | 18 | 1 | 4 | -5 | 0 | 201 | 212 | 13 | | | | | | |
| 4 | 1 | 4 | 12 | 10 | 1 | 4 | -5 | 1 | 105 | 104 | 1 | | | | | | |
| 4 | 2 | 0 | 76 | 81 | 7 | 4 | -5 | 3 | 19 | 20 | 1 | | | | | | |
| 4 | 2 | 1 | 112 | 104 | 1 | 4 | -4 | 0 | 73 | 82 | 8 | | | | | | |
| 4 | 2 | 2 | 24 | 24 | 1 | 4 | -4 | 1 | 131 | 129 | 1 | | | | | | |
| 4 | 2 | 3 | 17 | 19 | 1 | 4 | -4 | 2 | 48 | 44 | 1 | | | | | | |
| 4 | 2 | 4 | 17 | 18 | 1 | 4 | -3 | 0 | 64 | 69 | 5 | | | | | | |
| 4 | 3 | 0 | 100 | 96 | 10 | 4 | -3 | 1 | 237 | 232 | 1 | | | | | | |
| 4 | 3 | 1 | 14 | 11 | 1 | 4 | -3 | 2 | 95 | 91 | 1 | | | | | | |
| 4 | 3 | 2 | 18 | 22 | 2 | 4 | -3 | 3 | 32 | 29 | 1 | | | | | | |
| 4 | 4 | 1 | 24 | 22 | 1 | 4 | -2 | 1 | 38 | 40 | 2 | | | | | | |
| 4 | 4 | 2 | 61 | 59 | 2 | 4 | -2 | 2 | 155 | 152 | 1 | | | | | | |
| 4 | 5 | 0 | 55 | 56 | 5 | 4 | -2 | 3 | 82 | 82 | 1 | | | | | | |
| 4 | 5 | 2 | 30 | 31 | 1 | 4 | -1 | 1 | 66 | 59 | 1 | | | | | | |
| 4 | 5 | 3 | 13 | 14 | 1 | 4 | -1 | 2 | 99 | 93 | 1 | | | | | | |
| 4 | 6 | 0 | 15 | 13 | 2 | 4 | -1 | 3 | 79 | 80 | 1 | | | | | | |
| 4 | 6 | 1 | 26 | 25 | 1 | 4 | 0 | 1 | 20 | 17 | 1 | | | | | | |
| 4 | 6 | 2 | 35 | 36 | 1 | 4 | 0 | 2 | 36 | 35 | 1 | | | | | | |
| 4 | 7 | 1 | 20 | 19 | 1 | 4 | 0 | 3 | 119 | 119 | 1 | | | | | | |
| 4 | 8 | 0 | 26 | 23 | 2 | 4 | 0 | 1 | 51 | 53 | 1 | | | | | | |
| 5 | -12 | 0 | 38 | 36 | 2 | 5 | 1 | 2 | 23 | 21 | 1 | | | | | | |
| 5 | -11 | -1 | 19 | 16 | 1 | 5 | 2 | 1 | 47 | 41 | 1 | | | | | | |
| 5 | -11 | 2 | 14 | 18 | 1 | 5 | 2 | 2 | 22 | 21 | 1 | | | | | | |
| 5 | -10 | 0 | 22 | 22 | 3 | 5 | 4 | 0 | 13 | 9 | 2 | | | | | | |
| 5 | -10 | 1 | 43 | 37 | 1 | 5 | -10 | 0 | 36 | 37 | 2 | | | | | | |
| 5 | -10 | 2 | 25 | 26 | 2 | 5 | -9 | 0 | 13 | 14 | 1 | | | | | | |
| 5 | -10 | 3 | 15 | 15 | 1 | 5 | -9 | 1 | 10 | 10 | 1 | | | | | | |
| 5 | -9 | 0 | 26 | 25 | 3 | 5 | -8 | 0 | 25 | 25 | 1 | | | | | | |
| 5 | -9 | 1 | 26 | 23 | 1 | 5 | -8 | 1 | 30 | 30 | 1 | | | | | | |
| 5 | -9 | 2 | 60 | 60 | 2 | 5 | -7 | 0 | 28 | 29 | 2 | | | | | | |
| 5 | -9 | 3 | 19 | 20 | 1 | 5 | -7 | 2 | 19 | 19 | 1 | | | | | | |
| 5 | -9 | 4 | 35 | 33 | 1 | 5 | -7 | 1 | 23 | 24 | 1 | | | | | | |
| 5 | -8 | 0 | 57 | 57 | 1 | 5 | -6 | 2 | 38 | 39 | 1 | | | | | | |
| 5 | -8 | -1 | 16 | 15 | 1 | 5 | -6 | 0 | 44 | 46 | 5 | | | | | | |
| 5 | -8 | 2 | 22 | 18 | 6 | 5 | -5 | 1 | 32 | 28 | 1 | | | | | | |
| 5 | -8 | 3 | 33 | 31 | 3 | 5 | -5 | 2 | 29 | 30 | 1 | | | | | | |
| 5 | -8 | 4 | 205 | 213 | 8 | 5 | -5 | 0 | 25 | 23 | 5 | | | | | | |
| 5 | -7 | 0 | 29 | 30 | 1 | 5 | -4 | 1 | 41 | 42 | 1 | | | | | | |
| 5 | 2 | 2 | 11 | 14 | 6 | 5 | -4 | 0 | 21 | 23 | 5 | | | | | | |
| 5 | 3 | 0 | 76 | 77 | 3 | 5 | -3 | 1 | 22 | 24 | 1 | | | | | | |
| 5 | 3 | 3 | 19 | 21 | 8 | 5 | -2 | 0 | 50 | 50 | 2 | | | | | | |
| 5 | 4 | 1 | 49 | 49 | 1 | 5 | -2 | 1 | 32 | 33 | 1 | | | | | | |

TABLE 14

Summary of the results of DelPhi calculations using N2 neuraminidase and a benzoic acid-derived series of inhibitors All Gibbs free energy values ΔG are supplied in kcal/mol. [Protein molecule has partial charges assigned to all residues(amber charges for proteins). ($\epsilon_m$(protein) = 4.0, $\epsilon_m$(inhibitor) = 78.3, $\epsilon_s$ = 78.3, ionic strength = 0.01, probe radius = 1.8 Å, use of focusing potential, final run: grid size/fill = 65/67%, 3000 linear and 3000 nonlinear cycles of refinement; initial run: grid size/fill 65/50%, 1000 linear and 3000 nonlinear cycles of refinement, probe radius = 1.8 Å)].

| protein 1 | protein 2 | $\Delta G_{s,1}$ | $\Delta G_{s,2}$ | $\Delta G_s$ hydrat | $\Delta G_{inter}$ electr. | $K_{electr.}$ | $\Delta G$ total energy | $K_{total}$ |
|---|---|---|---|---|---|---|---|---|
| N2 A/Tokyo/3/67 | 108 | 9.58 | −7.87 | 1.7 | −7.58 | 3.3 $10^{-6}$ | −5.87 | 5.6 $10^{-5}$ |
| N2 A/Tokyo/3/67 | 106 | 5.78 | −3.45 | 2.33 | −7.06 | 7.8 $10^{-6}$ | −4.73 | 3.8 $10^{-4}$ |
| N2 A/Tokyo/3/67 | 105 | 8.40 | −4.73 | 3.67 | −6.64 | 1.6 $10^{-5}$ | −2.97 | 7.1 $10^{-3}$ |
| B/Lee/40 | DANA | 14.78 | −13.77 | 1.01 | −8.36 | 8.9 $10^{-7}$ | −7.35 | 4.8 $10^{-6}$ |
| N2 A/Tokyo/3/67 | 203 | 4.29 | −4.74 | −0.45 | −6.79 | 1.2 $10^{-5}$ | −7.24 | 5.8 $10^{-5}$ |
| N2 A/Tokyo/3/67 | 205 | 5.15 | −8.46 | −3.31 | −9.59 | 1.1 $10^{-7}$ | −12.90 | 4.6 $10^{-10}$ |
| N2 A/Tokyo/3/67 | 206 | 4.25 | −2.46 | 1.79 | −7.39 | 4.5 $10^{-6}$ | −5.60 | 8.8 $10^{-5}$ |
| N2 A/Tokyo/3/67 | 207 | 5.53 | −4.94 | 0.58 | −9.19 | 2.2 $10^{-7}$ | −8.60 | 5.9 $10^{-7}$ |
| N2 A/Tokyo/3/67 | 208 | 6.38 | −5.19 | 1.19 | −4.10 | 1.1 $10^{-3}$ | −2.90 | 7.9 $10^{-3}$ |
| N2 A/Tokyo/3/67 | 209 | 4.55 | −9.40 | −4.85 | −4.03 | 1.2 $10^{-3}$ | −8.86 | 3.9 $10^{-7}$ |
| N2 A/Tokyo/3/67 | 209 | 5.91 | −18.97 | −13.06 | −5.22 | 1.7 $10^{-4}$ | −18.28 | 5.9 $10^{-14}$ |
| N2 A/Tokyo/3/67 | 210 | 4.91 | −11.08 | −6.17 | −9.74 | 8.9 $10^{-8}$ | −15.91 | 3.1 $10^{-12}$ |
| N2 A/Tokyo/3/67 | 211 | 5.47 | −2.96 | 2.51 | −1.80 | 1.8 $10^{-1}$ | 0.71 | — |
| N2 A/Tokyo/3/67 | 212 | 5.32 | −3.85 | 1.48 | −2.30 | 2.2 $10^{-2}$ | −0.68 | 2.5 $10^{-1}$ |
| N2 A/Tokyo/3/67 | 213 | 5.38 | −7.06 | −1.68 | −6.07 | 4.1 $10^{-5}$ | −7.75 | 2.4 $10^{-6}$ |

REFERENCES

G. M. Air and W. G. Laver, "The Neuraminidase of Influenza Virus," *Proteins: Structure, Function, and Genetics*, 6, 341–356 (1989).

K. Appelt, R. J. Bacquet, C. A. Bartlett, C. L. J. Booth, S. T. Freer, M. A. M. Fuhry M. R. Gehring, S. M. Herrmann, E. F Howland, C. A. Janson, T. R. Jones, C.-C. Kan, V. Kathardekar, K. K. Lewis, G. P. Marzoni, D. A. Matthews, C. Mohr, E. W. Moomaw, C. A. Morse, S. J. Oatley, R. C. Ogden, M. R. Reddy, S. H. Reich, W. S. Schoettlin, W. W. Smith, M.D. Varney, J. E. Villafranca, R. W. Ward, S. Webber, S. E. Webber, K. M. Welsh, and J. White, "Design of Enzyme Inhibitors Using Iterative Protein Crystallographic Analysis," *J. Med. Chem.*, 34, 1925–1934 (1991).

J. Appleton, "Aromatic Amides. V. Intramolecular Hydrogen Bonding in Ortho-Substituted Amides," *Aust. J. Chem.*, 26, 1667–1677 (1970).

G. Ashwell and A. Morell, "The Role of Surface Carbohydrates in the Hepatic Recognition and Transport of Circulating Glycoproteins," *Adv. Enzymol.*, 41, 99– 128 (1974).

M. Aymard-Henry, M. T. Coleman, W. R. Dowdle, W. G. Laver, G. C. Shild, and R. G. Webster, "Influenza Virus Neuraminidase and Neuraminidase Inhibition Test Procedures," *Bull. WHO*, 48, 199–202 (1973).

D. Bashford and M. Karplus, "pKa's of Ionizable Groups in Proteins: Atomic Detail from a Continuum Electrostatic Model," *Biochemistry*, 29, 10219–10225 (1990).

P. Bossart-Whitaker, M. Carson, Y. S. Babu, C. D. Smith, W. G. Laver, and G. M. Air, "Three-Dimensional Structure of Influenza A N9 Neuraminidase and its Complex with the Inhibitor 2-Deoxy-2,3-dehydro-N-acetyl Neuraminic Acid," *J. Mol. Biol.*, 232, 1069–1089 (1993).

K. W. Brammer, C. R. McDonald, and M. S. Tute, "Antiviral Properties of 1 -Phenoxymethyl-3,4-dihydro- and 1,2,3,4- Tetrahydroisoquinolines," *Nature*, 219, 515–517 (1968).

R. Brossmer, G. Keilich, and D. Zeigler, "Inhibition Studies on Vibrio cholerae Neuraminidase," *Hoppe-Seyler's Z. Physiol. Chem.*, 358, 391–396 (1977).

H. C. Brown, J. A. Sikorski, S. U. Kulkarni, and H. D. Lee, "Thexylchloroborane-Methyl Sulfide. A Selective Monohydroborating Agent with Exceptional Regioselectivity," *J. Org. Chem.*, 45, 4540–4542 (1980).

A. T. Brunger, *X-PLOR Manual*, Version 3.0 (Yale University, New Haven, Conn., 1992).

G. Bruno and L. Randaccio, "A Refinement of the Benzoic Acid Structure at Room Temperature," *Acta Cryst.*, B36, 1711–1712 (1980).

R. F. Bryan, P. Hartley and S. Peckler, "3-(p-Bromobenzoyl)-1,3-thiazolidine-2-thione," *Acta Cryst.*, B36, 1709–1710 (1980).

W. P. Burmeister, R. W. H. Ruigrok, and S. Cusack, "The 2.2 Å Resolution Crystal Structure of Influenza B Neuraminidase and its Complex with Sialic Acid," *EMBO J.*, 11, 49–56 (1992).

P. A. Carpy and J. L. Goursolle, "Acide [Dichloro-2, 3(Thenoyl-2)-4 -Phenoxy] Acetique (Acide Tienilique)," *Acta Cryst.*, B36, 1706–1708 (1980).

M. R. Castrucci and Y. Kawaoka, "Biologic Importance of the Neuraminidase Stalk Length in Influenza A Virus," *J. Virology*, 67, 759–764 (1993).

A. K. J. Chong, M. S. Pegg, N. R. Taylor, and M. Von Itzstein, "Evidence for a Sialosyl Cation Transition-State Complex in the Reaction of Sialidase from Influenza Virus," *Eur. J. Biochem.*, 207, 335–343 (1992).

P. S. Daniels, S. Jeffries, P. Yates, G. C. Schild, G. N. Rogers, J. C. Paulson, S. A. Wharton, A. P. Douglas, J. J. Skehel, and D.C. Wiley, "The Receptor-Binding and Membrane-Fusion Properties of Influenza Virus Variants Selected Using Anti-Hemagglutinin Monoclonal Antibodies," *EMBO J.*, 6, 1459–1465 (1987).

D. Davis, J. D. Madura, B. A. Luty and McCammon, "Electrostatics and Diffusion of Molecules in Solution," *J. A. Comput. Phys. Commun.*, 62, 187–197 (1991).

DelPhi 2.0, BIOSYM Technologies, Inc., San Diego, Calif. 92121, U.S.A.

M. J. S. Dewar, "Development of Status of MNDO/3 and MNDO," *J. Mol. Struct.*, 100, 41–46 (1983).

M. J. S. Dewar, E. G. Zoebisch, E. F. Healy and J. J. P. Stewart, "AM1: A New General Purpose Quantum Mechanical Molecular Model," *J. Am. Chem. Soc.*, 107, 3902–3909 (1985).

R. Drzeniek, "Viral and Bacterial Neuraminidases," *Curr.*

*Topics Microbiol. Immunol.*, 59, 35–74 (1972).

K. M. Edwards, J. C. King, M. C. Steinhoff, J. Thompson, M. L. Clements, P. F. Wright, and B. R. Murphy, "Safety and Immunogenicity of Live Attenuated Cold-Adapted Influenza B/Ann Arbor/1/86 Reassortant Virus Vaccine in Infants and Children," *J. Infect. Dis.*, 163, 740–745 (1991).

G. P. Ellis and R. T. Jones, "One-Step Synthesis and Spectral Study of Some 1-Methyl-benzimidazoles, Including Use of a Lanthanide Shift Reagent," *J. Chem. Soc. Perk. Trans. I*, 8, 903–909 (1974).

J. Erickson, D. J. Neidhart, J. VanDrie, D. J. Kempf, X. C. Wang, D. W. Norbeck, J. J. Plattner, J. W. Rittenhouse, M. Turon, N. Wideburg, W. E. Kohlbrenner, R. Simmer, R. Helfrich, D. A. Paul, and M. Knigge, "Design, Activity, and 2.8 Å Crystal Structure of a $C_2$ Symmetric Inhibitor Complexed to HIV-1 Protease," Science, 249, 527–533 (1990).

J. W. Erickson and S. W. Fesik, "Macromolecular X-Ray Crystallography and NMR as Tools for Structure-Based Drug Design "in J. A. Bristol, ed. *Ann. Rep. Med. Chem.*, 27, 271–289 (1992).

M. Flasher, J. Kessler, and S. W. Tannenbaum, "The Interaction of Substrate-Related Ketals with Bacterial and Viral Neuraminidase," *Arch. Biochem. Biophys.*, 221,188 (1983).

P. G. Gassman and H. R. Drewes, "The Ortho Functionalization of Aromatic Amines. Benzylation, Formylation, and Vinylation of Anilines," *J. Am. Chem. Soc.*, 100, 7600–7610 (1978).

M. K. Gilson, K. A. Sharp and B. H. Honig, "Calculating the Electrostatic Potential of Molecules in Solution," *J. Comput. Chem.*, 9, 327 (1988).

M. K. Gilson and B. Honig, "Energetics of Charge-Charge Interactions in Proteins," *Proteins*, 4, 7–18 (1988).

M. K. Gilson, "Multiple-Site Titration and Molecular Modeling: Two Rapid Methods for Computing Energies and Forces for Ionizable Groups in Proteins," *Proteins*, 15,266–282 (1993)

B. I. Glanzer, Z. Gyorgydeak, B. Bernet, and A. Vasella, "34. Analogues of Sialic Acids as Potential Sialidase Inhibitors. Synthesis of $C_6$ and $C_7$ Analogues of N-Acetyl-6-amino-2, 6-dideoxyneuraminic Acid," *Helv. Chim. Acta*, 74, 343–368 (1991).

P. H. Gozlan and C. Riche, "Analogues de la Noradrenaline. Structure Cristalline de la (Methylene Dioxy-3',4')-phenyl-2-Hydroxy-2 Acetamideoxime," *Acta Cryst.*, B32, 1662–1665 (1976).

T. H. Haskell, F. E. Peterson, D. Watson, N. R. Plessas, and T. Culbertson, "Neuraminidase Inhibition and Chemotherapy," *J. Med. Chem.*, 13, 697–704 (1970).

Y. Hatanaka, Y. Ebina, and T. Hiyama, "γ-Selective Cross-Coupling Reaction of Allyltrifluorosilanes: A New Approach to Regiochemical Control in Allylic Systems," *J. Am. Chem. Soc.*, 113, 7075–7076 (1991).

A. Hay, R. B. Belshe, E. L. Anderson, G. J. Gorse, and T. Ulf Westblom, in R. B. Belshe, *Textbook of Human Virology*, 2nd ed., Mosby-Year Book, St. Louis, pp. 307–341 (1991).

F. G. Hayden and A. J. Hay, "Emergence and Transmission of Influenza A Viruses Resistant to Amantadine and Rimantadine," *Curr. Top. Microbiol. Immunol.*, 176, 119–130 (1992).

A. J. Howard, C. Nielsen, N. H. Xuong, "Software for a Diffractometer with Multiwire are Detector," *Methods Enzymol.* 114, 452 (1985).

N. Iwasaw, T. Kato, and K. Narasaka, "A Convenient Method for Dihydroxylation of Olefins by the Combined Use of Osmium Tetroxide and Dihydroxyphenylborane," *Chem. Lett.*, 1721–1724 (1988).

M. N. Janakiraman, C. L. White, W. G. Laver, G. M. Air, and M. Luo, "Structural Evidence for Hydrolysis Catalyzed by Influenza Virus Neuraminidase Driven by Stabilization of the Oxocarbonium Ion Intermediate," submitted for publication (1993).

M. J. Jedrzejas and M. Luo, *Science*, submitted for publication (computation).

T. A. Jones, "Agraphics Model Building Refinement System for Macromolecules," *J. Appl. Crystallogr.*, 11, 268–272 (1978).

T. A. Jones, "Diffraction Methods for Biological Macromolecules. Interactive Computer Graphics: FRODO," *Methods Enzymol.* 115, 157–171 0985).

A. H. Juffer, E. F. F. Botta, B. A. M. van Keulen, A. Van der Ploeg and H. J. C. Berendsen, "The Electrostatic Potential of Macromolecules in a Solvent: A Fundamental Approach," *J. Comput. Phys.*, 97, 144–170 (1991).

Y. Kageyama, T. Iwamoto, M. Haisa and S. Kashino, "Structure of the Phosphate Form of p-Nitrocinnamic acid," *Acta Cryst.*, C49, 833–834 (1993).

I. L. Karle (1952a). "The Structure of the Tetrachloroethylene Molecule," *J. Chem. Phys.* 20, 63–65.

I. L. Karle (1952b). "An Electron Doffraction Investigation of Cyclooctatetraene and Benzene," *J. Chem. Phys.* 20, 65–67.

F. Kasuya, K. Igarashi, and M. Fukui, "Metabolism of Benoxinate in Humans," *J. Pharm. Sci.*, 76, 303–305 (1987).

I. Klapper, R. Hagstrom, R. Fine, K. Sharp, and B. Honig, "Focusing of Electric Fields in the Active Site of Cu-Zn Superoxide Dismutase: Effects of Ionic Strength and Amino-Acid Modification," *Proteins: Structure, Function, and Genetics*, 1, 47– 59 (1986).

T. Kudo, Y. Nishimura, S. Kondo, and T. Takeuchi, "Syntheses of the Potent Inhibitors of Neuraminidase. N-(1,2-Dihydroxypropyl) Derivatives of Siastatin B and its 4-Deoxy Analogs," *J. Antibiot.*, 46, 300–309 (1993).

V. Kumar, S. Tanenbaum, and M. Brashner, "Methyl 5-Acetamido-2,6-anhydro- 3,5-dideoxy-D-manno-non-2-en-4-ulosonate," *Carbohyd. Res.*, 103, 281–285 (1982).

W. G. Laver and G. M. Air, "Use of X-Ray Crystallography in the Design of Antiviral Agents," Academic Press, San Diego (1990).

M. R. Lentz, R. G. Webster, and G. M. Air, "Site-Directed Mutation of the Active Site of Influenza Neuraminidase and Implications for the Catalytic Mechanism," *Biochemistry*, 26, 5351–5358 (1987).

D. R. Lide, "CRC Handbook of Chemistry and Physics," CRC Press (1993).

C. Liu and G. M. Air, "Selection and Characterization of a Neuraminidase-Minus Mutant of Influenza Virus and its Rescue by Cloned Neuraminidase Genes," *Virology*, 193, 1–5 (1993).

H. Mack and R. Brossmer, "Synthesis of 6-Epi- and 4,6-Bisepi-N-acetyl-D-neuraminic Acid by Aldol Condensation," *Tet. Lett.*, 33, 1867–1870 (1992).

A. McPherson, "Preparation and Analysis of Protein Crystals," *Methods in Enzymol.*, 114, 112–120 (1985).

P. Meindl, G. Bodo, P. Palese, J. Schulman, and H. Tuppy, "Inhibition of Neuraminidase Activity by Derivatives of 2-Deoxy-2,3-dehydro-N-acetylneuraminic Acid," *Virology*, 58, 457–463 (1974).

R. M. Metzger, R. K. Laidlaw, E. Torres and C. A. Panetta, "Crystal Structure of DMAP-C-HMTCAQ, $C_{30}H_{20}N_6O_2$, N,N-dimethylaminophenylcarbamate-2' -hydroxymethyl-11,11,12,12-tetracyano-anthraquinodimethan," *J. Cryst, Spect. Research*, 19(3), 475:482 (1989).

R. M. Metzger, J. L. Atwood, W. Lee, S. M. Rao, R. B. Lal and B. H. Loo, "Structure of MAP:MNA, the 1:1 Adduct Between (R)-Methyl2-(2,4-Dinitroanilino)propanoate (MAP) and 2-Methyl-4-nitroaniline (MNA), a New Nonlinear Optical Crystal," *Acta Cryst.*, C49, 738–741 (1993).

C. A. Miller, P. Wang, and M. Flashner, "Mechanism of Arthrobacter Sialophilus Neuraminidase: The Binding of Substrates and Transition-State Analogs," *Biochem. Biophys. Res. Comm.*, 83, 1479–1487 (1978).

J. A. Montgomery, S. Niwas, J. D. Rose, J. A. Secrist III, Y. S. Babu, C. A. Bugg, M.D. Erion, W. C. Guida, and S. E. Ealick, "Structure-Based Design of Inhibitors of Purine Nucleoside Phosphorylase. 1. 9-(Arylmethyl) Derivatives of 9-Deazaguanine," *J. Med. Chem.*, 36, 55–69 (1993).

C. E. Mountford, G. Grossman, K. T. Holmes, W. J. O'Sullivan, A. W. Hampson, R. L. Raison, and R. Webster, "Effect of Monoclonal Antineuraminidase Antibodies on the Kinetic Behavior of Influenza Virus Neuraminidase," *Mol. Immunol.*, 19, 811–816 (1982).

B. R. Murphy and R. G. Webster, "Orthomyxoviruses," in B. N. Fields and D. M. Knipe, eds., *Virology*, second edition, Raven Press, New York, pp. 1081–1152 (1990).

T. Nagal, Y. Miyaichi, T. Tomimori, Y. Suzuki, and H. Yamada, "In Vivo Anti-Influenza Virus Activity of Plant Flavonoids Possessing Inhibitory Activity for Influenza Virus Sialidase," *Antiviral Res.*, 19, 207–217 (1992).

G. O'Neill, "Have Aussies Found a Cure for the Flu?" *J. NIH Res.*, 5, 40–42 (1993).

B. B. Nielsen and I. K. Larsen, "3,4,5-Trihydroxybenzohydroxamic Acid Monohydrate, A Ribonucleotide Reductase Inhibitor," *Acta Cryst.*, C49, 810–813 (1993).

K. Nilsson and A. Hallberg, "Synthesis of 1-Propyl-3-(3-Hydroxyphenyl)piperidine by Regiocontrolled Palladium-Catalyzed Acylation," *J. Org. Chem.*, 57, 4015–4017 (1992).

P. Palese, K. Tobita, M. Ueda, and R. W. Compans, "Characterization of Temperature-Sensitive Influenza Virus Mutants Defective in Neuraminidase," *Virology*, 61,397–410 (1974).

P. Palese and R. W. Compans, "Inhibition of Influenza Virus Replication in Tissue Culture by 2-Deoxy-2,3-dehydro-N-trifluoroacetylneuraminic acid (FANA): Mechanism of Action," *J. Gen. Virology*, 33, 159–163 (1976).

J. C. Paulson in P.M. Conn, ed., *The Receptors*, Academic Press, Orlando, Vol 2, pp. 131–219 (1985).

G. Posner, "Substitution Reactions Using Organocopper Reagents," *Org. React.*, 22, 253–400 (1975).

D. C. Powers, L. F. Fries, B. R. Murphy, B. Thumar, and M. L. Clements, "In Elderly Persons Live Attenuated Influenza A Virus Vaccines Do Not Offer an Advantage Over Inactivated Virus Vaccine in Inducing Serum or Secretory Antibodies or Local Immunologic Memory," *J. Clin. Microbiol.*, 29, 498–505 (1991).

A. Rieche, H. Gross, and E. Hoft, "Synthesis of Aromatic Aldehydes with Dichloromethyl-Alkyl Ethers," *Chem. Ber.*, 93, 88–94 (1960).

Ripoll et al., "An Electrostatic Mechanism for Substrate Guidance Down the Aromatic Gorge of Acetylcholinesterase," *Proc. Natl. Acad. Sci.*, 90, 5128–5132 (1993).

M. G. Rossmann and D. M. Blow, "The Detection of Sub-units Within the Crystallographic Asymmetric Unit," *Acta Cryst.* 15, 24 (1962).

E. Schreiner, E. Zbiral, R. G. Kleineidam, and R. Schauer, "Synthesis of Some 2,3-Didehydro-2-deoxysialic Acids Structurally Varied at C-4 and their Behavior Towards Sialidase from Vibrio cholerae," *Liebigs Ann. Chem.*, 129–134 (1991).

V. Snieckus, "Directed Ortho Metalation. Tertiary Amide and O-Carbamate Directors in Synthetic Strategies for Polysubstituted Aromatics," *Chem. Rev.*, 90, 879–933 (1990).

S. Soundarajan, E. N. Duesler and J. H. Hageman, "Structure of 4-Carboxy-2-nitrobenzeneboronic Acid," *Acta Cryst.*, C49 690–693 (1993).

Y. Suzuki, Y. Nagao, H. Kato, M. Matsumoto, K. Nerome, K. Nakajima, and E. Nobusawa, "Human Influenza A Virus Hemagglutinin Distinguishes Sialyloligosaccharides in Membrane-Associated Gangliosides as its Receptor which Mediates the Adsorption and Fusion Processes of Virus Infection. Specificity for Oligosaccharides and Sialic Acids and the Sequence to which Sialic Acid is Attached," *J. Biol. Chem.*, 261, 17057–17061 (1986).

C. Tanford and Kirkwood, "Theory of Titration Curves I. General Equations for Impenetrable Phases," *J. Am. Chem. Soc.*, 79, 5333–5336 (1957).

N. R. Taylor and M. von Itzstein, "Molecular Modeling Studies on Ligand Binding to Sialidase from Influenza Virus and the Mechanism of Catalysis," *J. Med. Chem.*, 37, 616–624 (1994).

W. R. Tulip, J. N. Varghese, A. T. Baker, A. VanDonkelaar, W. G. Laver, R. G. Wobster, and P.M. Colman, "Refined Atomic Structures of N9 Subtype Influenza Virus Neuraminidase and Escape Mutants," *J. Mol. Biol.*, 221, 487–497 (1991).

W. R. Tulip, J. N. Varghese, W. G. Laver, R. G. Webster, and P. M. Colman, "Refined Crystal Structure of the Influenza Virus N9 Neuraminidase-NC41 Fab Complex," *J. Mol. Biol.*, 227, 122–148 (1992).

S. Usuki, P. Hoops, and C. C. Sweeley, "Growth Control of Human Foreskin Fibroblasts and Inhibition of Extracellular Sialidase Activity by 2-Deoxy-2,3-dehydro-N-acetylneuraminic Acid," *J. Biol. Chem.*, 263, 10595–10599 (1988a).

S. Usuki, S. Lyu, and C. C. Sweeley, "Sialidase Activities of Cultured Human Fibroblasts and the Metabolism of $G_{M3}$ Ganglioside," *J. Biol. Chem.*, 263, 6847–6853 (1988b).

J. N. Varghese, J. L. McKimm-Breschkin, J. B. Caldwell, A. A. Kortt, and P. M. Colman, "The Structure of the Complex Between Influenza Virus Neuraminidase and Sialic Acid, the Viral Receptor," *Proteins: Structure, Function, and Genetics*, 14, 327–332 (1992).

J. N. Varghese, P. M. Colman, "Three-dimensional Structure of the Neuraminidase of Influenza Virus A/Tokyo/3/67 at 2.2 Å Resolution," *J. Mol. Biol.* 221, 473–486 (1991).

M. D. Varney, G. P. Marzoni, C. L. Palmer, J. G. Deal, S. Wevver, K. M. Welsh, R. J. Bacquet, C. A. Bartlett, C. A. Morse, C. L. J. Booth, S. M. Herrmann, E. F. Howland, R. W. Ward, and J. White, "Crystal-Structure-Based Design and Synthesis of Benz[cd]indole-Containing Inhibitors of Thymidilate Synthase," *J. Meal. Chem.*, 35, 663–676 (1992).

A. Vasella and R. Wyler, "Synthesis of a Phosphonic Acid Analogue of N-Acetyl- 2,3-didehydro-2-deoxyneuraminic Acid, an Inhibitor of Vibrio cholerae Sialidase," *Helv. Chim. Acta*, 74, 451–463 (1991).

R. Verna and I. Kahn, "Syntheses of Indophenazines and 6-Piperidino/morpholinomethyl-indophenazines As Possible Excystment and Cysticidal Agents," *J. Ind. Chem. Soc.*, 55, 1043–1045 (1978).

L. M. Von Itzstein, W.-Y. Wu, T. V. Phan, B. Danylec, and B. Jin, "Derivatives and Analogues of 2-Deoxy-2,3-didehydro-N-acetylneuraminic Acid and their Use as Antiviral Agents," *Internat. Patent WO* 91/16320 (Oct. 31, 1991).

R. C. Wade, K. J. Clark, and P. J. Goodford, "Further Development of Hydrogen Bond Functions for Use in Determining Energetically Favorable Binding Sites on Molecules of Known Structure. 1. Ligand Probe Groups with the Ability to Form Two Hydrogen Bonds," *J. Med. Chem.*, 36, 140–147 (1993).

R. C. Wade and P. J. Goodford, "Further Development of Hydrogen Bond Functions for Use in Determining Energetically Favorable Binding Sites on Molecules of Known Structure. 2. Ligand Probe Groups with the Ability to Form More Than Two Hydrogen Bonds," *J. Med. Chem.*, 36, 148–156 (1993).

P. Wang, S. W. Tanenbaum, and M. Flashner, "Purification and Properties of Arthrobacter Neuraminidase," *Biochim. Biophys. Acta,* 523, 170–180 (1978).

S. E. Webber, T. M. Bleckman, J. Attard, J. G. Deal, V. Kathardekar, K. M. Welsh, S. Wevver, C. A. Janson, D. A. Matthews, W. W. Smith, S. T. Freer, S. R. Jordan, R. J. Bacquet, E. F. Howland, C. L. J. Booth, R. W. Ward, S. M. Hermann, J. White, C; A. Morse, J. A. Hilliard, and C. A. Bartlett, "Design of Thymidylate Synthase Inhibitors Using Protein Crystal Structures: The Synthesis and Biological Evaluation of a Novel Class of 5-Substituted Quinazolinones," *J. Med. Chem.*, 36, 733–746 (1993).

R. G. Webster, P. A. Reay, and W. G. Laver, "Protection Against Lethal Influenza With Neuraminidase," *Virology,* 164, 230–237 (1988).

P. F. Wright in A. P. Kendal, ed., "Options for the Control of Influenza II", Meeting in Courcheval, France (1992).

Y. Yamamoto, H. Kumazawa, K Inami, T. Teshimi, and T. Shiba, "Syntheses of Sialic Acid Isomers with Inhibitory Activity Against Neuraminidase," *Tet. Lett.*, 33, 5791–5794 (1992).

A. S. Yang, M. R. Grunner, R. Sampogna, K. Sharp and B. Honig, "On the Calculation of pKas in Proteins," *Proteins,* 15, 252–265 (1993).

What is claimed is:

1. An influenza virus neuraminidase inhibitor, its-analogs, its pharmaceutically acceptable salts, derivatives, and mixtures thereof having the following formula:

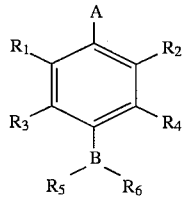

wherein $A=CO_2H$, $CO_2CH_3$, $NO_2$, $SO_3H$ or $PO_3H_2$;

wherein B=CH, N, O or S;

wherein $R_1$ and $R_2$=H, $NO_2$ or $(CH_m)_nX_1$ where m=1 or 2, n is an integer from 0 to 4 and $X_1$=guanidino, OH, $NH_2$, SH, $NO_2$, F, Cl, Br, I, CN, $CF_3$, $CO_2H$, $SO_3H$ or $PO_3H_2$;

wherein $R_3$ and $R_4$=H, $(CH_o)_pX_2$, $(CH_o)_pCHX_2CH_2$, $NH(CH_o)_pCHX_2CH_2X_2$, $NHCO(CH_o)_pCH_2X_2$ or $NHCO(CH_o)_pCHX_2CH_2X_2$ where o= 1 or 2, p is an integer from 0 to 4 and $X_2$=H, guanidino, OH, $NH_2$, SH, $NO_2$, $CF_3$, $CO_2H$, $SO_3H$ or $PO_3H_2$;

wherein $R_5$=H, OH, $NH_2$, $(CH_k)_1X_3$, $CO(CH_k)_1X_3$, $SO(CH_k)_1X_3$ or $SO_2(CH_k)_1X_3$ where k=1 or 2, 1 is an integer from 0 to 4 and $X_3$=guanidino, OH, $NH_2$, SH, $NO_2$, $CF_3$, $CO_2H$, $SO_3H$ or $PO_3H_2$;

wherein $R_6$=H, $CH(OH)X_4$, $CH(NH_2)X_4$, $COX_4$, $SOX_4$, or $SO_2X_4$, where $X_4$=H, $CH_3$, $CH_3CH_2$, $CH_3CHCH_3$, $CH_3CH_2CH_2$ or halogen substituted analogs of $X_4$; and wherein, when A is $CO_2H$ and B is N, $R_3$ is not H when $R_4$ is H or OH and wherein $R_3$ is not $NO_2$ or $NH_2$ when $R_4$ is H.

2. An influenza virus neuraminidase inhibitor, its analogs, its pharmaceutically acceptable salts, derivatives, and mixtures thereof having the following formula:

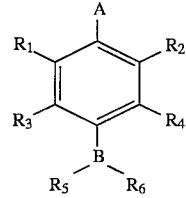

wherein $A=CO_2H$ or $CO_2CH_3$;

wherein B=CH or N;

wherein $R_1$ and $R_2$=H or $NO_2$;

wherein $R_3$=H, OH, $NH_2$, guanidino, $NO_2$, F, Cl or Br;

wherein $R_4=QR_7$ where Q=O, NH or $CH_2$ and $R_7$=H, $(CH_2)_oX_1$, $(CH_2)_oCHX_1CH_2X_1$, $CO(CH_2)_oCH_2X_1$ or $CO(CH_2)_oCHX_1CH_2X_1$ where o is an integer from 0 to 4 and $X_1$=H, guanidino, OH or $NH_2$;

wherein $R_5=COCH_3$;

wherein $R_6=(CH_2)_pX_2$ where p is an integer from 0 to 4 and $X_2$=OH, $NH_2$ or guanidino; and wherein, when A is $CO_2H$ and B is N, $R_3$ is not H when $R_4$ is H or OH and wherein $R_3$ is not $NO_2$ or NH 2 when $R_4$ is H.

3. An influenza virus neuraminidase inhibitor, its analogs, its pharmaceutically acceptable salts, derivatives, and mixtures thereof having the following formula:

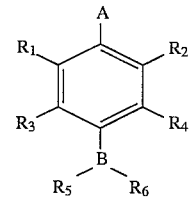

wherein $A=CO_2H$ or $CO_2CH_3$;

wherein B=N;

wherein $R_1$=H or $NO_2$;

wherein $R_2$=H or $NO_2$;

wherein $R_3$=H, OH, $NO_2$, $NH_2$ or guanidino;

wherein $R_4$=H, OH, OAc, $NH_2$, guanidino, $NHCOCH_2OH$, $NHCOCH(OH)CH_2OH$, $NHCOCH_2NH_2$, $NHCOCH_2CH_2CH_2NH_2$, CHO, $CH_2OH$, $CH_2OAc$, $CH_2CH_2OH$, $CH_2CH_2CH_2OH$, $CH_2CH(OH)CH_2OH$, $CH_2CH_{2l}$ $_{CH2l}$ $_{CH2l}$ $_{OH}$, $_{CH2}CH_2CH(OH)CH_2OH$, $CH_2I$, $CH=CH_2$, $CH_2CH=CH_2$ or $CH_2CH_2CH=CH_2$;

wherein $R_5$=H;

wherein $R_6=COCH_3$; and wherein $R_4$ is not H when $R_3$ is H or OH and wherein $R_4$ is not $NO_2$ or $NH_2$ when $R_3$ is H.

4. A composition for inhibiting influenza virus neuraminidase, comprising an effective amount of a pharmaceutically acceptable carder and a compound, its analogs, its pharmaceutically acceptable salts, derivatives, or mixtures thereof, having the following formula:

[Structure 1: benzene ring with A (top), R1 (upper left), R2 (upper right), R3 (lower left), R4 (lower right), B (bottom) bonded to R5 and R6]

wherein A=$CO_2H$, $CO_2CH_3$, $NO_2$, $SO_3H$ or $PO_3H_2$;

wherein B=CH, N, O or S;

wherein $R_1$ and $R_2$=H, $NO_2$ or $(CH_m)_nX_1$ where m=1 or 2, n is an integer from 0 to 4 and $X_1$=guanidino, OH, $NH_2$, SH, $NO_2$, F, Cl, Br, I, CN, $CF_3$, $CO_2H$, $SO_3H$ or $PO_3H_2$;

wherein $R_3$ and $R_4$=H, $(CH_o)_pX_2$, $(CH_o)_pCHX_2CH_2X_2$, $NH(CH_o)_pCHX_2CH_2X_2$, $NHCO(CH_o)_pCH_2X_2$ or $NHCO(CH_o)_pCHX_2CH_2X_2$ where o= 1 or 2, p is an integer from 0 to 4 and $X_2$=H, guanidino, OH, $NH_2$, SH, $NO_2$, $CF_3$, $CO_2H$, $SO_3H$ or $PO_3H_2$;

wherein $R_5$=H, OH, $NH_2$, $(CH_k)_1X_3$, $CO(CH_k)_1X_3$, $SO(CH_k)_1X_3$ or $SO(CH_k)_1X_3$ where k=1 or 2, l is an integer from 0 to 4 and $X_3$=guanidino, OH, $NH_2$, SH, $NO_2$, $CF_3$, $CO_2H$, $SO_3H$ or $PO_3H_2$;

wherein $R_6$=H, $CH(OH)X_4$, $CH(NH_2)X_4$, $COX_4$, $SOX_4$, or $SO_2X_4$, where $X_4$=H, $CH_3$, $CH_3CH_2$, $CH_3CHCH_3$, $CH_3CH_2CH_2$ or halogen substituted analogs of $X_4$; and wherein, when A is $CO_2H$ and B is N, $R_3$ is not H when $R_4$ is H or OH and wherein $R_3$ is not $NO_2$ or $NH_2$ when $R_4$ is H.

5. A composition for inhibiting influenza virus neuraminidase, comprising an effective amount of a pharmaceutically acceptable carrier and a compound, its analogs, its pharmaceutically acceptable salts, derivatives, or mixtures thereof, having the following formula:

[Structure: same benzene ring]

wherein A=$CO_2H$ or $CO_2CH_3$;

wherein B=CH or N;

wherein $R_1$ and $R_2$=H or $NO_2$;

wherein $R_3$=H, OH, $NH_2$, guanidino, $NO_2$, F, Cl or Br;

wherein $R_4$=$QR_7$ where Q=O, NH or $CH_2$ and $R_7$=H, $(CH_2)_oX_1$, $(CH_2)_oCHX_1CH_2X_1$, $CO(CH_2)_oCH_2X_1$ or $CO(CH_2)_oCHX_1CH_2X_1$ where o is an integer from 0 to 4 and $X_1$=H, guanidino, OH or $NH_2$;

wherein $R_5$=$COCH_3$;

wherein $R_6$=$(CH_2)_pX_2$ where p is an integer from 0 to 4 and $X_2$=OH, $NH_2$ or guanidino; and wherein, when A is $CO_2H$ and B is N, $R_3$ is not H when $R_4$ is H or OH and wherein $R_3$ is not $NO_2$ or $NH_2$ when $R_4$ is H.

6. A composition for inhibiting influenza virus neuraminidase, comprising an effective mount of a pharmaceutically acceptable carrier and a compound, its analogs, its pharmaceutically acceptable salts, derivatives, or mixtures thereof, having the following formula:

[Structure: same benzene ring]

wherein A=$CO_2H$ or $CO_2CH_3$;

wherein B=N;

wherein $R_1$=H or $NO_2$;

wherein $R_2$=H or $NO_2$;

wherein $R_3$=H, OH, $NO_2$, $NH_2$ or guanidino;

wherein $R_4$=H, OH, OAc, $NH_2$, guanidino, $NHCOCH_2OH$, $NHCOCH(OH)CH_2OH$, $NHCOCH_2NH_2$, $NHCOCH_2CH_2NH_2$, CHO, $CH_2OH$, $CH_2OAc$, $CH_2CH_2OH$, $CH_2CH_2CH_2OH$, $CH_2CH(OH)CH_2OH$, $CH_2CH_2CH_2CH_2OH$, $CH_2CH_2CH(OH)CH_2OH$, $CH_2I$, $CH=CH_2$, $CH_2CH=CH_2$ or $CH_2CH_2CH=CH_2$;

wherein $R_5$=H;

wherein $R_6$=$COCH_3$; and wherein $R_4$ is not H when $R_3$ is H or OH and wherein $R_4$ is not $NO_2$ or $NH_2$ when $R_3$ is H.

7. A method of inhibiting influenza virus neuraminidase comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

[Structure: same benzene ring]

wherein A=$CO_2H$, $CO_2CH_3$, $NO_2$, $SO_3H$ or $PO_3H_2$;

wherein B=CH, N, O or S;

wherein $R_1$ and $R_2$=H, $NO_2$ or $(CH_m)_nX_1$ where m=1 or 2, n is an integer from 0 to 4 and $X_1$=guanidino, OH, $NH_2$, SH, $NO_2$, F, Cl, Br, I, CN, $CF_3$, $CO_2H$, $SO_3H$ or $PO_3H_2$;

wherein $R_3$ and $R_4$=H, $(CH_o)_pCHX_2CH_2X_2$, $NH(CH_o)_pCHX_2CH_2X_2$, $NHCO(CH_o)_pCH_2X_2$ or $NHCO(CH_o)_pCHX_2CH_2X_2$ where o= 1 or 2, p is an integer from 0 to 4 and $X_2$=H, guanidino, OH, $NH_2$, SH, $NO_2$, $CF_3$, $CO_2H$, $SO_3H$ or $PO_3H_2$;

wherein $R_5$=H, OH, $NH_2$, $(CH_k)_1X_3$, $CO(CH_k)_1X_3$, $SO(CH_k)_1X_3$ or $SO_2(CH_k)_1X_3$ where k=1 or 2, l is an integer from 0 to 4 and $X_3$=guanidino, OH, $NH_2$, SH, $NO_2$, $CF_3$, $CO_2H$, $SO_3H$ or $PO_3H_2$; and wherein $R_6$=H, $CH(OH)X_4$, $CH(NH_2)X_4$, $COX_4$, $SOX_4$, or $SO_2X_4$, where $X_4$=H, $CH_3$, $CH_3CH_2$, $CH_3CHCH_3$, $CH_3CH_2CH_2$ or halogen substituted analogs of $X_4$.

8. A method of inhibiting influenza virus neuraminidase comprising the step of: administering to a subject a pharmaceutically acceptable amount of a composition comprising effective amounts of a pharmaceutically acceptable carder and a compound, its analogs, its pharmaceutically acceptable salts, derivatives, or mixtures thereof having the following formula:

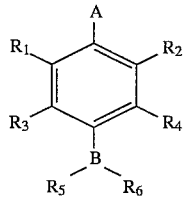

wherein A=$CO_2H$ or $CO_2CH_3$;
wherein B=CH or N;
wherein $R_1$ and $R_2$=H or $NO_2$;
wherein $R_3$=H, OH, $NH_2$, guanidino, $NO_2$, F, Cl or Br;
wherein $R_4$=$QR_7$ where Q=O, NH or $CH_2$ and $R_7$=H, $(CH_2)_oX_1$, $(CH_2)_oCHX_1CH_2X_1$, $CO(CH_2)_oCH_2X_1$ or $CO(CH_2)_oCHX_1CH_2X_1$ where o is an integer from 0 to 4 and $X_1$=H, guanidino, OH or $NH_2$;
wherein $R_5$=$COCH_3$; and
wherein $R_6$=$(CH_2)_pX_2$ where p is an integer from 0 to 4 and $X_2$=OH, $NH_2$ or guanidino.

9. A method of inhibiting influenza virus neuraminidase comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

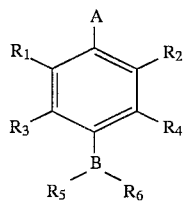

wherein A=$CO_2H$ or $CO_2CH_3$;
wherein B=N;
wherein $R_1$=H or $NO_2$;
wherein $R_2$=H or $NO_2$;
wherein $R_3$=H, OH, $NO_2$, $NH_2$ or guanidino;
wherein $R_4$=H, OH, OAc, $NH_2$, guanidino, $NHCOCH_2OH$, $NHCOCH(OH)CH_2OH$, $NHCOCH_2NH_2$, $NHCOCH_2CH_2CH_2NH_2$, CHO, $CH_2OH$, $CH_2OAc$, $CH_2CH_2OH$, $CH_2CH_2CH_2OH$, $CH_2CH(OH)CH_2OH$, $CH_2CH_2CH_2CH_2OH$, $CH_2CH_2CH(OH)CH_2OH$, $CH_2I$, CH=$CH_2$, $CH_2CH$=$CH_2$ or $CH_2CH_2CH$=$CH_2$;
wherein $R_5$=H; and
wherein $R_6$=$COCH_3$.

10. A method of making a composition for inhibiting influenza virus neuraminidase, comprising the steps of admixing effective mounts of a pharmaceutically acceptable carrier with a compound, it analogs, its pharmaceutically acceptable salts, derivatives, or mixtures thereof, having the following formula:

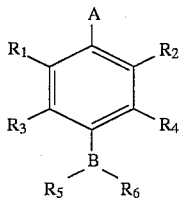

wherein A=$CO_2H$, $CO_2H_3$, $NO_2$, $SO_3H$ or $PO_3H_2$;
wherein B=CH, N, O or S;
wherein $R_1$ and $R_2$=H, $NO_2$ or $(CH_m)_nX_1$ where m=1 or 2, n is an integer from 0 to 4 and $X_1$=guanidino, OH, $NH_2$, SH, $NO_2$, F, Cl, Br, I, CN, $CF_3$, $CO_2H$, $SO_3H$ or $PO_3H_2$;
wherein $R_3$ and $R_4$=H, $(CH_o)_pX_2$, $(CH_o)_pCHX_2CH_2X_2$, $NH(CH_o)_pCHX_2CH_2X_2$, $NHCO(CH_o)_pCH_2X_2$ or $NHCO(CH_o)_pCHX_2CH_2X_2$ where o= 1 or 2, p is an integer from 0 to 4 and $X_2$=H, guanidino, OH, $NH_2$, SH, $NO_2$, $CF_3$, $CO_2H$, $SO_3H$ or $PO_3H_2$;
wherein $R_5$=H, OH, $NH_2$, $(CH_k)_1X_3$, $CO(CH_k)_1X_3$, $SO(CH_k)_1X_3$ or $SO_2(CH_k)_1X_3$ where k=1 or 2, 1 is an integer from 0 to 4 and $X_3$=guanidino, OH, $NH_2$, SH, $NO_2$, $CF_3$, $CO_2H$, $SO_3H$ or $PO_3H_2$; and
wherein $R_6$=H, CH(OH)$X_4$, CH($NH_2$)$X_4$, CO$X_4$, SO$X_4$, or $SO_2X_4$, where $X_4$=H, $CH_3$, $CH_3CH_2$, $CH_3CHCH_3$, $CH_3CH_2CH_2$ or halogen substituted analogs of $X_4$.

11. A method of making a composition for inhibiting influenza virus neuraminidase, comprising the steps of admixing effective amounts of a pharmaceutically acceptable carrier with a compound, it analogs, its pharmaceutically acceptable salts, derivatives, or mixtures thereof, having the following formula:

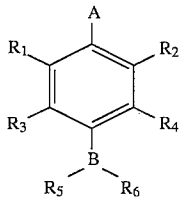

wherein A=$CO_2H$ or $CO_2CH_3$;
wherein B=CH or N;
wherein $R_1$ and $R_2$=H or $NO_2$;
wherein $R_3$=H, OH, $NH_2$, guanidino, $NO_2$, F, Cl or Br;
wherein $R_4$=$QR_7$ where Q=O, NH or $CH_2$ and $R_7$=H, $(CH_2)_oX_1$, $(CH_2)_oCHX_1CH_2X_1$, $CO(CH_2)_oCH_2X_1$ or $CO(CH_2)_oCHX_1CH_2X_1$ where o is an integer from 0 to 4 and $X_1$=H, guanidino, OH or $NH_2$;
wherein $R_5$=$COCH_3$; and
wherein $R_6$=$(CH_2)_pX_2$ where p is an integer from 0 to 4 and $X_2$=OH, $NH_2$ or guanidino.

12. A method of making a composition for inhibiting influenza virus neuraminidase, comprising the steps of admixing effective amounts of a pharmaceutically acceptable carrier with a compound, it analogs, its pharmaceutically acceptable salts, derivatives, or mixtures thereof, having the following formula:

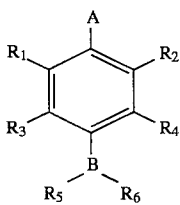

wherein A=CO$_2$H or CO$_2$CH$_3$;
wherein B=N;
wherein R$_1$=H or NO$_2$;
wherein R$_2$=H or NO$_2$;
wherein R$_3$=H, OH, NO$_2$, NH$_2$ or guanidino;
wherein R$_4$=H, OH, OAc, NH$_2$, guanidino, NHCOCH$_2$OH, NHCOCH(OH)CH$_2$OH, NHCOCH$_2$NH$_2$, NHCOCH$_2$CH$_2$CH$_2$NH$_2$, CHO, CH$_2$OH, CH$_2$OAc, CH$_2$CH$_2$OH, CH$_2$CH$_2$CH$_2$OH, CH$_2$CH(OH)CH$_2$OH, CH$_2$CH$_2$CH$_2$CH$_2$OH, CH$_2$CH$_2$CH(OH)CH$_2$OH, CH$_2$I, CH=CH$_2$, CH$_2$CH=CH$_2$ or CH$_2$CH$_2$CH=CH$_2$;
wherein R$_5$=H; and
wherein R$_6$=COCH$_3$.

13. A method of preventing influenza virus infection comprising the step of: administering to a subject a pharmaceutically acceptable mount of a composition comprising effective amounts of a pharmaceutically acceptable carrier and a compound, its analogs, its pharmaceutically acceptable salts, derivatives, or mixtures thereof having the following formula:

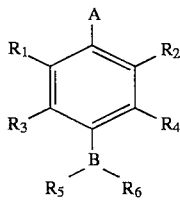

wherein A=CO$_2$H, CO$_2$CH$_3$, NO$_2$, SO$_3$H or PO$_3$H$_2$;
wherein B=CH, N, O or S;
wherein R$_1$ and R$_2$=H, NO$_2$ or (CH$_m$)$_n$X$_1$ where m=I or 2, n is an integer from 0 to 4 and X$_1$=guanidino, OH, NH$_2$, SH, NO$_2$, F, Cl, Br, I, CN, CF$_3$, CO$_2$H, SO$_3$H or PO$_3$H$_2$;
wherein R$_3$ and R$_4$=H, (CH$_o$)$_p$X$_2$, (CH$_o$)$_p$CHX$_2$CH$_2$X$_2$, NH(CH$_o$)$_p$CHX$_2$CH$_2$X$_2$, NHCO(CH$_o$)$_p$CH$_2$X$_2$ or NHCO(CH$_o$)$_p$CHX$_2$CH$_2$X$_2$ where o= 1 or 2, p is an integer from 0 to 4 and X$_2$=H, guanidino, OH, NH$_2$, SH, NO$_2$, CF$_3$, CO$_2$H, SO$_3$H or PO$_3$H$_2$;
wherein R$_5$=H, OH, NH$_2$, (CH$_k$)$_1$X$_3$, CO(CH$_k$)$_1$X$_3$, SO(CH$_k$)$_1$X$_3$ or SO$_2$(CH$_k$)$_1$X$_3$ where k=1 or 2, I is an integer from 0 to 4 and X$_3$=guanidino, OH, NH$_2$, SH, NO$_2$, CF$_3$, CO$_2$H, SO$_3$H or PO$_3$H$_2$; and
wherein R$_6$=H, CH(OH)X$_4$, CH(NH$_2$)X$_4$, COX$_4$, SOX$_4$, or SO$_2$X$_4$, where X$_4$=H, CH$_3$, CH$_3$CH$_2$, CH$_3$CHCH$_3$, CH$_3$CH$_2$CH$_2$ or halogen substituted analogs of X$_4$.

14. The method of claim 13, wherein the influenza virus infection is influenza virus type A infection.

15. The method of claim 13, wherein the influenza virus infection is influenza virus type B infection.

16. A method of preventing influenza virus infection comprising the step of: administering to a subject a pharmaceutically acceptable amount of a composition comprising effective amounts of a pharmaceutically acceptable carrier and a compound, its analogs, its pharmaceutically acceptable salts, derivatives, or mixtures thereof having the following formula:

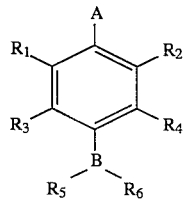

wherein A=CO$_2$H or CO$_2$CH$_3$;
wherein B=CH or N;
wherein R$_1$ and R$_2$=H or NO$_2$;
wherein R$_3$=H, OH, NH$_2$, guanidino, NO$_2$, F, Cl or Br;
wherein R$_4$=QR$_7$ where Q=O, NH or CH$_2$ and R$_7$=H, (CH$_2$)$_o$X$_1$, (CH$_2$)$_o$CHX$_1$CH$_2$X$_1$, CO(CH$_2$)$_o$CH$_2$X$_1$ or CO(CH$_2$)$_o$CHX$_1$CH$_2$X$_1$ where o is an integer from 0 to 4 and X$_1$=H, guanidino, OH or NH$_2$;
wherein R$_5$=COCH$_3$; and
wherein R$_6$=(CH$_2$)$_p$X$_2$ where p is an integer from 0 to 4 and X$_2$=OH, NH$_2$ or guanidino.

17. The method of claim 16, wherein the influenza virus infection is influenza virus type A infection.

18. The method of claim 16, wherein the influenza virus infection is influenza virus type B infection.

19. A method of preventing influenza virus infection comprising the step of: administering to a subject a pharmaceutically acceptable mount of a composition comprising effective amounts of a pharmaceutically acceptable carrier and a compound, its analogs, its pharmaceutically acceptable salts, derivatives, or mixtures thereof having the following formula:

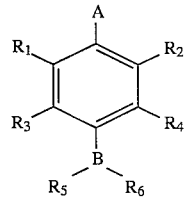

wherein A=CO$_2$H or CO$_2$CH$_3$;
wherein B=N;
wherein R$_1$=H or NO$_2$;
wherein R$_2$=H or NO$_2$;
wherein R$_3$=H, OH, NO$_2$, NH$_2$ or guanidino;
wherein R$_4$=H, OH, OAc, NH$_2$, guanidino, NHCOCH$_2$OH, NHCOCH(OH)CH$_2$OH, NHCOCH$_2$NH$_2$, NHCOCH$_2$CH$_2$CH$_2$NH$_2$, CHO, CH$_2$OH, CH$_2$OAc, CH$_2$CH$_2$OH, CH$_2$CH$_2$CH$_2$OH, CH$_2$CH(OH)CH$_2$OH, CH$_2$CH$_2$CH$_2$CH$_2$OH, CH$_2$CH$_2$CH(OH)CH$_2$OH, CH$_2$I, CH=CH$_2$, CH$_2$CH=CH$_2$ or CH$_2$CH$_2$CH=CH$_2$;
wherein R$_5$=H; and
wherein R$_6$=COCH$_3$.

20. The method of claim 19, wherein the influenza virus infection is influenza virus type A infection.

21. The method of claim 19, wherein the influenza virus infection is influenza virus type B infection.

22. A method of treating influenza virus infection comprising the step of: administering to a subject a pharmaceutically acceptable amount of a composition comprising effective mounts of a pharmaceutically acceptable carrier and a compound, its analogs, its pharmaceutically acceptable salts, derivatives, or mixtures thereof having the following formula:

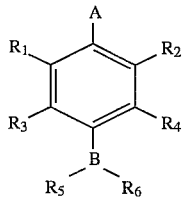

wherein A=$CO_2H$, $CO_2CH_3$, $NO_2$, $SO_3H$ or $PO_3H_2$;

wherein B=CH, N, O or S;

wherein $R_1$ and $R_2$=H, $NO_2$ or $(CH_m)_nX_1$ where m=1 or 2, n is an integer from 0 to 4 and $X_1$=guanidino, OH, $NH_2$, SH, $NO_2$, F, Cl, Br, I, CN, $CF_3$, $CO_2H$, $SO_3H$ or $PO_3H_2$;

wherein $R_3$ and $R_4$=H, $(CH_o)_pX_2$, $(CH_o)_pCHX_2CH_2X_2$, $NH(CH_o)_pCHX_2CH_2X_2$, $NHCO(CH_o)_pCH_2X_2$ or $NHCO(CH_o)_pCHX_2CH_2X_2$ where o= 1 or 2, p is an integer from 0 to 4 and $X_2$=H, guanidino, OH, $NH_2$, SH, $NO_2$, $CF_3$, $CO_2H$, $SO_3H$ or $PO_3H_2$;

wherein $R_5$=H, OH, $NH_2$, $(CH_k)_1X_3$, $CO(CH_k)_1X_3$, $SO(CH_k)_1X_3$ or $SO_2(CH_k)_1X_3$ where k=1 or 2, 1 is an integer from 0 to 4 and $X_3$=guanidino, OH, $NH_2$, SH, $NO_2$, $CF_3$, $CO_2H$, $SO_3H$ or $PO_3H_2$; and wherein $R_6$=H, CH(OH)$X_4$, CH($NH_2$)$X_4$, $COX_4$, $SOX_4$, or $SO_2X_4$, where $X_4$=H, $CH_3$, $CH_3CH_2$, $CH_3CHCH_3$, $CH_3CH_2CH_2$ or halogen substituted analogs of $x_4$.

23. The method of claim 22, wherein the influenza virus infection is influenza virus type A infection.

24. The method of claim 22, wherein the influenza virus infection is influenza virus type B infection.

25. A method of treating influenza virus infection comprising the step of: administering to a subject a pharmaceutically acceptable mount of a composition comprising effective amounts of a pharmaceutically acceptable carrier and a compound, its analogs, its pharmaceutically acceptable salts, derivatives, or mixtures thereof having the following formula:

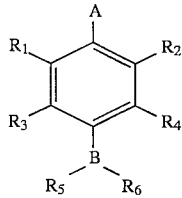

wherein A=$CO_2H$ or $CO_2CH_3$;

wherein B=CH or N;

wherein $R_1$ and $R_2$=H or $NO_2$;

wherein $R_3$=H, OH, $NH_2$, guanidino, $NO_2$, F, Cl or Br;

wherein $R_4$=$QR_7$ where Q=O, NH or $CH_2$ and $R_7$=H, $(CH_2)_oX_1$, $(CH_2)_oCHX_1CH_2X_1$, $CO(CH_2)_oCH_2X_1$ or $CO(CH_2)_oCHX_1CH_2X_1$ where o is an integer from 0 to 4 and $X_1$=H, guanidino, OH or $NH_2$;

wherein $R_5$=$COCH_3$; and wherein $R_6$=$(CH_2)_pX_2$ where p is an integer from 0 to 4 and $X_2$=OH, $NH_2$ or guanidino.

26. The method of claim 25, Wherein the influenza virus infection is influenza virus type A infection.

27. The method of claim 25, wherein the influenza virus infection is influenza virus type B infection.

28. A method of treating influenza virus infection comprising the step of: administering to a subject a pharmaceutically acceptable mount of a composition comprising effective amounts of a pharmaceutically acceptable carrier and a compound, its analogs, its pharmaceutically acceptable salts, derivatives, or mixtures thereof having the following formula:

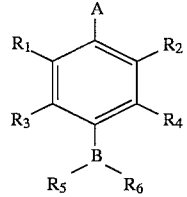

wherein A=$CO_2H$ or $CO_2CH_3$;

wherein B=N;

wherein $R_1$=H or $NO_2$;

wherein $R_2$=H or $NO_2$;

wherein $R_3$=H, OH, $NO_2$, $NH_2$ or guanidino;

wherein $R_4$=H, OH, OAc, $NH_2$, guanidino, $NHCOCH_2OH$, $NHCOCH(OH)CH_2OH$, $NHCOCH_2NH_2$, $NHCOCH_2CH_2CH_2NH_2$, CHO, $CH_2OH$, $CH_2OAc$, $CH_2CH_2OH$, $CH_2CH_2CH_2OH$, $CH_2CH(OH)CH_2OH$, $CH_2CH_2CH_2CH_2OH$, $CH_2CH_2CH(OH)CH_2OH$, $CH_2I$, CH=$CH_2$, $CH_2CH$=$CH_2$ or $CH_2CH_2CH$=$CH_2$;

wherein $R_5$=H; and wherein $R_6$=$COCH_3$.

29. The method of claim 28, wherein the influenza virus infection is influenza virus type A infection.

30. The method of claim 28; wherein the influenza virus infection is influenza virus type B infection.

31. The inhibitor of claim 1, wherein A=$CO_2H$; B=N; $R_1$=H; $R_2$=H; $R_3$=H; $R_4$=OAc; $R_5$=H; and $R_6$=$COCH_3$.

32. The inhibitor of claim 1, wherein A=$CO_2H$; B=N; $R_1$=$NO_2$; $R_2$= $NO_2$; $R_3$=H; $R_4$=OH; $R_5$=H; and $R_6$=$COCH_3$.

33. The inhibitor of claim 1, wherein A=$CO_2H$; B=N; $R_1$=H; $R_2$=H; $R_3$=$NO_2$; $R_4$=OAc; $R_5$=H; and $R_6$=$COCH_3$.

34. The inhibitor of claim 1, wherein A=$CO_2H$; B=N; $R_1$=H; $R_2$=H; $R_3$=$NO_2$; $R_4$=OH; $R_5$=H; and $R_6$=$COCH_3$.

35. The inhibitor of claim 1, wherein A=$CO_2H$; B=N; $R_1$=H; $R_2$=H; $R_3$=$NH_2$; $R_4$=OH; $R_5$=H; and $R_6$=$COCH_3$.

36. The inhibitor of claim 1, wherein A=$CO_2H$; B=N; $R_1$=H; $R_2$=H; $R_3$=H; $R_4$=$NHCOCH_2OH$; $R_5$=H; and $R_6$=$COCH_3$.

37. The inhibitor of claim 1, wherein A=$CO_2H$; B=N; $R_1$=H; $R_2$=H; $R_3$=H; $R_4$=$NHCOCH(OH)CH_2OH$; $R_5$=H; and $R_6$=$COCH_3$.

38. The inhibitor of claim 1, wherein A=$CO_2H$; B=N; $R_1$=H; $R_2$=H; $R_3$=H; $R_4$=$NHCOCH_2NH_2$; $R_5$=H; and $R_6$=$COCH_3$.

39. The inhibitor of claim 1, wherein A=$CO_2H$; B=N;

$R_1$=H; $R_2$=H; $R_3$=H; $R_4$=NHCO(CH$_2$)$_3$NH$_2$; $R_5$=H; and wherein $R_6$=COCH$_3$.

40. The inhibitor of claim 1, wherein A=CO$_2$H; B=N; $R_1$=H; $R_2$=H; $R_3$=H; $R_4$=NHC(NH)NH$_2$; $R_5$=H; and $R_6$=COCH$_3$.

41. The method of claim 7, wherein A=CO$_2$H; B=N; $R_1$=H; $R_2$=H; $R_3$=H; $R_4$=OH; $R_5$=H; and $R_6$=COCH$_3$.

42. The method of claim 7, wherein A=CO$_2$H; B=N; $R_1$=H; $R_2$=H; $R_3$=H; $R_4$=OAc; $R_5$=H; and $R_6$=COCH$_3$.

43. The method of claim 7, wherein A=CO$_2$H; B=N; $R_1$=NO$_2$; $R_2$=NO$_2$; $R_3$=H; $R_4$=OH; $R_5$=H; and $R_6$=COCH$_3$.

44. The method of claim 7, wherein A=CO$_2$H; B=N; $R_1$=H; $R_2$=H; $R_3$=NO$_2$; $R_4$=OAc; $R_5$=H; and $R_6$=COCH$_3$.

45. The method of claim 7, wherein A=CO$_2$H; B=N; $R_1$=H; $R_2$=H; $R_3$=NO$_2$; $R_4$=OH; $R_5$=H; and $R_5$=COCH$_3$.

46. The method of claim 7, wherein A=CO$_2$H; B=N; $R_1$=H; $R_2$=H; $R_3$=NH$_2$; $R_4$=OH; $R_5$=H; and $R_6$=COCH$_3$.

47. The method of claim 7, wherein A=CO$_2$H; B=N; $R_1$=H; $R_2$=H; $R_3$=H; $R_4$=NO$_2$; $R_5$=H; and $R_6$=COCH$_3$.

48. The method of claim 7, wherein A=CO$_2$H; B=N; $R_1$=H; $R_2$=H; $R_3$=H; $R_4$=NH$_2$; $R_5$=H; and $R_6$=COCH$_3$.

49. The method of claim 7, wherein A=CO$_2$H; B=N; $R_1$=H; $R_2$=H; $R_3$=H; $R_4$=NHCOCH$_2$OH; $R_5$=H; and $R_6$=COCH$_3$.

50. The method of claim 7, wherein A=CO$_2$H; B=N; $R_1$=H; $R_2$=H; $R_3$=H; $R_4$=NHCOCH(OH)CH$_2$OH; $R_5$=H; and $R_6$=COCH$_3$.

51. The method of claim 7, wherein A=CO$_2$H; B=N; $R_1$=H; $R_2$=H; $R_3$=H; $R_4$=NHCOCH$_2$NH$_2$; $R_5$=H; and $R_6$=COCH$_3$.

52. The method of claim 7, wherein A=CO$_2$H; B=N; $R_1$=H; $R_2$=H; $R_3$=H; $R_4$=NHCO(CH$_2$)$_3$NH$_2$; $R_5$=H; and $R_6$=COCH$_3$.

53. The method of claim 7, wherein A=CO$_2$H; B=N; $R_1$=H; $R_2$=H; $R_3$=H; $R_4$=NHC(NH)NH$_2$; $R_5$=H; and $R_6$=COCH$_3$.

* * * * *